(12) United States Patent
Bender et al.

(10) Patent No.: US 7,902,204 B2
(45) Date of Patent: Mar. 8, 2011

(54) DIAZAINDOLE-DICARBONYL-PIPERAZINYL ANTIVIRAL AGENTS

(75) Inventors: John A. Bender, Middletown, CT (US); Zhong Yang, Middletown, CT (US); John F. Kadow, Wallingford, CT (US); Nicholas A. Meanwell, East Hamptom, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 411 days.

(21) Appl. No.: 12/026,633

(22) Filed: Feb. 6, 2008

(65) Prior Publication Data

US 2008/0125439 A1 May 29, 2008

Related U.S. Application Data

(63) Continuation of application No. 10/979,558, filed on Nov. 2, 2004, now abandoned.

(60) Provisional application No. 60/525,624, filed on Nov. 26, 2003.

(51) Int. Cl.
*A61K 31/519* (2006.01)
*C07D 239/40* (2006.01)
*A01N 43/90* (2006.01)

(52) U.S. Cl. ..................... 514/265.1; 544/253

(58) Field of Classification Search .................. None
See application file for complete search history.

(56) References Cited

U.S. PATENT DOCUMENTS

| | | | |
|---|---|---|---|
| 5,023,265 A | 6/1991 | Scherlock et al. | |
| 5,424,329 A | 6/1995 | Boschelli et al. | |
| 6,469,006 B1 | 10/2002 | Blair et al. | |
| 6,476,034 B2 | 11/2002 | Wang et al. | |
| 6,573,262 B2 | 6/2003 | Wallace et al. | |
| 2003/0069266 A1* | 4/2003 | Wang et al. | 514/300 |
| 2003/0207910 A1* | 11/2003 | Wang et al. | 514/300 |
| 2004/0110785 A1* | 6/2004 | Wang et al. | 514/300 |
| 2005/0075364 A1 | 4/2005 | Yeung et al. | |

FOREIGN PATENT DOCUMENTS

| | | |
|---|---|---|
| WO | WO 95/04742 | 2/1995 |
| WO | WO 96/11929 | 4/1996 |
| WO | WO 99/51224 | 10/1999 |
| WO | WO 00/00201 | 1/2000 |
| WO | WO 01/22954 A2 | 4/2001 |
| WO | WO 02/10152 A2 | 2/2002 |
| WO | WO 02/085301 A2 | 10/2002 |
| WO | WO 03/068221 A1 | 8/2003 |
| WO | WO 03/092695 | 11/2003 |
| WO | WO 04/000210 A2 | 12/2003 |
| WO | WO 2004/011425 A2 | 2/2004 |
| WO | WO 2004/043337 A2 | 5/2004 |

OTHER PUBLICATIONS http://www.betterhealth.vic.gov.au/bhcv2/bhcarticles.nsf/pages/HIV_treatment, last accessed Apr. 19, 2010.*
Borisy, et. al., Proceedings of the National Academy of Sciences of the United States of America, 100(13) 2003; 7977-7982.*
M. Font, et al., "Indoles and Pyridazino[4,5-b]indoles as Non-nucleoside Analog Inhibitors of HIV-1 Reverse Transcriptase," Eur. J. Med. Chem., 30, pp. 963-971, 1995.
M. Kato, et al., "New 5-HT₃ (Serotonin-3) Receptor Antagonists. IV. Synthesis and Structure-Activity Relationships of Azabicycloalkaneacetamide Derivatives," Chem. Pharm. Bull, 43(8), pp. 1351-1357, 1995.
V. Levacher, et al., "Broadening in the Scope of NADH Models by Using Chiral and Non-Chiral Pyrrolo[2,3-b]Pyridine Derivatives,"Tetrahedron, 47(3), pp. 429-440, 1991.
E.V. Resnyanskaya, et al., "A Simple Synthesis of 1-Acyl-3-Aryl-3HPyrrolo[2',3':4,5]Pyrimido[6,1-b]Benzothiazol-6-ium-2-olates: Betainic Derivatives of a Novel Heterocyclic System," Synthesis, 18, pp. 2717-2724, 2002.
P. Dan Cook, et al., "Pyrrolopyridazines. 1. Synthesis and Reactivity of Pyrrolo[2,3-d]Pyridazine 5-Oxides," J. Het. Chem., 10(4), pp. 551-557, 1973.

* cited by examiner

Primary Examiner — Noble Jarrell
(74) Attorney, Agent, or Firm — John F. Levis

(57) ABSTRACT

The invention comprises substituted diazaindole-dicarbonyl-piperazinyl derivatives of general Formula I

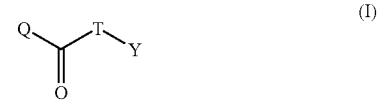

(I)

wherein:
Q is selected from the group consisting of

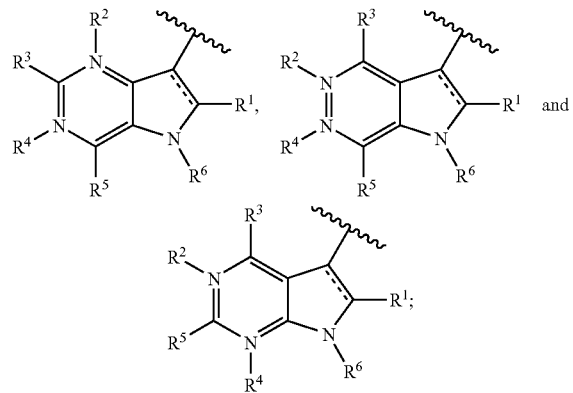

-- may represent a bond;
T is —C(O)— or —CH(CN)—; and
—Y— is selected from the group consisting of

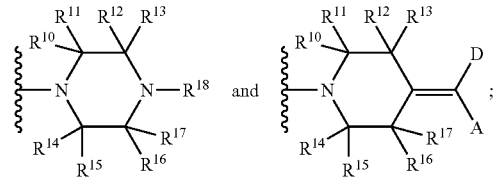

compositions thereof and their use for treating HIV infection.

16 Claims, No Drawings

DIAZAINDOLE-DICARBONYL-PIPERAZINYL ANTIVIRAL AGENTS

CROSS-REFERENCE TO RELATED APPLICATIONS

This application is a continuation of U.S. Ser. No. 10/979,558 filed Nov. 2, 2004, which claims the benefit of U.S. Provisional Application Ser. No. 60/525,624 filed Nov. 26, 2003.

BACKGROUND OF THE INVENTION

1. Field of the Invention

This invention provides compounds having drug and bioaffecting properties, their pharmaceutical compositions and method of use. In particular, the invention is concerned with new diazaindole derivatives that possess unique antiviral activity. More particularly, the present invention relates to compounds useful for the treatment of HIV and AIDS.

2. Background Art

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include ten nucleoside reverse transcriptase (RT) inhibitors or approved single pill combinations (zidovudine or AZT (or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), Combivir® (contains –3TC plus AZT), Trizivir® (contains abacavir, lamivudine, and zidovudine) and Emtriva® (emtricitabine); three non-nucleoside reverse transcriptase inhibitors: nevirapine (or Viramune®), delavirdine (or Rescriptor®) and efavirenz (or Sustiva®), nine peptidomimetic protease inhibitors or approved formulations: saquinavir, indinavir, ritonavir, nelfinavir, amprenavir, lopinavir, Kaletra® (lopinavir and Ritonavir), Atazanavir (Reyataz®), Fosamprenavir® and one fusion inhibitor which targets viral gp41 T-20 (FUZEON®). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vacca and Condra; Flexner; Berkhout and Ren et al; (Ref. 6-14)). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections (Pedersen & Pedersen, Ref 15). At least 30 different classes of NNRTI have been described in the literature (De Clercq, Ref. 16) and several NNRTIs have been evaluated in clinical trials. Dipyridodiazepinone (nevirapine), benzoxazinone (efavirenz) and bis(heteroaryl)piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance (Pedersen & Pedersen, Ref 15). A recent overview of non-nucleoside reverse transcriptase inhibitors: perspectives on novel therapeutic compounds and strategies for the treatment of HIV infection. has appeared (Buckheit, reference 99). A review covering both NRTI and NNRTIs has appeared (De Clercq, reference 100). An overview of the current state of the HIV drugs has been published (De Clercq, reference 101).

Several indole derivatives including indole-3-sulfones, piperazino indoles, pyrazino indoles, and 5H-indolo[3,2-b][1,5]benzothiazepine derivatives have been reported as HIV-1 reverse transciptase inhibitors (Greenlee et al, Ref. 1; Williams et al, Ref. 2; Romero et al, Ref. 3; Font et al, Ref. 17; Romero et al, Ref. 18; Young et al, Ref. 19; Genin et al, Ref. 20; Silvestri et al, Ref. 21). Indole 2-carboxamides have also been described as inhibitors of cell adhesion and HIV infection (Boschelli et al, U.S. Pat. No. 5,424,329, Ref. 4). 3-Substituted indole natural products (Semicochliodinol A and B, didemethylasterriquinone and isocochliodinol) were disclosed as inhibitors of HIV-1 protease (Fredenhagen et al, Ref. 22).

Structurally related aza-indole amide derivatives have been disclosed previously (Kato et al, Ref. 23(a); Levacher et al, Ref. 23(b); Dompe Spa, WO-09504742, Ref. 5(a); SmithKline Beecham PLC, WO-09611929, Ref. 5(b); Schering Corp., U.S. Pat. No. 05,023,265, Ref. 5(c)). However, these structures differ from those claimed herein in that they are monoaza-indole mono-amide rather than oxoacetamide derivatives, and there is no mention of the use of these compounds for treating viral infections, particularly HIV.

New drugs for the treatment of HIV are needed for the treatment of patients who become resistant to the currently approved drugs described above which target reverse transcriptase or the protease. One approach to obtaining these drugs is to find molecules which inhibit new and different targets of the virus. A general class of inhibitors which are under active study are HIV entry inhibitors. This general classification includes drugs aimed at several targets which include chemokine receptor (CCR5 or CXCR4) inhibitors, fusion inhibitors targeting viral gp41, and inhibitors which prevent attachment of the viral envelope, gp120, the its human cellular target CD4. A number of reviews or general papers on viral entry inhibitors have recently appeared and some selected references are:

Chemokine receptor antagonists as HIV entry inhibitors. Expert Opinion on Therapeutic Patents (2004), 14(2), 251-255.

*Inhibitors of the entry of HIV into host cells.* Meanwell, Nicholas A.; Kadow, John F. Current Opinion in Drug Discovery & Development (2003), 6(4), 451-461.

*Virus entry as a target for anti-HIV intervention.* Este, Jose A. Retrovirology Laboratory irsiCaixa, Hospital Universitari Germans Trias i Pujol, Universitat Autonoma de Barcelona, Badalona, Spain. Current Medicinal Chemistry (2003), 10(17), 1617-1632.

*New antiretroviral agents.* Rachline, A.; Joly, V. Service de Maladies Infectieuses et Tropicales A, Hopital Bichat-Claude Bernard, Paris, Fr. Antibiotiques (2003), 5(2), 77-82.

*New antiretroviral drugs.* Gulick, R. M. Cornell HIV Clinical Trials Unit, Division of International Medicine and Infectious Diseases, Weill Medical College of Cornell University, New York, N.Y., USA. Clinical Microbiology and Infection (2003), 9(3), 186-193.

*Sensitivity of HIV-1 to entry inhibitors correlates with envelope/coreceptor affinity, receptor density, and fusion kinetics.* Reeves, Jacqueline D.; Gallo, Stephen A.; Ahmad, Navid; Miamidian, John L.; Harvey, Phoebe E.; Sharron, Matthew; Pohlmann, Stefan; Sfakianos, Jeffrey N.; Derdeyn, Cynthia A.; Blumenthal, Robert; Hunter, Eric; Doms, Robert W. Department of Microbiology, University of Pennsylvania, Philadelphia, Pa., USA. Proceedings of the National Academy of Sciences of the United States of America (2002), 99(25), 16249-16254. CODEN: PNASA6 ISSN: 0027-8424.

*Opportunities and challenges in targeting HIV entry.* Biscone, Mark J.; Pierson, Theodore C.; Doms, Robert W. Department of Microbiology, University of Pennsylvania, Philadelphia, Pa., USA. Current Opinion in Pharmacology (2002), 2(5), 529-533.

*HIV entry inhibitors in clinical development.* O'Hara, Bryan M.; Olson, William C. Progenics Pharmaceuticals, Inc., Tarrytown, N.Y., USA. Current Opinion in Pharmacology (2002), 2(5), 523-528.

*Resistance mutation in HIV entry inhibitors.* Hanna, Sheri L.; Yang, Chunfu; Owen, Sherry M.; Lal, Renu B. HIV Immunology and Diagnostics Branch, Division of AIDS, STD, Atlanta, Ga., USA. AIDS (London, United Kingdom) (2002), 16(12), 1603-1608.

*HIV entry: are all receptors created equal?* Goldsmith, Mark A.; Doms, Robert W. Genencor International, Inc., Palo Alto, Calif., USA. Nature Immunology (2002), 3(8), 709-710. CODEN: NIAMCZ ISSN: 1529-2908.

*Peptide and non-peptide HIV fusion inhibitors.* Jiang, Shibo; Zhao, Qian; Debnath, Asim K. The New York Blood Center, Lindsley F. Kimball Research Institute, New York, N.Y., USA. Current Pharmaceutical Design (2002), 8(8), 563-580.

A series of recent publications and disclosures characterize and describe a compound labelled as BMS-806, an initial member of a class of viral entry inhibitors which target viral gp-120 and prevent attachment of virus to host CD4.

*A small molecule HIV-1 inhibitor that targets the HIV-1 envelope and inhibits CD4 receptor binding.* Lin, Pin-Fang; Blair, Wade; Wang, Tao; Spicer, Timothy; Guo, Qi; Zhou, Nannan; Gong, Yi-Fei; Wang, H.-G. Heidi; Rose, Ronald; Yamanaka, Gregory; Robinson, Brett; Li, Chang-Ben; Fridell, Robert; Deminie, Carol; Demers, Gwendeline; Yang, Zheng; Zadjura, Lisa; Meanwell, Nicholas; Colonno, Richard. Proceedings of the National Academy of Sciences of the United States of America (2003), 100(19), 11013-11018.

*Biochemical and genetic characterizations of a novel human immunodeficiency virus type 1 inhibitor that blocks gp120-CD4 interactions.* Guo, Qi; Ho, Hsu-Tso; Dicker, Ira; Fan, Li; Zhou, Nannan; Friborg, Jacques; Wang, Tao; McAuliffe, Brian V.; Wang, Hwei-gene Heidi; Rose, Ronald E.; Fang, Hua; Scarnati, Helen T.; Langley, David R.; Meanwell, Nicholas A.; Abraham, Ralph; Colonno, Richard J.; Lin, Pin-fang. Journal of Virology (2003), 77(19), 10528-10536.

*Method using small heterocyclic compounds for treating HIV infection by preventing interaction of CD4 and gp120.* Ho, Hsu-Tso; Dalterio, Richard A.; Guo, Qi; Lin, Pin-Fang. PCT Int. Appl. (2003), WO 2003072028A2.

*Discovery of 4-benzoyl-1-[(4-methoxy-1H-pyrrolo[2,3-b]pyridin-3-yl)oxoacetyl]-2-(R)-methylpiperazine (BMS-378806): A Novel HIV-1 Attachment Inhibitor That Interferes with CD4-gp120 Interactions.* Wang, Tao; Zhang, Zhongxing; Wallace, Owen B.; Deshpande, Milind; Fang, Haiquan; Yang, Zheng; Zadjura, Lisa M.; Tweedie, Donald L.; Huang, Stella; Zhao, Fang; Ranadive, Sunanda; Robinson, Brett S.; Gong, Yi-Fei; Ricarrdi, Keith; Spicer, Timothy P.; Deminie, Carol; Rose, Ronald; Wang, Hwei-Gene Heidi; Blair, Wade S.; Shi, Pei-Yong; Lin, Pin-fang; Colonno, Richard J.; Meanwell, Nicholas A. Journal of Medicinal Chemistry (2003), 46(20), 4236-4239.

Indole, azaindole and other oxo amide containing derivatives have been disclosed in a number different PCT and issued U.S. patent applications (Reference 93-95, 106, 108, 109, 110, 111, 112, 113, and 114). None of these applications discloses diazaindole compounds such as described in this invention. The extra nitrogen of the diazaindole class of molecules provides altered properties especially in combination with specific substituents that are advantageous and not available from the azaindoles. The diazaindoles are easier to access and thus offer the potential to provide patients with lower cost treatments. A series of PCT International Patent applications Bernd Nickel et. al. (reference 107a,b, and c) describes N-indolylglyoxamides for the treatment of cancer. Although some of these compounds contain N-heteroaryl or N-aryl piperazines, the substitution patterns at the other positions are outside the scope of this invention.

Structurally similar diazaindoles with a C-3 oxoacetyl group have also been previously disclosed (Hutchison et al, Ref 5(d); Resnyanskaya et al, Ref 24 (a); Cook et al, Ref 24(b)). However, these molecules differ from those claimed in that they do not contain the piperazine or piperidine moieties and there is no mention of the use of these molecules as antiviral agents, particularly against HIV.

Nothing in these references can be construed to disclose or suggest the novel compounds of this invention and their use to inhibit HIV infection.

REFERENCES CITED

Patent Documents

1. Greenlee, W. J.; Srinivasan, P. C. Indole reverse transcriptase inhibitors. U.S. Pat. No. 5,124,327.
2. Williams, T. M.; Ciccarone, T. M.; Saari, W. S.; Wai, J. S.; Greenlee, W. J.; Balani, S. K.; Goldman, M. E.; Theohrides, A. D. Indoles as inhibitors of HIV reverse transcriptase. European Patent 530907.
3. Romero, D. L.; Thomas, R. C.; Preparation of substituted indoles as anti-AIDS pharmaceuticals. PCT WO 93/01181.
4. Boschelli, D. H.; Connor, D. T.; Unangst, P. C. Indole-2-carboxamides as inhibitors of cell adhesion. U.S. Pat. No. 5,424,329.
5. (a) Mantovanini, M.; Melillo, G.; Daffonchio, L. Tropyl 7-azaindol-3-ylcarboxyamides as antitussive agents. PCT WO 95/04742 (Dompe Spa). (b) Cassidy, F.; Hughes, I.; Rahman, S.; Hunter, D. J. Bisheteroaryl-carbonyl and carboxamide derivatives with 5HT 2 C/2B antagonists activity. PCT WO 96/11929. (c) Scherlock, M. H.; Tom, W. C. Substituted 1H-pyrrolopyridine-3-carboxamides. U.S. Pat. No. 5,023,265. (d) Hutchison, D. R.; Martinelli, M. J.; Wilson, T. M. Preparation or pyrrolo[2,3-d]pyrimidines as sPLA2 inhibitors PCT WO 00/00201.

Other Publications

6. Larder, B. A.; Kemp, S. D. Multiple mutations in the HIV-1 reverse transcriptase confer high-level resistance to zidovudine (AZT). *Science,* 1989, 246, 1155-1158.
7. Gulick, R. M. Current antiretroviral therapy: An overview. *Quality of Life Research,* 1997, 6, 471-474.
8. Kuritzkes, D. R. HIV resistance to current therapies. *Antiviral Therapy,* 1997, 2 (Supplement 3), 61-67.
9. Morris-Jones, S.; Moyle, G.; Easterbrook, P. J. Antiretroviral therapies in HIV-1 infection. *Expert Opinion on Investigational Drugs,* 1997, 6(8), 1049-1061.
10. Schinazi, R. F.; Larder, B. A.; Mellors, J. W. Mutations in retroviral genes associated with drug resistance. International Antiviral News, 1997, 5, 129-142.
11. Vacca, J. P.; Condra, J. H. Clinically effective HIV-1 protease inhibitors. *Drug Discovery Today,* 1997, 2, 261-272.
12. Flexner, D. HIV-protease inhibitors. *Drug Therapy,* 1998, 338, 1281-1292.
13. Berkhout, B. HIV-1 evolution under pressure of protease inhibitors: Climbing the stairs of viral fitness. *J. Biomed. Sci.,* 1999, 6, 298-305.
14. Ren, S.; Lien, E. J. Development of HIV protease inhibitors: A survey. *Prog. Drug Res.,* 1998, 51, 1-31.
15. Pedersen, O. S.; Pedersen, E. B. Non-nucleoside reverse transcriptase inhibitors: the NNRTI boom. *Antiviral Chem. Chemother.* 1999, 10, 285-314.
16. (a) De Clercq, E. The role of non-nucleoside reverse transcriptase inhibitors (NNRTIs) in the therapy of HIV-1 infection. *Antiviral Research,* 1998, 38, 153-179. (b) De Clercq, E. Perspectives of non-nucleoside reverse transcriptase inhibitors (NNRTIs) in the therapy of HIV infection. IL. *Farmaco,* 1999, 54, 26-45.
17. Font, M.; Monge, A.; Cuartero, A.; Elorriaga, A.; Martinez-Irujo, J. J.; Alberdi, E.; Santiago, E.; Prieto, I.; Lasarte, J. J.; Sarobe, P. and Borras, F. Indoles and pyrazino [4,5-b]indoles as nonnucleoside analog inhibitors of HIV-1 reverse transcriptase. *Eur. J. Med. Chem.,* 1995, 30, 963-971.
18. Romero, D. L.; Morge, R. A.; Genin, M. J.; Biles, C.; Busso, M,; Resnick, L.; Althaus, I. W.; Reusser, F.; Thomas, R. C and Tarpley, W. G. Bis(heteroaryl)piperazine (BHAP) reverse transcriptase inhibitors: structure-activity relationships of novel substituted indole analogues and the identification of 1-[(5-methanesulfonamido-1H-indol-2-yl)-carbonyl]-4-[3-[1-methylethyl)amino]-pyridinyl]piperazine momomethansulfonate (U-90152S), a second generation clinical candidate. J. Med. Chem., 1993, 36, 1505-1508.
19. Young, S. D.; Amblard, M. C.; Britcher, S. F.; Grey, V. E.; Tran, L. O.; Lumma, W. C.; Huff, J. R.; Schleif, W. A.; Emini, E. E.; O'Brien, J. A.; Pettibone, D. J. 2-Heterocyclic indole-3-sulfones as inhibitors of HIV-reverse transcriptase. *Bioorg. Med. Chem. Lett.,* 1995, 5, 491-496.
20. Genin, M. J.; Poel, T. J.; Yagi, Y.; Biles, C.; Althaus, I.; Keiser, B. J.; Kopta, L. A.; Friis, J. M.; Reusser, F.; Adams, W. J.; Olmsted, R. A.; Voorman, R. L.; Thomas, R. C. and Romero, D. L. Synthesis and bioactivity of novel bis(heteroaryl)piperazine (BHAP) reverse transcriptase inhibitors: structure-activity relationships and increased metabolic stability of novel substituted pyridine analogs. *J. Med. Chem.,* 1996, 39, 5267-5275.
21. Silvestri, R.; Artico, M.; Bruno, B.; Massa, S.; Novellino, E.; Greco, G.; Marongiu, M. E.; Pani, A.; De Montis, A and La Colla, P. Synthesis and biological evaluation of 5H-indolo[3,2-b][1,5]benzothiazepine derivatives, designed as conformationally constrained analogues of the human immunodeficiency virus type 1 reverse transcriptase inhibitor L-737,126. *Antiviral Chem. Chemother.* 1998, 9, 139-148.
22. Fredenhagen, A.; Petersen, F.; Tintelnot-Blomley, M.; Rosel, J.; Mett, H and Hug, P. J. Semicochliodinol A and B: Inhibitors of HIV-1 protease and EGF-R protein Tyrosine Kinase related to Asterriquinones produced by the fungus *Chrysosporium nerdarium. Antibiotics,* 1997, 50, 395-401.
23. (a) Kato, M.; Ito, K.; Nishino, S.; Yamakuni, H.; Takasugi, H. New 5-HT$_3$ (Serotonin-3) receptor antagonists. IV. Synthesis and structure-activity relationships of azabicycloalkaneacetamide derivatives. *Chem. Pharm. Bull.,* 1995, 43, 1351-1357. (b) Levacher, V.; Benoit, R.; Duflos, J; Dupas, G.; Bourguignon, J.; Queguiner, G. Broadening the scope of NADH models by using chiral and non chiral pyrrolo[2,3-b]pyridine derivatives. *Tetrahedron,* 1991, 47, 429-440.
24. (a) Resnyanskaya, E. V.; Tverdokhlebov, A. V.; Volovenko, Y. M.; Shishkin, O. V.; Zubatyuk, R. I. A simple synthesis of 1-acyl-3-aryl-3H-pyrrolo[2',3',:4,5]pyrimido [6,1-b]benzothiazol-6-ium-2-olates: Betainic derivatives of a novel heterocyclic system. *Synthesis,* 2002, 18, 2717-2724. (b) Cook, P. D.; Castle, R. N. Pyrrolopyridazines. 1. Synthesis and reactivity of [2,3-d]pyridazine 5-oxides. *J. Het. Chem.* 1973, 10(4), 551-557.
25. Shadrina, L. P.; Dormidontov, Yu. P.; Ponomarev, V, G.; Lapkin, I. I. Reactions of organomagnesium derivatives of 7-aza- and benzoindoles with diethyl oxalate and the reactivity of ethoxalylindoles. *Khim. Geterotsikl. Soedin.,* 1987, 1206-1209.
26. Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.,* 1987, 100-106.
27. (a) Desai, M.; Watthey, J. W. H.; Zuckerman, M. A convenient preparation of 1-aroylpiperazines. *Org. Prep. Proced. Int.,* 1976, 8, 85-86. (b) Adamczyk, M.; Fino, J. R. Synthesis of procainamide metabolites. N-acetyl desethylprocainamide and desethylprocainamide. *Org. Prep. Proced. Int.* 1996, 28, 470-474. (c) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.,* 1995, 36, 6419-6422. (d) Wang, T.; Zhang, Z.; Meanwell, N. A. Benzoylation of Dianions: Preparation of mono-Benzoylated Symmetric Secondary Diamines. *J. Org. Chem.,* 1999, 64, 7661-7662.
28. Li, H.; Jiang, X.; Ye, Y.-H.; Fan, C.; Romoff, T.; Goodman, M. 3-(Diethoxyphosphoryloxy)-1,2,3-benzotriazin-4(3H)-one (DEPBT): A new coupling reagent with remarkable resistance to racemization. *Organic Lett.,* 1999, 1, 91-93.
29. Harada, N.; Kawaguchi, T.; Inoue, I.; Ohashi, M.; Oda, K.; Hashiyama, T.; Tsujihara, K. Synthesis and antitumor activity of quaternary salts of 2-(2'-oxoalkoxy)-9-hydroxyellipticines. *Chem. Pharm. Bull.,* 1997, 45, 134-137.
30. Schneller, S. W.; Luo, J.-K. Synthesis of 4-amino-1H-pyrrolo[2,3-b]pyridine (1,7-Dideazaadenine) and 1H-pyrrolo[2,3-b]pyridin-4-ol (1,7-Dideazahypoxanthine). *J. Org. Chem.,* 1980, 45, 4045-4048.

31. Shiotani, S.; Tanigochi, K. Furopyridines. XXII [1]. Elaboration of the C-substitutents alpha to the heteronitrogen atom of furo[2,3-b]-, -[3.2-b]-, -[2,3-c]- and -[3,2-c] pyridine. *J. Het. Chem.*, 1997, 34, 901-907.
32. Minakata, S.; Komatsu, M.; Ohshiro, Y. Regioselective functionalization of 1H-pyrrolo[2,3-b]pyridine via its N-oxide. *Synthesis*, 1992, 661-663.
33. Klemm, L. H.; Hartling, R. Chemistry of thienopyridines. XXIV. Two transformations of thieno[2,3-b]pyridine 7-oxide (1). *J. Het. Chem.*, 1976, 13, 1197-1200.
34. Antonini, I.; Claudi, F.; Cristalli, G.; Franchetti, P.; Crifantini, M.; Martelli, S. Synthesis of 4-amino-1-β-D-ribofuranosyl-1H-pyrrolo[2,3-b]pyridine (1-Deazatubercidin) as a potential antitumor agent. *J. Med. Chem.*, 1982, 25, 1258-1261.
35. (a) Regnouf De Vains, J. B.; Papet, A. L.; Marsura, A. New symmetric and unsymmetric polyfunctionalized 2,2'-bipyridines. *J. Het. Chem.*, 1994, 31, 1069-1077. (b) Miura, Y.; Yoshida, M.; Hamana, M. Synthesis of 2,3-fused quinolines from 3-substituted quinoline 1-oxides. Part II, *Heterocycles*, 1993, 36, 1005-1016. (c) Profft, V. E.; Rolle, W. Uber 4-merkaptoverbindungendes 2-methylpyridins. *J. Prakt. Chem.*, 1960, 283 (11), 22-34.
36. Nesi, R.; Giomi, D.; Turchi, S.; Tedeschi, P., Ponticelli, F. A new one step synthetic approach to the isoxazolo[4,5-b] pyridine system. *Synth. Comm.*, 1992, 22, 2349-2355.
37. (a) Walser, A.; Zenchoff, G.; Fryer, R. I. Quinazolines and 1,4-benzodiazepines. 75. 7-Hydroxyaminobenzodiazepines and derivatives. *J. Med. Chem.*, 1976, 19, 1378-1381. (b) Barker, G.; Ellis, G. P. Benzopyrone. Part I. 6-Amino- and 6-hydroxy-2-substituted chromones. *J. Chem. Soc.*, 1970, 2230-2233.
38. Ayyangar, N. R.; Lahoti, R J.; Daniel, T. An alternate synthesis of 3,4-diaminobenzophenone and mebendazole. *Org. Prep. Proced. Int.*, 1991, 23, 627-631.
39. Mahadevan, I.; Rasmussen, M. Ambident heterocyclic reactivity: The alkylation of pyrrolopyridines (azaindoles, diazaindenes). *Tetrahedron*, 1993, 49, 7337-7352.
40. Chen, B. K.; Saksela, K.; Andino, R.; Baltimore, D. Distinct modes of human immunodeficiency type 1 proviral latency revealed by superinfection of nonproductively infected cell lines with recombinant luciferase-encoding viruses. *J. Virol.*, 1994, 68, 654-660.
41. Bodanszky, M.; Bodanszky, A. "*The Practice of Peptide Synthesis*" $2^{nd}$ Ed., Springer-Verlag: Berlin Heidelberg, Germany, 1994.
42. Albericio, F. et al. *J. Org. Chem.* 1998, 63, 9678.
43. Knorr, R. et al. *Tetrahedron Lett.* 1989, 30, 1927.
44. (a) Jaszay Z. M. et al. *Synth. Commun.*, 1998 28, 2761 and references cited therein; (b) Bernasconi, S. et al. *Synthesis*, 1980, 385.
45. (a) Jaszay Z. M. et al. *Synthesis*, 1989, 745 and references cited therein; (b) Nicolaou, K. C. et al. *Angew. Chem. Int. Ed.* 1999, 38, 1669.
46. Ooi, T. et al. *Synlett.* 1999, 729.
47. Ford, R. E. et al. *J. Med. Chem.* 1986, 29, 538.
48. (a) Yeung, K.-S. et al. Bristol-Myers Squibb Unpublished Results. (b) Wang, W. et al. *Tetrahedron Lett.* 1999, 40, 2501.
49. Brook, M. A. et al. *Synthesis*, 1983, 201.
50. Yamazaki, N. et al. *Tetrahedron Lett.* 1972, 5047.
51. Barry A. Bunin "The Combinatorial Index" 1998 Academic Press, San Diego/London pages 78-82.
52. Richard C. Larock Comprehensive Organic Transormations 2nd Ed. 1999, John Wiley and Sons New York.
53. M. D. Mullican et. al. *J. Med. Chem.* 1991, 34, 2186-2194.
54. Protective groups in organic synthesis 3rd ed./Theodora W. Greene and Peter G. M. Wuts. New York: Wiley, 1999.
55. Katritzky, Alan R. Lagowski, Jeanne M. The principles of heterocyclic Chemistry New York: Academic Press, 1968.
56. Paquette, Leo A. Principles of modern heterocyclic chemistry New York: Benjamin.
57. Katritzky, Alan R.; Rees, Charles W.; Comprehensive heterocyclic chemistry: the structure, reactions, synthesis, and uses of heterocyclic compounds 1st ed. Oxford (Oxfordshire); New York: Pergamon Press, 1984. 8 v.
58. Katritzky, Alan RHandbook of heterocyclic 1st ed Oxford (Oxfordshire); New York: Pergamon Press, 1985.
59. Davies, David I Aromatic Heterocyclic Oxford; New York: Oxford University Press, 1991.
60. Ellis, G. P. Synthesis of fused Chichester [Sussex]; New York: Wiley, c1987-c1992. Chemistry of heterocyclic compounds; v. 47.
61. Joule, J. A Mills, K., Smith, G. F. Heterocyclic Chemistry, 3rd ed London; New York Chapman & Hall, 1995.
62. Katritzky, Alan R., Rees, Charles W., Scriven, Eric F. V. Comprehensive heterocyclic chemistry II: a review of the literature 1982-1995.
63. The structure, reactions, synthesis, and uses of heterocyclic compounds 1st ed. Oxford; New York: Pergamon, 1996. 11 v. in 12: ill.; 28 cm.
64. Eicher, Theophil, Hauptmann, Siegfried. The chemistry of heterocycles structure, reactions, syntheses, and applications Stuttgart; New York: G. Thieme, 1995.
65. Grimmett, M. R. Imidazole and benzimidazole Synthesis London; San Diego: Academic Press, 1997.
66. Advances in heterocyclic chemistry. Published in New York by Academic Press, starting in 1963-present.
67. Gilchrist, T. L. (Thomas Lonsdale) Heterocyclic chemistry 3rd ed. Harlow, Essex: Longman, 1997, 414 p: ill.; 24 cm.
68. Farina, Vittorio; Roth, Gregory P. Recent advances in the Stille reaction; *Adv. Met.-Org. Chem.* 1996, 5, 1-53.
69. Farina, Vittorio; Krishnamurthy, Venkat; Scott, William J. The Stille reaction; Org. React. (N. Y.) (1997), 50, 1-652.
70. Stille, J. K. *Angew. Chem. Int. Ed. Engl.* 1986, 25, 508-524.
71. Norio Miyaura and Akiro Suzuki *Chem. Rev.* 1995, 95, 2457.
72. Home, D. A. *Heterocycles* 1994, 39, 139.
73. Kamitori, Y. et. al. *Heterocycles*, 1994, 37(1), 153.
74. Shawali, J. *Heterocyclic Chem.* 1976, 13, 989.
75. a) Kende, A. S. et al. *Org. Photochem. Synth.* 1972, 1, 92. b) Hankes, L. V.; *Biochem. Prep.* 1966, 11, 63. c) *Synth. Meth.* 22, 837.
76. Hulton et. al. *Synth. Comm.* 1979, 9, 789.
77. Pattanayak, B. K. et. al. *Indian J. Chem.* 1978, 16, 1030.
78. *Chemische Berichte* 1902, 35, 1545.
79. *Chemische Berichte* Ibid 1911, 44, 493.
80. Moubarak, I., Vessiere, R. *Synthesis* 1980, Vol. 1, 52-53.
81. *Ind J. Chem.* 1973, 11, 1260.
82. Roomi et. al. *Can J. Chem.* 1970, 48, 1689.
83. Sorrel, T. N. *J. Org. Chem.* 1994, 59, 1589.
84. Nitz, T. J. et. al. *J. Org. Chem.* 1994, 59, 5828-5832.
85. Bowden, K. et. al. *J. Chem. Soc.* 1946, 953.
86. Nitz, T. J. et. al. *J. Org. Chem.* 1994, 59, 5828-5832.
87. Scholkopf et. al. *Angew. Int. Ed. Engl.* 1971, 10(5), 333.
88. (a) Behun, J. D.; Levine, R. *J. Org. Chem.* 1961, 26, 3379. (b) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetra-* hedron Lett., 1995, 36, 6419-6422. (c) Jenneskens, L. W.; Mahy, J.; den Berg, E. M. M. de B.-v.; Van der Hoef, I.; Lugtenburg, *J. Recl Trav. Chim. Pays-Bas* 1995, 114, 97.

89. Wang, T.; Zhang, Z.; Meanwell, N. A. Benzoylation of Dianions: Preparation of mono-Benzoylated Symmetric Secondary Diamines. *J. Org. Chem.*, 1999, 64, 7661-7662.

90. (a) Adamczyk, M.; Fino, J. R. Synthesis of procainamide metabolites. N-acetyl desethylprocainamide and desethylprocainamide. *Org. Prep. Proced. Int.* 1996, 28, 470-474. (b) Wang, T.; Zhang, Z.; Meanwell, N. A. Regioselective mono-Benzoylation of Unsymmetrical piperazines. *J. Org. Chem.*, in press.

91. Masuzawa, K.; Kitagawa, M.; Uchida, H. *Bull Chem. Soc. Jpn.* 1967, 40, 244-245.

92. Furber, M.; Cooper, M. E.; Donald, D. K. *Tetrahedron Lett.* 1993, 34, 1351-1354.

93. Blair, Wade S.; Deshpande, Milind; Fang, Haiquan; Lin, Pin-fang; Spicer, Timothy P.; Wallace, Owen B.; Wang, Hui; Wang, Tao; Zhang, Zhongxing; Yeung, Kap-sun. Preparation of antiviral indoleoxoacetyl piperazine derivatives U.S. Pat. No. 6,469,006. Preparation of antiviral indoleoxoacetyl piperazine derivatives. PCT Int. Appl. (PCT/US00/14359), WO 0076521 A1, filed May 24, 2000, published Dec. 21, 2000.

94. Wang, Tao; Wallace, Owen B.; Zhang, Zhongxing; Meanwell, Nicholas A.; Bender, John A. Antiviral azaindole derivatives. U.S. Pat. No. 6,476,034 and Wang, Tao; Wallace, Owen B.; Zhang, Zhongxing; Meanwell, Nicholas A.; Bender, John A. Preparation of antiviral azaindole derivatives. PCT Int. Appl. (PCT/US01/02009), WO 0162255 A1, filed Jan. 19, 2001, published Aug. 30, 2001.

95. Wallace, Owen B.; Wang, Tao; Yeung, Kap-Sun; Pearce, Bradley C.; Meanwell, Nicholas A.; Qiu, Zhilei; Fang, Haiquan; Xue, Qiufen May; Yin, Zhiwei. Composition and antiviral activity of substituted indoleoxoacetic piperazine derivatives. U.S. Pat. No. 6,573,262 which is a continuation-in-part application of U.S. Ser. No. 09/888,686 filed Jun. 25, 2001 (corresponding to PCT Int. Appl. (PCT/US01/20300), WO 0204440 A1, filed Jun. 26, 2001, published Jan. 17, 2002.

96. J. L. Marco, S. T. Ingate, and P. M. Chinchon Tetrahedron 1999, 55, 7625-7644.

97. C. Thomas, F. Orecher, and P. Gmeiner Synthesis 1998, 1491.

98. M. P. Pavia, S. J. Lobbestael, C. P. Taylor, F. M. Hershenson, and D. W. Miskell.

99. Buckheit, Robert W., Jr. Expert Opinion on Investigational Drugs 2001, 10(8), 1423-1442.

100. Balzarini, J.; De Clercq, E. Antiretroviral Therapy 2001, 31-62.

101. E. De clercq Journal of Clinical Virology, 2001, 22, 73-89.

102. Merour, Jean-Yves; Joseph, Benoit. Curr. Org. Chem. (2001), 5(5), 471-506.

103. T. W. von Geldern et al. J. Med. Chem. 1996, 39, 968.

104. M. Abdaoui et al. Tetrahedron 2000, 56, 2427.

105. W. J. Spillane et al. J. Chem. Soc., Perkin Trans. 1, 1982, 3, 677.

106. Wang, Tao; Zhang, Zhongxing; Meanwell, Nicholas A.; Kadow, John F.; Yin, Zhiwei; Xue, Qiufen May. (USA). Composition and antiviral activity of substituted azaindoleoxoacetic piperazine derivatives. U.S. Pat. Appl. Publ. (2003), US 20030207910 A1 published Nov. 6, 2003 which is U.S. patent application Ser. No. 10/214,982 filed Aug. 7, 2002, which is a continuation-in-part application of U.S. Ser. No. 10/038,306 filed Jan. 2, 2002 (corresponding to PCT Int. Appl. (PCT/US02/00455), WO 02/062423 A1, filed Jan. 2, 2002, published Aug. 15, 2002.

107. a) Nickel, Bernd; Szelenyi, Istvan; Schmidt, Jurgen; Emig, Peter; Reichert, Dietmar; Gunther, Eckhard; Brune, Kay. Preparation of indolylglyoxylamides as antitumor agents. PCT Int. Appl. (1999), 47 pp. CODEN: PIXXD2 WO 9951224, b) Emig, Peter; Bacher, Gerald; Reichert, Dietmar; Baasner, Silke; Aue, Beate; Nickel, Bernd; Guenther, Eckhard. *Preparation of N-(6-quinolinyl)-3-indolylglyoxylamides as antitumor agents.* PCT Int. Appl. (2002), 4WO 2002010152A2, c) Nickel, Bernd; Klenner, Thomas; Bacher, Gerald; Beckers, Thomas; Emig, Peter; Engel, Juergen; Bruyneel, Erik; Kamp, Guenter; Peters, Kirsten. *Indolyl-3-glyoxylic acid derivatives comprising therapeutically valuable properties.* PCT Int. Appl. (2001), WO 2001022954A2.

108. Wang, Tao; Wallace, Owen B.; Meanwell, Nicholas A.; Zhang, Zhongxing; Bender, John A.; Kadow, John F.; Yeung, Kap-Sun. *Preparation of indole, azaindole, and related heterocyclic piperazinecarboxamides for treatment of AIDS.* PCT Int. Appl. WO 2002085301A2, published Oct. 31, 2002; corresponding to U.S. Patent Publication U.S. 20030096825A1, published May 22, 2003.

109. Kadow, John F.; Xue, Qiufen May; Wang, Tao; Zhang, Zhongxing; Meanwell, Nicholas A. *Preparation of indole, azaindole and related heterocyclic pyrrolidine derivatives as antiviral agents.* PCT Int. Appl. WO 2003068221A1, published Aug. 21, 2003; corresponding to U.S. Patent Publication U.S. 20030236277A1.

110. Wang, Tao; Wallace, Owen B.; Meanwell, Nicholas A.; Kadow, John F.; Zhang, Zhongxing; Yang, Zhong. *Preparation of piperazine derivatives as antiviral agents.* PCT Int. Appl. (2003), WO 2003092695 A1; corresponding to U.S. Patent Publication U.S. 20040009985A1, published Jan. 15, 2004.

111. Kadow, John F.; Regueiro-Ren, Alicia; Xue, Qiufen May. *Preparation of indolyl-, azaindolyl-, and related heterocyclic sulfonylureidopiperazines for treatment of HIV and AIDS.* PCT Int. Appl. (2003), WO 2004000210 A2; corresponding to U.S. Patent Publication U.S. 20040006090A1, published Jan. 8, 2004.

112. Regueiro-Ren, Alicia; Xue, Qiufen May; Kadow, John F.; Taylor, Malcolm. *Preparation of indolyl-, azaindolyl-, and related heterocyclic ureido and thioureido piperazines for treatment of HIV and AIDS.* PCT Int. Appl. (2004), WO 2004011425 A2; corresponding to U.S. Patent Publication U.S. 20040063746A1, published Apr. 1, 2004.

113. Wang, Tao; Zhang, Zhongxing; Meanwell, Nicholas A.; Kadow, John F.; Yin, Zhiwei; Xue, Qiufen May; Regueiro-Ren, Alicia; Matiskella, John D.; Ueda, Yasutsugu. *Composition and antiviral activity of substituted azaindoleoxoacetic piperazine derivatives.* U.S. Pat. Appl. Publ. (2004), US 2004110785 A1; published Jun. 10, 2004.

114. Wang, Tao; Kadow, John F.; Meanwell, Nicholas A.; Yeung, Kap-Sun; Zhang, Zhongxing; Yin, Zhiwei; Qiu, Zhilei; Deon, Daniel H.; James, Clint A.; Ruediger, Edward H.; Bachand, Carol. *Preparation and pharmaceutical compositions of indole, azaindole and related heterocyclic 4-alkenyl piperidine amides.* U.S. Pat. Appl. Publ. (2004), US 20040063744 A1; published Apr. 1, 2004; corresponding to PCT Intl. Appln. (2004), WO 2004/04337.

SUMMARY OF THE INVENTION

The present invention comprises compounds of Formula I, their pharmaceutical formulations, and their use in patients suffering from or susceptible to a virus such as HIV. The compounds of Formula I, which include nontoxic pharmaceutically acceptable salts thereof, have the formula and meaning as described below.

The present invention comprises compounds of Formula I, including pharmaceutically acceptable salts thereof, which are effective antiviral agents, particularly as inhibitors of HIV.

wherein:
Q is selected from the group consisting of

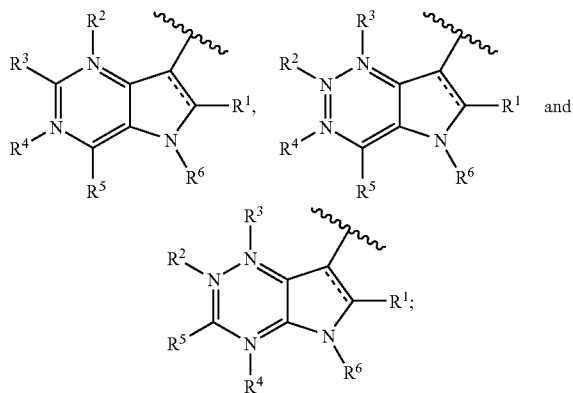

T is —C(O)— or —CH(CN)—;
$R^1$ is hydrogen or methyl;
$R^3$ and $R^5$ are independently selected from the group consisting of hydrogen, halogen, cyano, nitro, $COOR^8$, $XR^9$ and B;
$R^2$ and $R^4$ are independently O or do not exist with the proviso that only one of $R^2$ and $R^4$ are O;
$R^6$ is $(CH_2)_nH$, wherein n is 0-1;
-- represents a carbon-carbon bond or does not exist;
—Y— is selected from the group consisting of

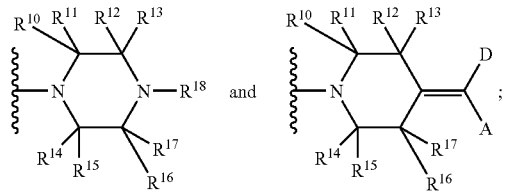

$R^{10}$, $R^{11}$, $R^{12}$, $R^{13}$, $R^{14}$, $R^{15}$, $R^{16}$ and $R^{17}$ are each independently H or $(C_{1-6})$alkyl; wherein said $(C_{1-6})$alkyl may optionally be substituted with one to three same or different halogen, OH or CN;
$R^{18}$ is a member selected from the group consisting of C(O)-phenyl, C(O)-heteroaryl, pyridinyl, pyrimidinyl, quinolyl, isoquinolyl, quinazolyl, quinoxalinyl, napthyridinyl, pthalazinyl, azabenzofuryl and azaindolyl; wherein said member is optionally substituted with from one to two substituents selected from the group consisting of methyl, -amino, —NHMe, —NMe$_2$, methoxy, hydroxymethyl and halogen;

D is selected from the group consisting of hydrogen, cyano, $S(O)_2R^{24}$, halogen, $COOR^{20}$, $C(O)NR^{21}R^{22}$, phenyl and heteroaryl; wherein said phenyl or heteroaryl is independently optionally substituted with one to three same or different halogens or from one to three same or different substituents selected from F (as defined below);

A is selected from the group consisting of phenyl, pyridinyl, furanyl, thienyl, isoxazole and oxazole; wherein said phenyl, pyridinyl, furanyl, thienyl, isoxazole or oxazole is independently optionally substituted with one to three same or different halogens or from one to three same or different substituents selected from F;

B is selected from the group consisting of $(C_{1-6})$alkyl, $C(O)NR^{21}R^{22}$, —$C(O)CH_3$, —$N(CH_2CH_2)_2NC(O)$pyrazolyl, phenyl and heteroaryl; wherein said $(C_{1-6})$alkyl, phenyl and heteroaryl are independently optionally substituted with one to three same or different halogens or from one to three same or different substituents selected from F;

heteroaryl is selected from the group consisting of pyridinyl, pyrazinyl, pyridazinyl, pyrimidinyl, furanyl, thienyl, benzothienyl, thiazolyl, oxazolyl, isoxazolyl, imidazolyl, oxadiazolyl, thiadiazolyl, pyrazolyl, tetrazolyl and triazolyl;

F is selected from the group consisting of $(C_{1-6})$alkyl, $(C_{1-6})$alkenyl, phenyl, pyridinyl, hydroxy, $(C_{1-6})$alkoxy, halogen, benzyl, —$NR^{23}C(O)$—$(C_{1-6})$alkyl, —$NR^{24}R^{25}$, —$S(O)_2NR^{24}R^{25}$, $COOR^{26}$, —$COR^{27}$, and —$CONR^{24}R^{25}$; wherein said $(C_{1-6})$alkyl or phenyl are each optionally substituted with hydroxy, $(C_{1-6})$alkoxy, $(C_{1-6})$alkyl, $CF_3$, dimethylamino or from one to three same or different halogen;

$R^8$, $R^9$ and $R^{26}$ are each independently selected from the group consisting of hydrogen and $(C_{1-6})$alkyl;

X is selected from the group consisting of $NR^{26}$, O and S;

$R^{20}$, $R^{21}$, $R^{22}$, $R^{23}$, $R^{24}$ and $R^{25}$ are independently selected from the group consisting of hydrogen, $(C_{1-6})$alkyl, phenyl and heteroaryl; wherein said phenyl and heteroaryl are each independently optionally substituted with one to three same or different halogen or methyl; and $R^{27}$ is piperazinyl, N-methyl piperazinyl, or 3-pyrazolyl.

A preferred embodiment includes compounds where T is

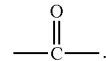

Another preferred embodiment of the invention are compounds of Formula I, including pharmaceutically acceptable salts thereof
wherein:
$R^1$ is hydrogen;
-- represents a carbon-carbon bond; and
$R^2$ and $R^4$ do not exist.
D is selected from the group consisting of hydrogen, cyano, $S(O)_2R_{24}$, halogen, $COOR^{20}$, $C(O)NH_2$, phenyl and heteroaryl; wherein said phenyl or heteroaryl is independently optionally substituted with one to three same or different halogens or a member selected from the group consisting of $(C_{1-6})$alkyl, $(C_{1-6})$alkenyl, hydroxy, $(C_{1-6})$alkoxy, halogen, —$NR^{24}R^{25}$, —$S(O)_2NR^{24}R^{25}$, $COOR^{26}$ and —$CONR^{24}R^{25}$; wherein said $(C_{1-6})$alkyl is optionally substituted with one to three same or different halogen or a hydroxy; and A is selected from the group consisting of phenyl, pyridinyl, furanyl, thienyl, isoxazole and oxazole; wherein said phenyl, pyridinyl, furanyl, thienyl, isoxazole or oxazole are independently optionally substituted with one to three same or different halogens or a member selected from the group consisting of $(C_{1-4})$alkyl, $(C_{1-4})$alkenyl, $(C_{1-3})$alkoxy, halogen and —NH$_2$; wherein said $(C_{1-3})$alkyl is optionally substituted with one to three same or different halogens.

Another preferred embodiment are compounds I wherein:

$R^6$ is hydrogen; and $R^{10}$, $R^{11}$, $R^{12}$, $R^{13}$, $R^{14}$, $R^{15}$, $R^{16}$, $R^{17}$ are each independently H or methyl with the proviso that a maximum of two of $R^{10}$-$R^{17}$ is a methyl.

Another preferred embodiment of the invention are compounds of Formula I, as above including pharmaceutically acceptable salts thereof, wherein:

Q is a member selected from groups (A), (B), and (C) consisting of

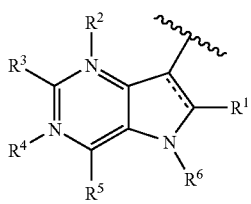
(A)

wherein $R^3$ is hydrogen, $C_1$-$C_3$ alkoxy, —NR$^{26}$R$^9$ or halogen;

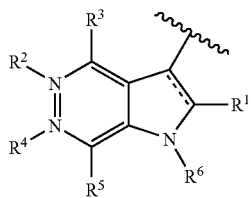
(B)

wherein $R^3$ is hydrogen, methoxy or halogen; and

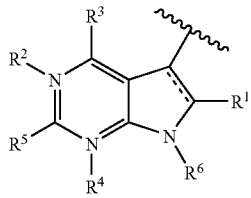
(C)

wherein $R^3$ is hydrogen, methoxy or halogen.

Another preferred embodiment of the invention are compounds of Formula I, as above including pharmaceutically acceptable salts thereof, wherein:

group (A) of Q is:

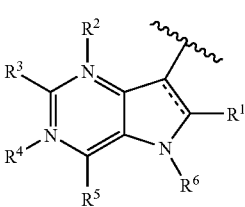
(A)

wherein $R^3$ is hydrogen; and
group (C) of Q is:

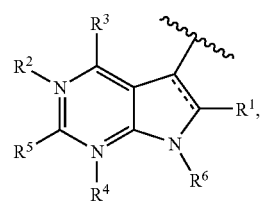

wherein:
$R^5$ is hydrogen.

In another preferred embodiment of the invention, Q is selected from group (A) or (B), and $R^5$ is selected from the group consisting of hydrogen, halogen, heteroaryl, phenyl, cyano, methoxy, COOR$^8$, C(O)NH$_2$, C(O)NHheteroaryl, and C(O)NHCH$_3$; wherein said C(O)NHheteroaryl, phenyl, and heteroaryl are independently optionally substituted with one to three same or different halogens or from one to three same or different substituents selected from F.

Other preferred embodiments are compounds I:

wherein heteroaryl is selected from the group consisting of pyridinyl, pyrazinyl, pyridazinyl, pyrimidinyl, furanyl, thienyl, thiazolyl, oxazolyl, isoxazolyl, imidazolyl, oxadiazolyl, thiadiazoyl, pyrazolyl, tetrazolyl and triazolyl; wherein said heteroaryl is independently optionally substituted with one to three same or different halogens or from one to three same or different substituents selected from F;

$R^{18}$ is —C(O)phenyl or —C(O) heteroaryl; wherein said heteroaryl is pyridinyl, furanyl or thienyl; wherein heteroaryl is independently optionally substituted with a member selected from the group consisting of halogen, methyl, -amino, —NHMe, NMe$_2$ and hydroxymethyl;

—W— is

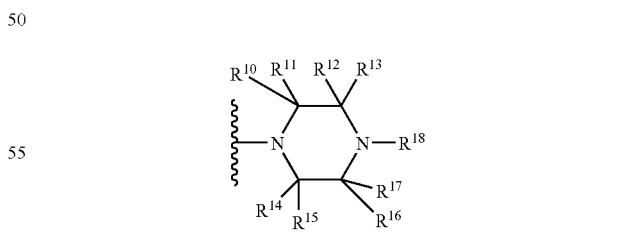

$R^{10}$, $R^{11}$, $R^{12}$, $R^{13}$, $R^{14}$, $R^{15}$, $R^{16}$ and $R^{17}$ are each independently H or methyl with the proviso that not more than one is methyl; and $R^{18}$ is selected from the group consisting of C(O)-phenyl or C(O)-heteroaryl wherein each of C(O)-phenyl or —C(O)-heteroaryl may be optionally substituted with from one to two methyl, -amino, —NHMe, —NMe$_2$, methoxy, hydroxymethyl or halogen groups; or $R^{18}$ is selected from the group consisting of pyridyl, pyrimidinyl, quinolyl, isoquinolyl, quinazolyl, quinoxalinyl, napthyridinyl, pthalazinyl, azabenzofuryl and azaindolyl, each of which may be optionally substituted with from one to two methyl, -amino, —NHMe, —NMe$_2$, methoxy, hydroxymethyl or halogen groups.

In another preferred embodiment:

—W— is selected from the group consisting of

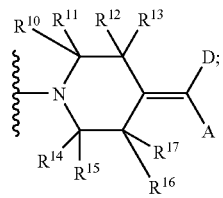

$R^{10}$, $R^{11}$, $R^{12}$, $R^{13}$, $R^{14}$, $R^{15}$, $R^{16}$ and $R^{17}$ are each independently H or methyl, with the proviso that one is methyl;

D is selected from the group consisting of hydrogen, cyano, S(O)$_2$R$^{24}$, halogen, COOR$^{20}$, C(O)NH$_2$, phenyl, or heteroaryl; wherein said phenyl or heteroaryl is independently optionally substituted with one to three same or different halogens or from one to three same or different substituents selected from the group consisting of (C$_{1-6}$)alkyl, (C$_{1-6}$)alkenyl, hydroxy, (C$_{1-6}$)alkoxy, halogen, —NR$^{24}$R$^{25}$, —S(O)$_2$NR$^{24}$R$^{25}$, COOR$^{26}$ and —CONR$^{24}$R$^{25}$; wherein said (C$_{1-6}$)alkyl is optionally substituted with one to three same or different halogen or a hydroxy; and A is selected from the group consisting of phenyl, pyridinyl, furanyl, thienyl, isoxazole and oxazole; wherein said phenyl, pyridinyl, furanyl, thienyl, isoxazole or oxazole is independently optionally substituted with one to three same or different halogens or from one to three same or different substituents selected from the group consisting of (C$_{1-4}$)alkyl, (C$_{1-4}$)alkenyl, (C$_{1-3}$)alkoxy, halogen and —NH$_2$; wherein said (C$_{1-4}$)alkyl is optionally substituted with one to three same or different halogens.

In another preferred embodiment:

Q is selected from Group (A).

Another preferred embodiment are compounds of Formula I, including pharmaceutically acceptable salts thereof,

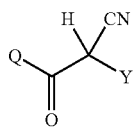

wherein:

Q is selected from the group consisting of

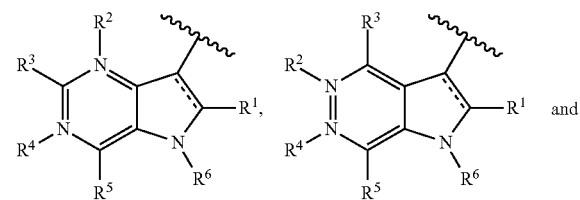

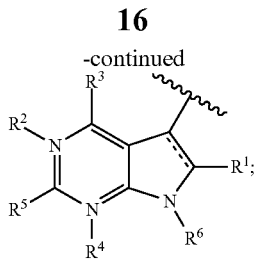

$R^1$ is hydrogen or methyl;

$R^3$ and $R^5$ are independently selected from the group consisting of hydrogen, halogen, cyano, nitro, COOR$^8$, XR$^9$ and B;

$R^2$ and $R^4$ are independently O or do not exist, with the proviso that only one of $R^2$ and $R^4$ are O;

$R^6$ is (CH$_2$)$_n$H, wherein n is 0-1;

-- represents a carbon-carbon bond or does not exist;

—Y— is selected from the group consisting of

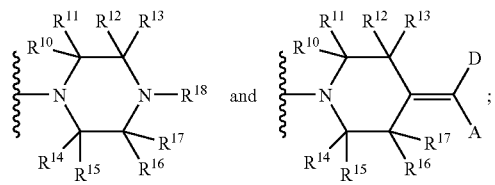

$R^{10}$, $R^{11}$, $R^{12}$, $R^{13}$, $R^{14}$, $R^{15}$, $R^{16}$ and $R^{17}$ are each independently H or (C$_{1-6}$)alkyl; wherein said (C$_{1-6}$)alkyl may optionally be substituted with one to three same or different halogen, OH or CN;

$R^{18}$ is a member selected from the group consisting of C(O)-phenyl, C(O)-heteroaryl, pyridinyl, pyrimidinyl, quinolyl, isoquinolyl, quinazolyl, quinoxalinyl, napthyridinyl, pthalazinyl, azabenzofuryl and azaindolyl; wherein said member is optionally substituted with from one to two substituents selected from the group consisting of methyl, -amino, —NHMe, —NMe$_2$, methoxy, hydroxymethyl and halogen;

D is selected from the group consisting of hydrogen, cyano, S(O)$_2$R$^{24}$, halogen, COOR$^{20}$, C(O)NR$^{21}$R$^{22}$, phenyl and heteroaryl; wherein said phenyl or heteroaryl is independently optionally substituted with one to three same or different halogens or from one to three same or different substituents selected from F;

A is selected from the group consisting of phenyl, pyridinyl, furanyl, thienyl, isoxazole and oxazole; wherein said phenyl, pyridinyl, furanyl, thienyl, isoxazole or oxazole is independently optionally substituted with one to three same or different halogens or from one to three same or different substituents selected from F;

B is selected from the group consisting of (C$_{1-6}$)alkyl, (C$_{3-6}$)cycloalkyl, C(O)NR$^{21}$R$^{22}$, —C(O)CH$_3$, —N(CH$_2$CH$_2$)$_2$NC(O)pyrazolyl, phenyl and heteroaryl; wherein said (C$_{1-6}$)alkyl, phenyl and heteroaryl are independently optionally substituted with one to three same or different halogens or from one to three same or different substituents selected from F;

heteroaryl is selected from the group consisting of pyridinyl, pyrazinyl, pyridazinyl, pyrimidinyl, furanyl, thienyl, thiazolyl, oxazolyl, isoxazolyl, imidazolyl, oxadiazolyl, thiadiazolyl, pyrazolyl, tetrazolyl and triazolyl;

F is selected from the group consisting of (C$_{1-6}$)alkyl, (C$_{1-6}$)alkenyl, phenyl, pyridinyl, hydroxy, (C$_{1-6}$)alkoxy, halogen, benzyl, —NR²³C(O)—(C₁₋₆)alkyl, —NR²⁴R²⁵, —S(O)₂NR²⁴R²⁵, COOR²⁶, —COR²⁷, and —CONR²⁴R²⁵; wherein said (C₁₋₆)alkyl or phenyl are each optionally substituted with hydroxy, (C₁₋₆)alkoxy, dimethylamino or from one to three same or different halogen;

R⁸, R⁹ and R²⁶ are each independently selected from the group consisting of hydrogen and (C₁₋₆)alkyl;

X is selected from the group consisting of NR²⁶, O and S;

R²⁰, R²¹, R²², R²³, R²⁴ and R²⁵ are independently selected from the group consisting of hydrogen, (C₁₋₆)alkyl, phenyl and heteroaryl; wherein said phenyl and heteroaryl are each independently optionally substituted with one to three same or different halogen or methyl; and R²⁷ is piperazinyl, N-methylpiperazinyl or 3-pyrazolyl.

In another embodiment are Compounds I, including pharmaceutically acceptable salts, wherein:

Q is

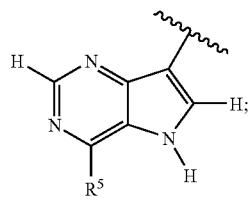

R⁵ is selected from the group consisting of hydrogen, halogen, cyano, XR⁹, heteroaryl, —N(CH₂CH₂)₂NC(O)pyrazolyl, and —C(O)CH₃, wherein said heteroaryl is optionally substituted with one substituent selected from F; heteroaryl is selected from the group consisting of pyridinyl, pyrazinyl, pyridazinyl, pyrimidinyl, isoxazolyl, isoxazolyl, pyrazolyl, and triazolyl;

—Y— is selected from the group consisting of

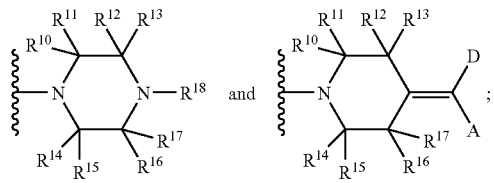

R¹⁰, R¹¹, R¹², R¹³, R¹⁴, R¹⁵, R¹⁶ and R¹⁷ are each hydrogen;

A is phenyl or pyridinyl;

R¹⁸ is C(O)-phenyl, isoquinolyl or quinazolyl;

D is cyano or oxadiazolyl;

F is selected from the group consisting of (C₁₋₆)alkyl, phenyl, pyridinyl, (C₁₋₂)alkoxy, —COOR²⁶—COR²⁷ and —CONR²⁴R²⁵; wherein said phenyl is optionally substituted with one group selected from methyl, methoxy, fluoro, or trifluoromethyl;

X is selected from the group consisting of O;

R⁹ is (C₁₋₂)alkyl;

R²⁶ is hydrogen, methyl, or ethyl;

R²⁴ and R²⁵ are independently selected from the group consisting of hydrogen and methyl; and R²⁷ is piperazinyl, N-methyl piperazinyl, or 3-pyrazolyl.

Another embodiment of the present invention is a method for treating mammals infected with the HIV virus, comprising administering to said mammal an antiviral effective amount of a compound of Formula I, including pharmaceutically acceptable salts thereof, and one or more pharmaceutically acceptable carriers, excipients or diluents; optionally the compound of Formula I can be administered in combination with an antiviral effective amount of an AIDS treatment agent selected from the group consisting of: (a) an AIDS antiviral agent; (b) an anti-infective agent; (c) an immunomodulator; and (d) HIV entry inhibitors.

Another embodiment of the present invention is a pharmaceutical composition comprising an antiviral effective amount of a compound of Formula I, including pharmaceutically acceptable salts thereof, and one or more pharmaceutically acceptable carriers, excipients, diluents and optionally in combination with an antiviral effective amount of an AIDS treatment agent selected from the group consisting of: (a) an AIDS antiviral agent; (b) an anti-infective agent; (c) an immunomodulator; and (d) HIV entry inhibitors.

DETAILED DESCRIPTION OF THE INVENTION

Since the compounds of the present invention, may possess asymmetric centers and therefore occur as mixtures of diastereomers and enantiomers, the present invention includes the individual diastereoisomeric and enantiomeric forms of the compounds of Formula I in addition to the mixtures thereof.

Definitions

The term "C₁₋₆ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —NRˣRʸ, wherein Rˣ and Rʸ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyltriazine, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —NR$^x$R$^y$, wherein R$^x$ and R$^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encomplish systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —NR$^x$R$^y$ with R$^x$ and R$^y$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a Z$_3$CC(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O)$_2$— groups with Z as defined above.

A "trihalomethanesulfonamido" group refers to a Z$_3$CS(=O)$_2$NW$^x$— group with Z and R$^X$ as defined herein.

A "sulfinyl" group refers to a —S(=O)—R" group, with R" as defined herein and, in addition, as a bond only; i.e., —S(O)—.

A "sulfonyl" group refers to a —S(=O)$_2$R" group with R" as defined herein and, in addition as a bond only; i.e., —S(O)$_2$—.

A "S-sulfonamido" group refers to a —S(=O)$_2$NR$^X$R$^Y$, with R$^X$ and R$^Y$ as defined herein.

A "N-Sulfonamido" group refers to a R"S(=O)$_2$NR$_X$— group with R$_x$ as defined herein.

A "O-carbamyl" group refers to a —OC(=O)NR$^x$R$^y$ as defined herein.

A "N-carbamyl" group refers to a R$^x$OC(=O)NR$^y$ group, with R$^x$ and R$^y$ as defined herein.

A "O-thiocarbamyl" group refers to a —OC(=S)NR$^x$R$^y$ group with R$^x$ and R$^y$ as defined herein.

A "N-thiocarbamyl" group refers to a $R^xOC(=S)NR^y$— group with $R^x$ and $R^y$ as defined herein.

An "amino" group refers to an —NH$_2$ group.

A "C-amido" group refers to a —C(=O)NR$^x$R$^y$ group with $R^x$ and $R^y$ as defined herein.

A "C-thioamido" group refers to a —C(=S)NR$^x$R$^y$ group, with $R^x$ and $R^y$ as defined herein.

A "N-amido" group refers to a $R^xC(=O)NR^y$— group, with $R^x$ and $R^y$ as defined herein.

An "ureido" group refers to a —NR$^x$C(=O)NR$^y$R$^{y2}$ group with $R^x$ and $R^y$ as defined herein and $R^{y2}$ defined the same as $R^x$ and $R^y$.

An "thioureido" group refers to a —NR$^x$C(=S)NR$^y$R$^{y2}$ group with $R^x$ and $R^y$ as defined herein and $R^{y2}$ defined the same as $R^x$ and $R^y$.

A "guanidino" group refers to a —R$^x$NC(=N)NR$^y$R$^{y2}$ group, with $R^x$, $R^y$ and $R^{y2}$ as defined herein.

A "guanyl" group refers to a R$^x$R$^y$NC(=N)— group, with $R^x$ and $R^Y$ as defined herein.

A "cyano" group refers to a —CN group.

A "silyl" group refers to a —Si(R")$_3$, with R" as defined herein.

A "phosphonyl" group refers to a P(=O)(OR$^x$)$_2$ with $R^x$ as defined herein.

A "hydrazino" group refers to a —NR$^x$NR$^y$R$^{y2}$ group with $R^x$, $R^y$ and $R^{y2}$ as defined herein.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Physiologically acceptable salts and prodrugs of compounds disclosed herein are within the scope of this invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |

| Drug Name | Manufacturer | Indication |
| --- | --- | --- |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Combivir ® | GSK | HIV infection, AIDS, (reverse transcriptase inhibitor) |
| abacavir succinate (or Ziagen ®) | GSK | HIV infection, AIDS, (reverse transcriptase inhibitor) |
| Reyataz ® (or atazanavir) | Bristol-Myers Squibb | HIV infection AIDs, protease inhibitor |
| Fuzeon ® (or T-20) | Roche/Trimeris | HIV infection AIDs, viral Fusion inhibitor |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |

-continued

| Drug Name | Manufacturer | Indication |
|---|---|---|
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*. Meanwell, Nicholas A.; Kadow, John F. Current Opinion in Drug Discovery & Development (2003), 6(4), 451-461. Specifically the compounds can be utilized in combination with other attachment inhibitors, fusion inhibitors, and chemokine receptor antagonists aimed at either the CCR5 or CXCR4 coreceptor.

It will be understood that the scope of combinations of the compounds of this invention with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is Reyataz® (active ingredient Atazanavir). Typically a dose of 300 to 600 mg is administered once a day. This may be co-administered with a low dose of Ritonavir (50 to 500 mgs). Another preferred inhibitor of HIV protease is Kaletra®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

Abbreviations

The following abbreviations, most of which are conventional abbreviations well known to those skilled in the art, are used throughout the description of the invention and the examples. Some of the abbreviations used are as follows:
h=hour(s)
r.t.=room temperature
mol=mole(s)
mmol=millimole(s)
g=gram(s)
mg=milligram(s)
mL=milliliter(s)
TFA=Trifluoroacetic Acid
DCE=1,2-Dichloroethane
$CH_2Cl_2$=Dichloromethane
TPAP=tetrapropylammonium perruthenate
THF=Tetrahydrofuran DEPBT=3-(Diethoxyphosphoryloxy)-1,2,3-benzotriazin-4(3H)-one
DMAP=4-dimethylaminopyridine
P-EDC=Polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-Diisopropylethylamine
MCPBA=meta-Chloroperbenzoic Acid
azaindole=1H-Pyrrolo-pyridine
4-azaindole=1H-pyrrolo[3,2-b]pyridine
5-azaindole=1H-Pyrrolo[3,2-c]pyridine
6-azaindole=1H-pyrrolo[2,3-c]pyridine
7-azaindole=1H-Pyrrolo[2,3-b]pyridine
4,6-diazaindole=5H-Pyrrolo[3,2-d]pyrimidine
5,6-diazaindole=1H-Pyrrolo[2,3-d]pyridazine
5,7-diazaindole=7H-Pyrrolo[2,3-d]pyrimidine
PMB=4-Methoxybenzyl
DDQ=2,3-Dichloro-5,6-dicyano-1,4-benzoquinone
OTf=Trifluoromethanesulfonoxy
NMM=4-Methylmorpholine
PIP-COPh=1-Benzoylpiperazine
NaHMDS=Sodium hexamethyldisilazide
EDAC=1-(3-Dimethylaminopropyl)-3-ethylcarbodiimide
TMS=Trimethylsilyl
DCM=Dichloromethane
DCE=Dichloroethane
MeOH=Methanol
THF=Tetrahydrofuran
EtOAc=Ethyl Acetate
LDA=Lithium diisopropylamide
TMP-Li=2,2,6,6-tetramethylpiperidinyl lithium
DME=Dimethoxyethane
DIBALH=Diisobutylaluminum hydride
HOBT=1-hydroxybenzotriazole
CBZ=Benzyloxycarbonyl
PCC=Pyridinium chlorochromate Chemistry The present invention comprises compounds of Formula I, their pharmaceutical formulations, and their use in patients suffering from or susceptible to HIV infection. The compounds of Formula I include pharmaceutically acceptable salts thereof.

The synthesis procedures and anti-HIV-1 activities of substituted diazaindole oxoacetic and piperidine containing analogs are described below.

Scheme A depicts one of the preferred methods for preparing the compounds of the invention. In this method, as shown in Step A, a functionalized diazaindole which also has a carboxy ester appended to the three position is condensed with an acetonitrile anion functionalized with Y to provide the alpha cyano ketone examples of the invention. Oxidation of these compounds as shown in Step B, provides further compounds of the invention.

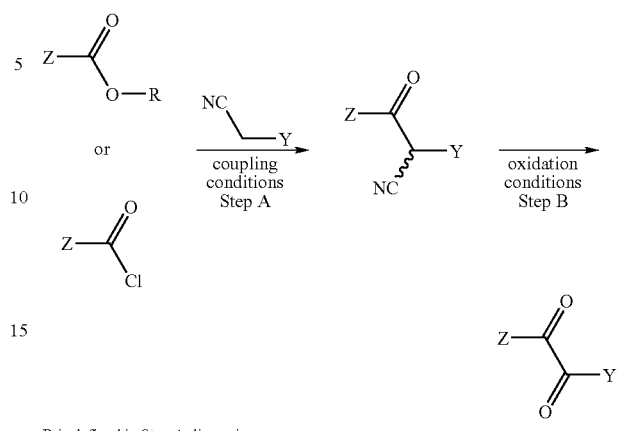

Scheme A

R is defined in Step A discussion

Step A. The carboxylic ester intermediates $Z\text{-}CO_2R$ or more preferably the acid chlorides $Z\text{-}CO_2Cl$ from Scheme A are condensed with a cyanomethyl intermediate $YCH_2CN$ under basic conditions to form the α-cyanoketo intermediate $ZC(O)CH(CN)Y$. The base KHMDS in THF at r.t. is employed most often, but other amide bases such as NaHMDS could be utilized. The typical solvent utilized is THF but DMF can be employed for less soluble molecules. Typically the reaction with an acid chloride $Z\text{-}CO_2Cl$ is conducted with the reaction flask immersed in a dry ice acetone cooling bath (~−78° C.) when THF is the solvent and an acetonitrile/acetone cooling bath (~−42° C.) when DMF is the solvent but temperatures between −78° and 50° C. could be employed in appropriate cases. The reaction is stirred between 1 h and 1 day. Typically the reaction when judged to be complete by TLC or LC or LC/MS is maintained at the cold temperature and oxidant added directly to the reaction as described in Step B. Alternatively the reaction could be allowed to attain ambient temperature and either allowed to react further if necessary and then quenched or be immediately quenched with saturated aqueous sodium bicarbonate. The mixture could then be extracted with EtOAc, concentrated and the α-cyanoketo intermediate $ZC(O)CH(CN)Y$ could be purified by preparative HPLC. When the same reaction is carried out with an ester Z-CO2R as the reactant, the alkylation reaction is initiated and then is usually allowed to warm to ambient temperature for further reaction. Typically R is methyl or ethyl or less ideally another lower alkyl group. Phenoxy, pentafluorophenoxy, or Weinreb esters (R=—NH$_2$OMe) might also be employed. As mentioned above, in the event that the carboxylic ester intermediates $Z\text{-}CO_2R$ are less reactive than desired under the standard condensation conditions, they may be activated by the initial conversion to an acid chloride Z-COCl (OR where R=H converted to Cl). This is currently the preferred method for diazaindole esters of this invention. The preparation of the acid chlorides from $Z\text{-}CO_2R$— is accomplished by initial hydrolysis of the ester to the analogous carboxylic acid $Z\text{-}CO_2H$. A typical procedure involves stirring the ester with LiOH in THF and water at 100° C. for 6 h to 2 days, concentrating the crude mixture and recrystallizing the carboxylic acid from water. The carboxylic acid $Z\text{-}CO_2H$ is then dissolved or more typically suspended as a slurry in dichloromethane and stirred with oxalyl chloride and a catalytic amount of DMF from 4-24 h but typically overnight. The solvents are removed in vacuo and the acid chloride used directly. Possible alternative solvents are benzene or toluene. A possible alternative method for conversion of the carboxylic acid to an acid chloride entails reacting thionyl chloride in benzene at 100° C. between 2 h and 6 h with the acid in the presence of catalytic DMF followed by concentration in vacuo to yield the acid chloride Z-CO$_2$Cl. As mentioned above, the acid chloride Z-CO$_2$Cl is the preferred reactant for conducting step A for the preparation of diazindole compounds of formula I. Alternatively, the acid may be converted to an acid anhydrides which may also find utility in the alkylation reaction.

Step B. The preferred method for accomplishing step B, the conversion of the α-cyanoketo intermediate ZC(O)CH(CN)Y to the diacarbonyl compounds of formula I or ketoamide intermediates to prepare compounds of formula I is to add 1-20 equivalents but most preferably 5 equivalents of a commercially available solution of 32% peracetic acid in dilute aq acetic acid to the reaction flask containing the completed reaction described in Step A. The reaction is typically stirred at the same temperature at which the alkylation reaction was conducted (for the Step A reactions with an acid chloride in THF ~−78° and for the step A reactions in DMF ~−42°) for a period of 1 h and then allowed to warm to ambient temperature if not already at that temperature. The reaction mixture is then either allowed to react further or immediately diluted with saturated aq. ammonium chloride and EtOAc. For relatively insoluble acid products which precipatate, the resultant precipitate is isolated by filtration as the oxoacetyl product ZC(O)C(O)Y. For organic soluble acid products, the acid is extracted into the organic layer and the layers separated. The organic layer is concentrated in vacuo and the product purified via preparative HPLC. The α-cyanoketo intermediate ZC(O)CH(CN)Y, if isolated, can be oxidized to the oxoacetyl product ZC(O)C(O)Y using a variety of oxidants including mCPBA, NaOCl (bleach), peracetic acid, or nickel peroxide. In a typical procedure a solution of peracetic acid in acetic acid is added to a solution of α-cyanoketo intermediate ZC(O)CH(CN)Y in THF and the reaction is stirred at between r.t. and −70° C. for between 30 min and 2 h. The reaction mixture is then diluted with saturated aq. ammonium chloride and EtOAc and the resultant precipitate is isolated by filtration as the oxoacetyl product ZC(O)C(O)Y. Step A and Step B can be combined into a one pot reaction by adding the oxidant directly to the reaction pot after the completion of step A without isolating the α-cyanoketo intermediate ZC(O)CH(CN)Y.

Scheme B depicts a typical method for preparing the cyanomethyl piperazine or piperidine analogues utilized in scheme A. Two general literature references for some of the chemistry depicted in these initial schemes are Takahashi, K.; Shibasaki, K.; Ogura, K.; Iida, H.; *Chem. Lett.* 1983, 859 or Yang; Z.; Zhang, Z.; Meanwell, N. A.; Kadow, J. F.; Wang, T.; Org. Lett. 2002, 4, 1103.

Scheme B

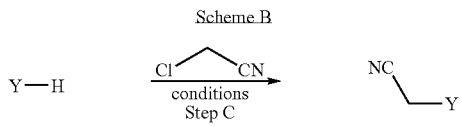

Step C. The secondary amine of a functionalized piperazine or piperidine can be alkylated with a haloacetonitrile under basic conditions to yield a cyanomethyl piperazine or piperidine analogue. In a typical procedure N-benzoyl piperazine was added to a solution of chloroacetonitrile and TEA in THF and stirred at r.t. for between 2 and 5 days. A resulting precipitate is removed by filtration, the filtrate is concentrated in vacuo, and the residue purified via chromatography to yield the cyanomethyl intermediate YCH$_2$CN. The alkylation with haloacetonitrile can also be carried out with an alternate base, such as 4-methylmorpholine or diisopropylethyl amine.

The diazaindole carboxylic ester condensation partners Z-C(O)OR utilized in Scheme A can be prepared as shown in the following schemes:

One preferred method for preparing 4,6 diazaindole is shown in Scheme C.

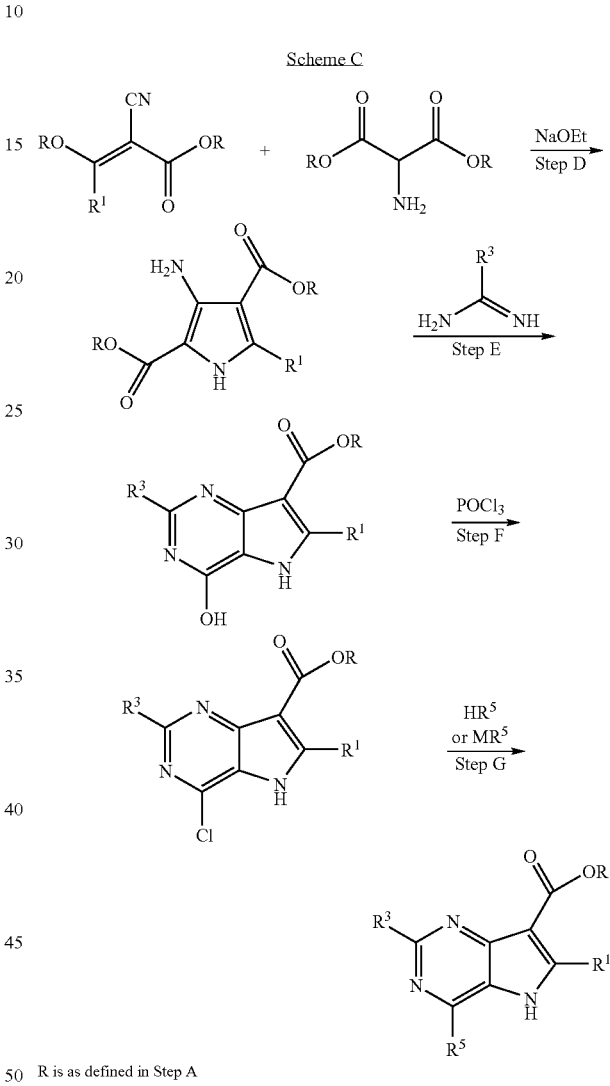

R is as defined in Step A

Step D. The reaction of an (alkoxymethylene)cyanoacetate with an amino malonate under basic conditions is known to yield a 2,4-dicarboxylic ester-3-aminopyrrole. As shown in Scheme C, step D is carried out by reacting an amino malonate with an 2-alkoxy 1-cyano acrylate in the presence of a base such as sodium ethoxide. For a representative example see; Elliot, A. J.; Montgomery, J. A., and Walsh, D. A. *Tetrahedron Lett,* 1996, 37(25), 4339-4340. A typical procedure and conditions is described in the experimental section.

Step E. The 3-Aminopyrrole 2-carboxylic ester resulting from step D can be cyclized to the desired 7-hydroxyl-4,6-diazaindole using a number of reagents including formamides, dialkyl acetal formamides, nitriles and formamidines. In a typical procedure 3-aminopyrrole-2,4-dicarboxylic acid diethyl ester and formidine acetate are heated at reflux in EtOH for 1 to 3 days. The reaction solution is filtered hot and the product usually crystallized upon cooling and is then rinsed with diethyl ether.

Step F. A 3-carboxylic ester 7-hydroxyl-4,6-diazaindole can then be converted to a 7-chloro analogue by treatment with a chlorinating reagent such as $POCl_3$ or $SOCl_2$. In a typical reaction procedure 3-ethylester-7-hydroxyl-4,6-diazaindole and $POCl_3$ are combined and heated at 105° C. for between 3 and 5 h, cooled to r.t. and diluted with diethyl ether. The precipitate that forms is collected by filtration and was shown to be the 7-chloro-4,6-diazaindole. Alternatively, when greater reactivity is desired for further functionalization and for carrying out step G, the corresponding 7-bromo-4,6-diazindole may be prepared by substituting $POBr_3$ for the chlorinating agents described above.

Step G. A 7-chloro-4,6-diazaindole can be displaced with a variety of nucleophiles to form the claimed $R^5$ substituents or intermediates from which the claimed $R^5$ substituents can be formed. Included in these are cyanide, alkoxides, amines, alcohols and various metallated species (cuprates, lithiates, zincates and Grignard reagents). In a typical procedure 3-ethylester-7-chloro-4,6-diazaindole and 3-methylpyrazole in EtOH are heated at between 100° C. and 140° C. for 20 min to 1 h. Upon cooling the reaction is concentrated and purified by silica gel chromatography or by preparative HPLC. This step may also be carried out after the initial coupling and oxidation steps (steps A and B) have been preformed on the 3-ethylester-7-chloro-4,6-diazaindole intermediate. A cyano moiety could be introduced and converted to acids, esters, amides, imidates, or heteraromatics. Typical amide coupling methodology could be used to prepare amides from acids. It should also be noted that the halogen moiety may be carried through until compounds of the invention are realized and then the conditions described in Step G may frequently be used to prepare further compounds of the invention.

Alternatively, a 7-chloro or 7-bromo-4,6-diazaindole could be coupled to a heteroaryl stannane or boronic ester via Stille or Suzuki methodology respectively. Other metal catalyzed methodology such as copper mediated displacements could also be used to prepare N linked heteraromatic or heteroalicyclic derivatives. In general, substituted diazaindoles containing a chloride, bromide, iodide, triflate, or phosphonate should undergo coupling reactions with a boronate (Suzuki type reactions) or a stannane to provide substituted diazaindoles. Stannanes and boronates are prepared via standard literature procedures or as described in the experimental section of this application. The vinyl bromides, chlorides, triflates, or phosphonates may undergo metal mediated coupling to provide compounds of formula W-H. Stille or Suzuki couplings are particularly useful. A detailed discussion of the references and best conditions for these kinds of metal mediated coupling is described later in this application where the discussion is combined with a description of how these types of reactions may also be used to functionalize diazaindoles. In additions, applications incorporated in their entirety elsewhere in this application contain methods for preparing heteroaryls from functional groups appended to indoles and azaindoles. This methodology is also applicable to diazaindoles.

One potential method for preparing the 5,6-diazaindoles QCOOR is shown in Scheme D.

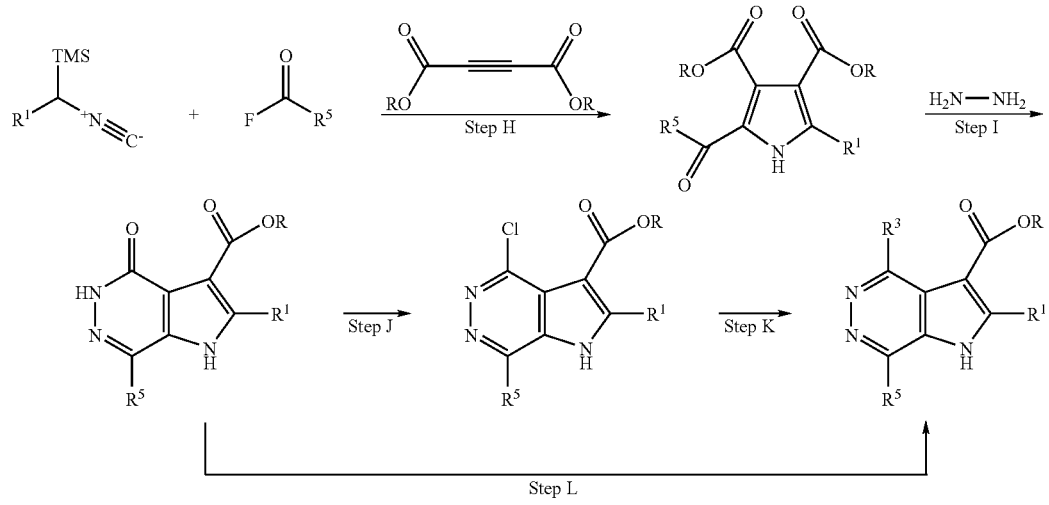

R is as defined in step J

Step H. A TMS-isocyanide would be reacted with an acid fluoride in the presence of a dialkyl acetylene dicarboxylate to form a substituted pyrrole. For representative examples see: Livinghouse, T.; Smith, R.; *J. Chem. Soc, Chem. Commun* 1983, 5, 210. In a typical procedure, trimethylsilylmethyl isocyanide (generated from the lithiation of methyl isocyanide, followed by silylation with TMSCl) would be stirred with an aryl acid fluoride and dimethyl acetylenedicarboxylate in toluene at 80° C. After a standard workup a functionalized pyrrole where $R^1$ is hydrogen and $R^5$ is aryl would be realized.

Step I. A mixture of the keto-diester-pyrrole and hydrazine dihydrochloride in ethanol heated at reflux should result in the formation of the desired 4-hydroxyl-5,6-diazaindole. Alternatively, the keto-diester-pyrrole, hydrazine hydrate and a catalytic amount of p-toluenesulfonic acid could be heated to reflux in toluene or benzene in the presence of a Dean-Stark trap and upon dehydration, the desired 4-hydroxyl-5,6-diazaindole should form.

Step J, Step K and Step L. A 4-hydroxyl-5,6-diazaindole intermediate could be converted to the intermediates in which $R^3$ is modified by direct functionalization of the hydroxyl group or by conversion of the hydroxyl group to a leaving group (halogen or triflate) followed by nucleophilic displacement or a metal (Pd or Cu) mediated coupling. These step(s) might also be carried out after the initial coupling and oxidation steps (steps A and B) have been preformed on the 4-hydroxyl-5,6-diazaindole intermediate. The conditions described for step G could also be utilized for this system.

Scheme DD

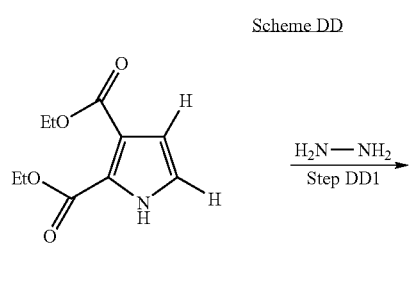

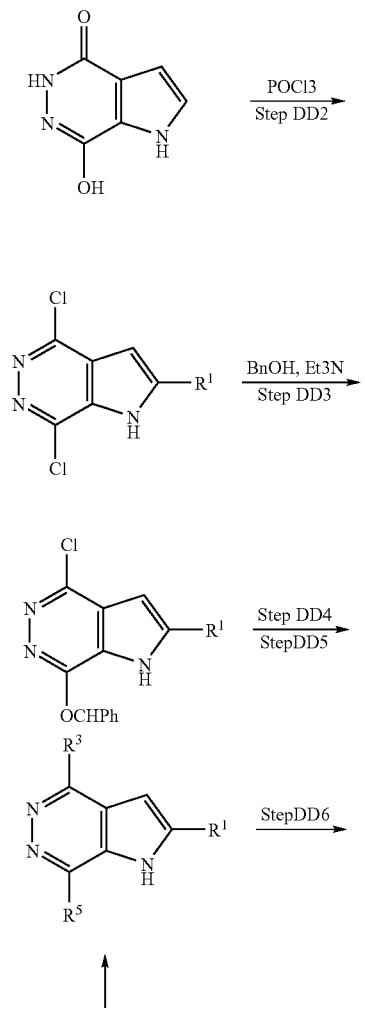

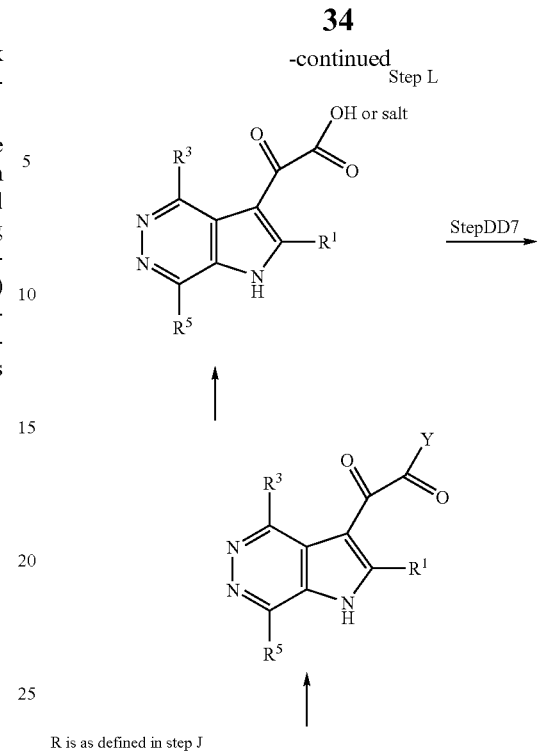

R is as defined in step J

As shown in Scheme DD pyrrole 2,3 di-carboxylic ethyl ester prepared as in either of the following two references: Roeder, Erhard; Wiedenfeld, Helmut; Bourauel, Thomas. *Synthesis of ethyl 2,3-bis(ethoxycarbonyl)-1H-pyrrole-1-propionate*. Liebigs Annalen der Chemie (1987), (12), 1117-19. and Swan, George A.; Waggott, A. *Chemistry of melanins. VI. Syntheses of 3-carboxypyrrole-2-acetic acid, 3,5-dicarboxypyrrole-2-acetic acid, and related compounds*. Journal of the Chemical Society [Section] C: Organic (1970), (2), 285-90. could be reacted with hydrazine in ethanol between RT and reflux to provide the cyclized product of step DD1. Reaction with phosphoryl chloride (2.2 to 5 equivalents should provide the dichloride as shown in step DD2. In step DD3, selective reaction of the C-7 chloride could occur by using benzyl alcohol and triethylamine in a cosolvent such as THF. In step DD4, the 4-chloro group might then be displaced with sodium or potassium methoxide in solvents such as methanol or toluene or a mixture. Stoichiometric copper I iodide could be added to speed slow reactions. In step DD5, selective hydrogenation of the benzyl group using 5 to 10% Pd/C in EtOH under a balloon pressure of hydrogen brovides the 7-hydroxy compound. Alternatively the benzyl group may be cleaved selectively with TMSI in acetonitrile at temperatures from 0 to 65° C. or using HBr in 1,2,dichloroethane at temps from −20 to 50° C. An alternate prep is to react the dichlorointemrediate above with methoxide rather than benzyl alcohol and then to selectivel cleave the C-7 ether using conditions described for the benzyl cleavage. Reacting the C-7 hydroxy group/amide tautomer with POCl3 or POBr3 would generate the chloride or bromide selectively which may be functionalized as described in step G of Scheme C for the 4,6-diazindoles. Step DD6 describes acylation of the functionalized intermediate and is done using the same procedures described in step O of Scheme F. Step DD7, amide coupling with piperazine or piperidine is carried out according to the general procedures described in Step P of Scheme F to provide compounds of the invention. It should be understood that the order of steps DD5-DD7 could be switched to determine which order provides best yields.

The 5,7-diazaindole could be prepared as shown in Scheme E. Intermediate M1 is a known compound whose synthesis has been described in the literature in the following references: Olsen, David B.; Lafemina, Robert L.; Eldrup, Anne B.; Bera, Sanjib. *Methods of inhibiting orthopoxvirus replication with nucleoside compounds*. PCT Int. Appl. (2003), 99 pp. WO 2003068244A1 Mekouar, Khalid; Deziel, Robert; Mounir, Samir; Iyer, Radhakrishnan P. *Preparation of 7-deaza L-nucleosides as antiviral agents against the hepatitis B virus*. PCT Int. Appl. (2003), WO 2003055896A2 Carroll, Steven S.; Lafemina, Robert L.; Hall, Dawn L.; Himmelberger, Amy L.; Kuo, Lawrence C.; Maccoss, Malcolm; Olsen, David B.; Rutkowski, Carrie A.; Tomassini, Joanne E.; An, Haoyun; Bhat, Balkrishen; Bhat, Neelima; Cook, Phillip Dan; Eldrup, Anne B.; Guinosso, Charles J.; Prhavc, Marija; Prakash, Thazha P. *Preparation of nucleoside derivatives as inhibitors of RNA-dependent RNA viral polymerase*. PCT Int. Appl. (2002), 235 pp. CODEN: PIXXD2 WO 2002057425A2 Carroll, Steven S.; Maccoss, Malcolm; Olsen, David B.; Bhat, Balkrishen; Bhat, Neelima; Cook, Phillip Dan; Eldrup, Anne B.; Prakash, Thazha P.; Prhavc, Marija; Song, Quanlai. *Preparation of nucleoside derivatives as inhibitors of RNA-dependent RNA viral polymerase*. PCT Int. Appl. (2002), WO 2002057287A2.

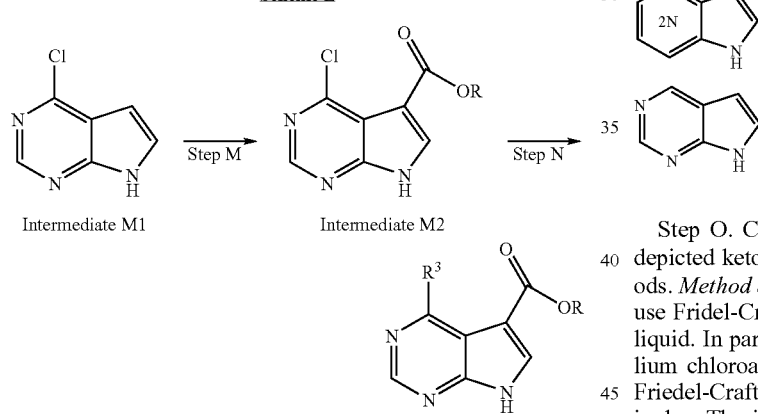

Step M. Friedel-Crafts acylation of diazindole.

Intermediate M2 where R is ethyl is a known compound which could be prepared as described in the following three literature references:

Ugarkar, Bheemarao G.; DaRe, Jay M.; Kopcho, Joseph J.; Browne, Clinton E., III; Schanzer, Juergen M.; Wiesner, James B.; Erion, Mark D. *Adenosine Kinase Inhibitors. 1. Synthesis, Enzyme Inhibition, and Anti-seizure Activity of 5-Iodotubercidin Analogues*. Journal of Medicinal Chemistry (2000), 43(15), 2883-2893.

Firestein, Gary Steven; Ugarkar, Bheemarao Ganapatrao; Miller, Leonard Paul; Gruber, Harry Edward; Bullough, David Andrew; Erion, Mark David; Castellino, Angelo John. *Preparation of adenosine kinase-inhibiting purine nucleoside analogs as antiinflammatory agents*. PCT Int. Appl. WO 9417803A1.

Browne, Clinton E.; Ugarkar, Bheemarao G.; Mullane, Kevin M.; Gruber, Harry E.; Bullough, David A.; Erion, Mark D.; Castellino, Angelo. *Adenosine kinase inhibitors*. Eur. Pat. Appl. EP 496617A1.

Step N. Nucleophilic or metal catalyzed substitution of the 4-chloro-5,7-diazaindole will yield the $R^3$ substituents of claim 1.

The diazaindole core may be coupled to the functionalized piperidine or piperazine through an oxoacetate or through an acylation/amidation process as shown in Scheme F.

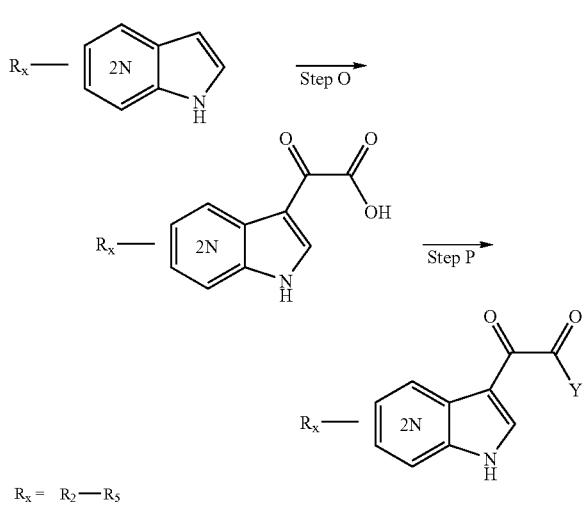

Step O. Conversion of a specific 3H-diazaindole to the depicted ketoacid might be accomplished via several methods. *Method a for step O*: One successful method has been to use Fridel-Crafts acylation conditions mediated by an ionic liquid. In particular the ionic liquid 1-alkyl-3-alkylimidazolium chloroaluminate is generally useful in promoting the Friedel-Crafts type acylation and does work with some diazainoles. The ionic liquid is generated by mixing 1-alkyl-3-alkylimidazolium chloride with aluminium chloride at room temperature with vigorous stirring. 1:2 or 1:3 molar ratio of 1-alkyl-3-alkylimidazolium chloride to aluminium chloride is preferred. One particular useful imidazolium chloroaluminate for the acylation of diazaindoles with methyl or ethyl chlorooxoacetate would be the 1-ethyl-3-methylimidazolium chloroaluminate. The reaction would typically be performed at ambient temperature and the diazaindoleglyoxyl ester would be expected to be isolated. The resulting ester could then be hydrolyzed using the hydrolysis methods for Step O described below.

More conveniently, it is probable that the glyoxyl ester could be hydrolyzed in situ at ambient temperature upon prolonged reaction time (typically overnight) to give the corresponding glyoxyl acid which would be ready for amide formation.

A representative experimental procedure is as follows: 1-ethyl-3-methylimidazolium chloride (2 equiv.; purchased from TCI; weighted under a stream of nitrogen) would be stirred in an oven-dried round bottom flask at r.t. under a nitrogen atmosphere, and then aluminium chloride (6 equiv.;

anhydrous powder packaged under argon in ampules purchased from Aldrich preferred would be added; after weighing under a stream of nitrogen). The mixture would be vigorously stirred to form a liquid, to which would then be added diazaindole (1 equiv.) followed by stirring until a homogenous mixture resulted. To the reaction mixture would then be added dropwise ethyl or methyl chlorooxoacetate (2 equiv.) and then stirring would be continued at r.t. for 2 to 24 h, probably approximately 16 h. After stirring was completed, the mixture an ice-water bath and the reaction would be quenched by carefully adding excess water. The precipitates would be filtered, washed with water and dried under high vacuum to give the diazaindoleglyoxylic acid. For some examples, 3 or even equivalents of 1-ethyl-3-methylimidazolium chloride and chlorooxoacetate may be required. A more comprehensive reference with analogous examples with non diazaindoles but with conditions that could be utilized with diazaindoles is contained in: Yeung, Kap-Sun; Farkas, Michelle E.; Qiu, Zhilei; Yang, Zhong. *Friedel-Crafts acylation of indoles in acidic imidazolium chloroaluminate ionic liquid at room temperature*. Tetrahedron Letters (2002), 43(33), 5793-5795.4 Related references: (1) Welton, T. *Chem. Rev.* 1999, 99, 2071; (2) Surette, J. K. D.; Green, L.; Singer, R. D. *Chem. Commun.* 1996, 2753; (3) Saleh, R. Y. WO 00/15594.

Step O method B. The diazaindole could be treated with a Grignard reagent such as MeMgI (methyl magnesium iodide), methyl magnesium bromide or ethyl magnesium bromide and then a zinc halide, such as $ZnCl_2$ (zinc chloride) or zinc bromide, followed by the addition of an oxalyl chloride mono ester, such as ClCOCOOMe (methyl chlorooxoacetate) or another ester as above, to afford the diaza-indole glyoxyl ester. Oxalic acid esters such as methyl oxalate, ethyl oxalate or as above are used. Aprotic solvents such as $CH_2Cl_2$, $Et_2O$, benzene, toluene, DCE, THF, dioxane or the like could potentially be used alone or in combination for this sequence.

Step O method c: A Lewis acid catalyzed Friedel-Crafts reaction under standard conditions with an alkyl chloroacetoacetate might be utilized. This could be followed by in situ by hydrolysis of the ester my the method described below to form the diazaindole ketocarboxylic acid (cite previous patent(s)). Thus the diazaindole ketoester precursors to the depicted acid could be prepared by reaction of diazaindoles with an excess of ClCOCOOMe in the presence of $AlCl_3$ (aluminum chloride). Some further descriptions of the exact procedures to carry out this reaction but on indoles or azaindoles are contained in a) Zhang, Zhongxing; Yang, Zhong; Wong, Henry; Zhu, Juliang; Meanwell, Nicholas A.; Kadow, John F.; Wang, Tao. "An Effective Procedure for the Acylation of Azaindoles at C-3." *J. Org. Chem.* 2002, 67(17), 6226-6227; b) Tao Wang et. al. U.S. Pat. No. 6,476,034 B2 "Antiviral Azaindole derivatives" published Nov. 5, 2002; c) W. Blair et al. PCT patent application WO 00/76521 A1 published Dec. 21, 2000; d) O. Wallace et. al. PCT application WO 02/04440A1 published Jan. 17, 2002. Some reactions of 5-cyano-6-chloro-7-azaindoles and lactam-lactim tautomerism in 5-cyano-6-hydroxy-7-azaindolines. Khim. Geterotsikl. Soedin., 1987, 100-106). Typically an inert solvent such as $CH_2Cl_2$ would be used but others such as THF, $Et_2O$, DCE, dioxane, benzene, or toluene may find applicability either alone or in mixtures. Other oxalate esters such as ethyl or benzyl mono esters of oxalic acid could also suffice for either method shown above. More lipophilic esters ease isolation during aqueous extractions. Lewis acid catalysts, such as tin tetrachloride, titanium IV chloride, and aluminum chloride could be employed with this transformation with aluminum chloride being most preferred.

Hydrolysis methods for Step O. Hydrolysis of a diazindole keto methyl ester would afford a potassium salt of the acid product shown as the product for Step O in Scheme F and this would then be ready for coupling with amines as shown in the next step. Acidification during workup, typically with aqueous HCl would provide the acid products from Step O as shown. Some typical conditions employ methanolic or ethanolic sodium hydroxide followed by careful acidification with aqueous hydrochloric acid of varying molarity but 1M HCl is preferred. The acidification is not utilized in many cases as described above for the preferred conditions. Lithium hydroxide or potassium hydroxide could also be employed and varying amounts of water could be added to the alcohols. Propanols or butanols could also be used as solvents. Elevated temperatures up to the boiling points of the solvents may be utilized if ambient temperatures do not suffice. Alternatively, the hydrolysis may be carried out in a non polar solvent such as $CH_2Cl_2$ or THF in the presence of Triton B. Temperatures of −78° C. to the boiling point of the solvent may be employed but −10° C. is preferred. Other conditions for ester hydrolysis are listed in reference 41 and both this reference and many of the conditions for ester hydrolysis are well known to chemists of average skill in the art.

Step P. The ketocarboxylic acid may be coupled with functionalized piperidines or piperazines using a number of standard amide bond or peptide bond forming coupling reagents. The acid intermediate Z-C(O)(O)OH from Scheme F could be coupled with either a substituted piperazine or piperidine, H—Y using standard amide bond or peptide bond forming coupling reagents. The combination of EDAC and triethylamine in tetrahydrofuran or BOPCl and diisopropyl ethyl amine in chloroform could be utilized but DEPBT, or other coupling reagents such as PyBop could be utilized. Another useful coupling condition employs HATU (L. A. Carpino et. al. J. Chem. Soc. Chem. Comm. 1994, 201-203; A. Virgilio et. al. J. Am. Chem. Soc. 1994, 116, 11580-11581). A general procedure for using this reagent is Acid (1 eq) and H—Y or H—W-Boc or HCl salt (2 eq) in DMF are stirred at rt for between 1 h and 2 days. HATU (2 eq) is added in one portion and then DMAP (3 eq). The reaction could be stirred at rt for 2 to 15 h (reaction progress monitored by standard methods ie TLC, LC/MS). The mixture is filtered through filter paper to collect the solid. The filtrate is concentrated and water is added. The mixture is filtered again and the solid is washed with water. The solid is combined and washed with water. Many reagents for amide bond couplings are known by an organic chemist skilled in the art and nearly all of these are applicable for realizing coupled amide products.

DEPBT (3-(diethoxyphosphoryloxy)-1,2,3-benzotriazin-4(3H)-one) and N,N-diisopropylethylamine, commonly known as Hunig's base, represents another efficient method to form the amide bond (step P). DEPBT is either purchased from Adrich or prepared according to the procedure of Ref. 28, Li, H.; Jiang, X.; Ye, Y.-H.; Fan, C.; Romoff, T.; Goodman, M. *Organic Lett.*, 1999, 1, 91-93. Typically an inert solvent such as DMF or THF is used but other aprotic solvents could be used.

The amide bond construction reaction could be carried out using the preferred conditions described above, the EDC conditions described below, other coupling conditions described in this application, or alternatively by applying the conditions or coupling reagents for amide bond construction described in incorporated applications for construction of substituents $R_2$-$R_5$ on indoles or azaindoles. Some specific nonlimiting examples are given in this application.

Alternatively, the acid could be converted to a methyl ester using excess diazomethane in THF/ether. The methyl ester in dry THF could be reacted with the lithium amide of intermediate H—Y. The lithium amide of H—Y, Li—Y is formed by reacting H—Y with lithium bistrimethylsilylamide in THF for 30 minutes in an ice water cooling bath. Sodium or potassium amides could be formed similarly and utilized if additional reactivity is desired. Other esters such as ethyl, phenyl, or pentafluorophenyl could be utilized and would be formed using standard methodology.

In addition, the acid can be converted to the acid chloride using oxalyl chloride in a solvent such as benzene or thionyl chloride either neat or containing a catalystic amount of DMF. Temperatures between 0° C. and reflux may be utilized depending on the substrate. Compounds of Formula I can be obtained from the resultant compounds of formula Z-C(O)(O)Cl by reaction with the appropriate H—Y in the presence of a tertiary amine (3-10 eq.) such as triethylamine or diisopropylethylamine in an anhydrous aprotic solvent such as dichloromethane, dichloroethane, diethyl ether, dioxane, THF, acetonitrile, DMF or the like at temperatures ranging from 0° C. to reflux. Most preferred are dichloromethane, dichloroethane, or THF. The reaction can be monitored by LC/MS. The 3H-diazaindoles may also be prepared under Bartoli or Liemgruber-Batchko reaction conditions as shown in scheme G. Conditions for carrying out these reactions were contained in the incorporated patent applications.

Note: For the purposes of brevity, the following symbol is taken to represent the following systems:

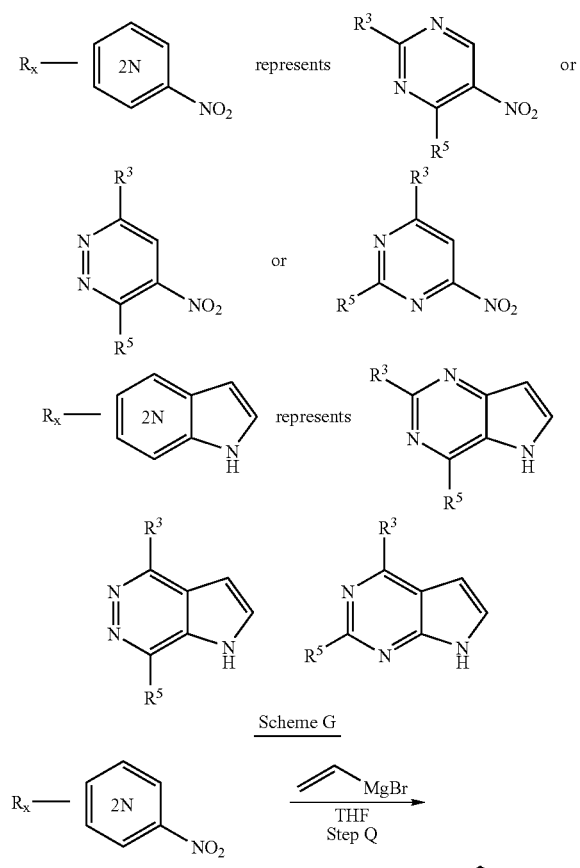

Scheme G

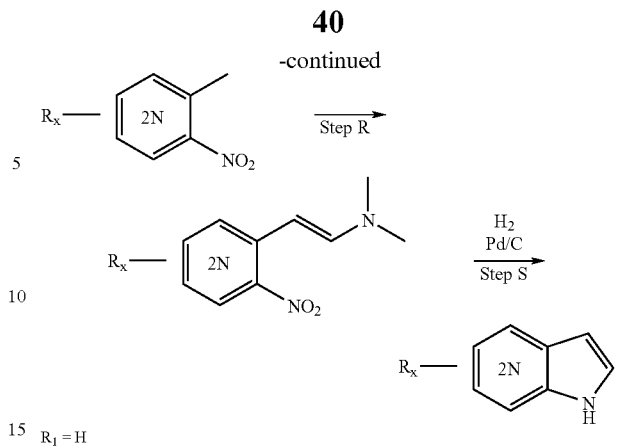

$R_1 = H$

Step Q. Step Q in Scheme G depicts a potential synthesis of a diazaindole intermediate, via the well known Bartoli reaction in which vinyl magnesium bromide reacts with an aryl or heteroaryl nitro groups, to form a five-membered nitrogen containing ring as shown. Some references for the above transformation to form an indole ring include: Bartoli et al. a) *Tetrahedron Lett.* 1989, 30, 2129. b) *J. Chem. Soc. Perkin Trans. 1* 1991, 2757. c) *J. Chem. Soc. Perkin Trans. II* 1991, 657. d) SynLett (1999), 1594. In the preferred procedure, which could be applied to diazaindole synthesis, a solution of vinyl Magnesium bromide in THF (typically 1.0M but from 0.25 to 3.0M) is added dropwise to a solution of the nitro pyridine in THF at −78° under an inert atmosphere of either nitrogen or Argon. After addition is completed, the reaction temperature is allowed to warm to −20° and then is stirred for approximately 12 h before quenching with 20% aq ammonium chloride solution. The reaction is extracted with ethyl acetate and then worked up in a typical manner using a drying agent such as anhydrous magnesium sulfate or sodium sulfate. Products are generally purified using chromatography over Silica gel. Best results are generally achieved using freshly prepared vinyl Magnesium bromide. In some cases, vinyl Magnesium chloride may be substituted for vinyl Magnesium bromide.

Step R. Reaction with dimethylformamide dimethyl acetal in an inert solvent or neat under conditions for forming Batcho-Leimgruber precursors would provide the cyclization precursor, 33, as shown. A typical condition would employ 20% DMF dimethyl acetal in DMF heated to 105-110 degrees C. Although the step is anticipated to work as shown, the pyridine may be oxidized to the N-oxide prior to the reaction using a peracid such as MCPBA or a more potent oxidant like meta-trifluoromethyl or meta nitro peroxy benzoic acids.

Step S. Reduction of the nitro group using for example hydrogenation over Pt on /C catalyst in a solvent such as MeOH, EtOH, or EtOAc could provide the cyclized product. Generally only a slight positive pressure of hydrogen would be required (a stream) but higher pressures may be needed (1.5 atm). Alternatively the reduction may be carried out using tin dichloride and HCl, hydrogenation over Raney nickel or other catalysts, or by using other methods for nitro reduction such as described elsewhere in this application.

Another possible method for preparation of 5,6-diazaindoles is shown in scheme H.

Scheme H

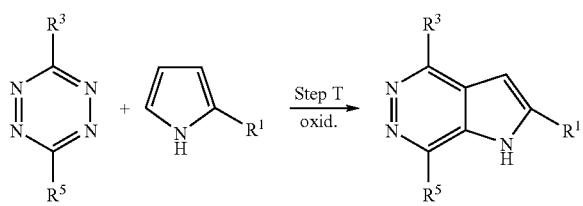

Step T. 1,2,3,4-Tetrazines have been shown to react with pyrrole and substituted pyrroles to form 5,6-diazaindole products. This reaction proceeds through a [4+2]-cycloaddition followed by a retro-[4+2]-cycloaddition to release nitrogen gas and a subsequent oxidation to establish aromaticity. For representative examples see: Seitz, Z.; Kaempchen, T.; *Arch. Pharm.* 1978, 311, 728. Takahashi, M; Ishida, H.; Kohmoto, M. *Bull Chem. Soc. Japan* 1976, 49, 1725. Benson, S. C.; Palabrica, C. A.; Snyder, J. K. *J. Org. Chem.* 1987, 52, 4610. Gonzalez, J. C.; Lobo-Antunes, J; Perez-Lourido, P.; Santana, L.; Uriate, E. *Synthesis* 2002, 4, 475-478.

Another possible method for preparing a 5,6-diazaindole with a C-3 oxoacetate is shown in Scheme I (Cook, P. D.; Castle, R. N. *J. Het. Chem.* 1973, 10, 551.

Scheme I

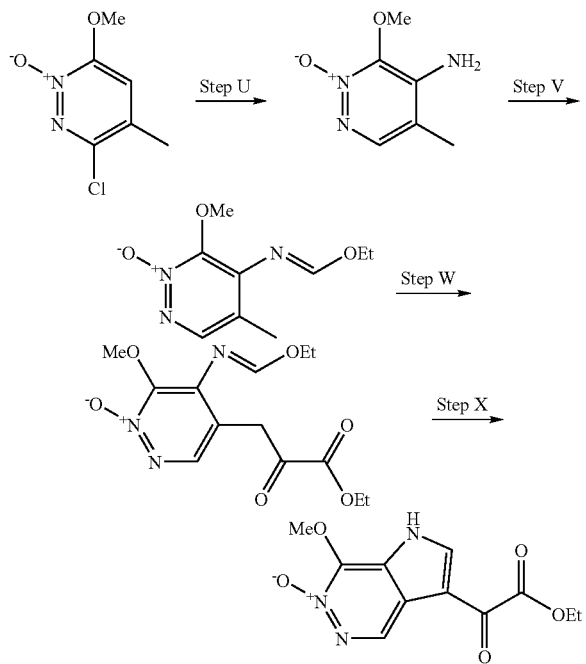

Step U. The starting pyridazine N-oxide would initially be nitrated and the resulting nitro group then would be reduced under standard conditions to an amine. The chloro would then be removed under hydrogentation conditions. Alternatively, the chloro could remain in the molecule and be carried through the subsequent steps. This should allow for the formation of a 4-chloro-5,6-diazaindole. The chloro could then be converted to a methoxy or an amino group by nucleophilic displacement or copper catalyzed assisted coupling. This would result in an intermediate that could be converted to molecules claimed within this application via previously described amide bond coupling.

Step V. The amine could then be functionalized with ethyl orthoformate under acidic conditions to form an ethoxyimine. In a typical procedure the amine and triethyl orthoformate were dissolved into a solution of DMF and ethanol that had been adjusted to pH 1 with anhydrous hydrogen chloride. The reaction was then heated to 150-160° C. and ethanol was collected by distillation resulting in the formation of the desired ethoxyimine.

Step W. Deprotonation of the methyl group followed by acylation with diethyl oxalate would yield a ketoester intermediate that could be used to form a 3-oxoacetate-5,6-diazaindole (Step X) or could be used to make a 2-carboxylate-5,6-diazaindole by hydrolysis of the imine, followed by condensation of the amine onto the ketone five centers away.

Step X The ketoester could then be cyclized onto the ethoxyimine under basic conditions to arrive at the 3-oxoacetate-5,6-diazaindole. To form the molecules of this claim, functionalized piperazine or piperidones could be coupled to the ester through standard amide bond forming reactions. This general scheme should also allow for the preparation of other 5,6-diazaindole intermediates with different $R^3$ and $R^5$ substituents by displacement or coupling to the chloro or displacement of the methoxy at some point in the sequence.

Preparations of Functionalized Piperazines and Piperidines are Described Later in the Application.

Scheme 15

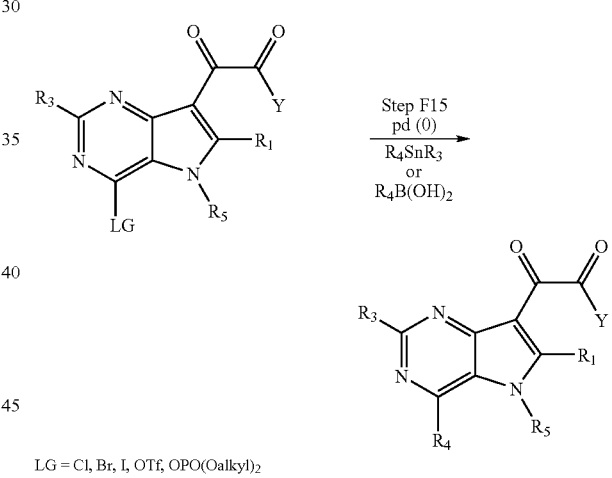

LG = Cl, Br, I, OTf, OPO(Oalkyl)$_2$

Step F15

As shown above in Scheme 15, Step F15, substituted diazaindoles containing a chloride, bromide, iodide, triflate, or phosphonate could undergo coupling reactions with a boronate (Suzuki type reactions) or a stannane to provide substituted diazaindoles. Stannanes and boronates are prepared via standard literature procedures or as described in the experimental section of this application. The substituted diazindoles may undergo metal mediated coupling to provide compounds of Formula I wherein $R^4$ is aryl, heteroaryl, or heteroalicyclic for example. The bromo or chloro diazaindole intermediates, (or diazaindole triflates or iodides) may undergo Stille-type coupling with heteroarylstannanes as shown in Scheme 15. Conditions for this reaction are well known in the art and the following are three example references a) Farina, V.; Roth, G. P. Recent advances in the Stille reaction; *Adv. Met.-Org. Chem.* 1996, 5, 1-53. b) Farina, V.; Krishnamurthy, V.; Scott, W. J. The Stille reaction; *Org. React.* (N.Y.) 1997, 50, 1-652. and c) Stille, J. K. *Angew. Chem. Int. Ed. Engl.* 1986, 25, 508-524. Other references for general coupling conditions are also in the reference by Richard C. Larock Comprehensive Organic Transformations 2nd Ed. 1999, John Wiley and Sons New York. All of these references provide numerous conditions at the disposal of those skilled in the art in addition to the specific examples provided in Scheme 15 and in the specific embodiments. It can be well recognized that an diazaindole stannane could also couple to a heterocyclic or aryl halide or triflate to construct compounds of Formula I. Suzuki coupling (Norio Miyaura and Akiro Suzuki *Chem. Rev.* 1995, 95, 2457.) between a triflate, bromo, or chloro diazaindole intermediate and a suitable boronate could also be employed and some specific examples are contained in this application. Palladium catalyzed couplings of stannanes and boronates between chloro diazaindole intermediates are also feasible and have been utilized extensively for this invention. Preferred procedures for coupling of a chloro diazaindole and a stannane employ dioxane, stoichiometric or an excess of the tin reagent (up to 5 equivalents), 0.1 to 1 eq of Palladium (0) tetrakis triphenyl phosphine in dioxane heated for 5 to 15 h at 110 to 120°. Other solvents such as DMF, THF, toluene, or benzene could be employed. Preferred procedures for Suzuki coupling of a chloro diazaindole and a boronate employ 1:1 DMF water as solvent, 2 equivalents of potassium carbonate as base stoichiometric or an excess of the boron reagent (up to 5 equivalents), 0.1 to 1 eq of Palladium (0) tetrakis triphenyl phosphine heated for 5 to 15 h at 110 to 120°. Some references (and the references therein) describing catalysts which are useful for coupling with aryl and heteroaryl chlorides are: Littke, A. F.; Dai, C.; Fu, G. C. *J. Am. Chem. Soc.* 2000, 122(17), 4020-4028; Varma, R. S.; Naicker, K. P. *Tetrahedron Lett.* 1999, 40(3), 439-442; Wallow, T. I.; Novak, B. M. *J. Org. Chem.* 1994, 59(17), 5034-7; Buchwald, S.; Old, D. W.; Wolfe, J. P.; Palucki, M.; Kamikawa, K.; Chieffi, A.; Sadighi, J. P.; Singer, R. A.; Ahman, J. PCT Int. Appl. WO 0002887 2000; Wolfe, J. P.; Buchwald, S. L. *Angew. Chem., Int. Ed.* 1999, 38(23), 3415; Wolfe, J. P.; Singer, R. A.; Yang, B. H.; Buchwald, S. L. *J. Am. Chem. Soc.* 1999, 121(41), 9550-9561; Wolfe, J. P.; Buchwald, S. L. *Angew. Chem., Int. Ed.* 1999, 38(16), 2413-2416; Bracher, F.; Hildebrand, D.; *Liebigs Ann. Chem.* 1992, 12, 1315-1319; and Bracher, F.; Hildebrand, D.; *Liebigs Ann. Chem.* 1993, 8, 837-839.

Alternatively, the boronate or stannane could potentially be formed on the diazaindole via methods known in the art and the coupling performed in the reverse manner with aryl or heteroaryl based halogens or triflates.

Known boronate or stannane agents could be either purchased from commercial resources or prepared following disclosed documents. Additional examples for the preparation of tin reagents or boronate reagents are contained in the experimental section.

Novel stannane agents could be prepared from one of the following routes.

Scheme Tin-01

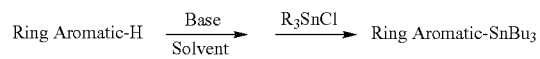

Base = LDA, TMP-Li, n-BuLi, S-BuLi, t-BuLi
Solvent = THF, ether, DME
R = Me, Bu

Scheme Tin-02

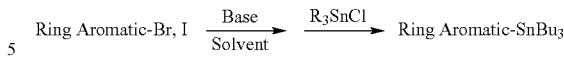

Base = n-BuLi, S-BuLi, t-BuLi
Solvent = THF, ether, DME
R = Me, Bu

Scheme Tin-03

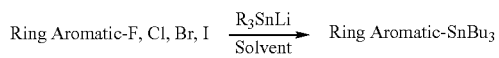

Solvent = THF, ether, DME
R = Me, Bu

Scheme Tin-04

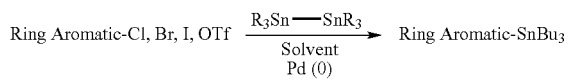

Solvent = Dioxane, Toluene
R = Me, Bu

Scheme Tin-05

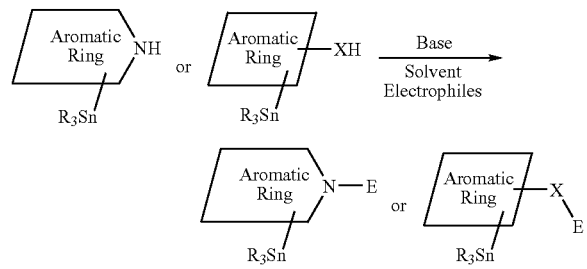

E = Electrophile = R'-halide, R'COCl, R'OCOCl,
  R'R''NCOCl, RSO$_2$Cl, R'NCO, R'NSO, R'NCNR''
Solvent = CH$_2$Cl$_2$, THF, Ether, DMF
R = Me, Bu
Base = NaH, BuLi, LDA, K$_2$CO$_3$, Et$_3$N, DBU, DMAP, NaHMDS Boronate reagents are prepared as described in reference 71. Reaction of lithium or Grignard reagents with trialkyl borates generates boronates. Alternatively, Palladium catalyzed couplings of alkoxy diboron or alkyl diboron reagents with aryl or heteroaryl halides can provide boron reagents for use in Suzuki type couplings. Some example conditions for coupling a halide with (MeO)BB(OMe)$_2$ utilize PdCl2 (dppf), KOAc, DMSO, at 80° C. until reaction is complete when followed by TLC or HPLC analysis.

Related examples are provided in the following experimental section.

Methods for direct addition of aryl or heteroaryl organometallic reagents to alpha chloro nitrogen containing heterocyles or the N-oxides of nitrogen containing heterocycles are known and applicable to the diazaindoles. Some examples are Shiotani et. Al. *J. Heterocyclic Chem.* 1997, 34(3), 901-907; Fourmigue et. al. *J. Org. Chem.* 1991, 56(16), 4858-4864.

SCHEME 15aa

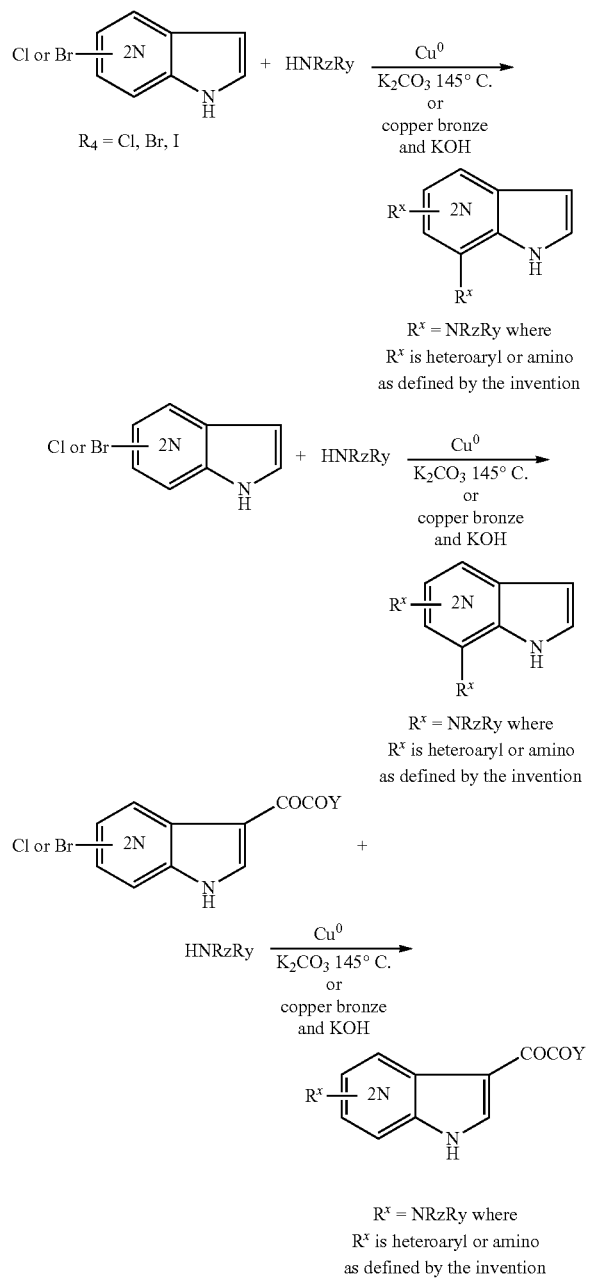

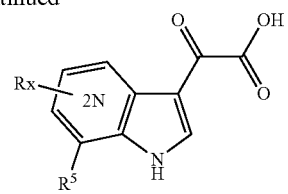

(R⁵H is a heteroaryl or amine with free N-H)

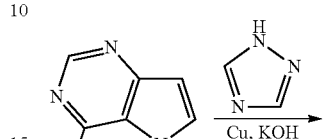

Proposed example

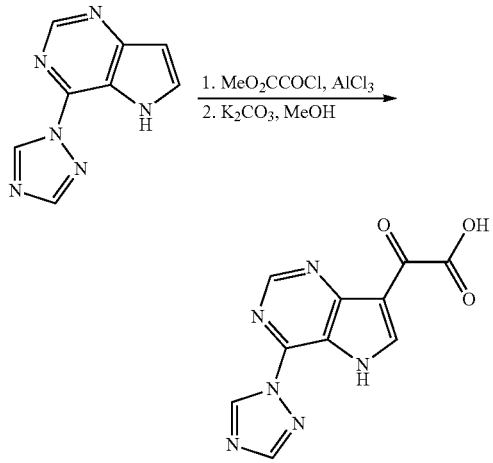

SCHEME 15bb

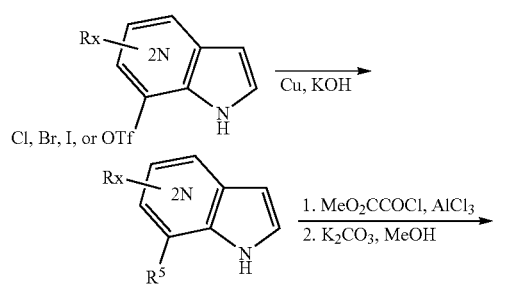

Direct displacements to install amine or N linked heteroaryl substituents could also be used to prepare compounds of Formula I. As shown in Schemes 15aa and 15bb, a mixture of halo-diazaindole intermediate, 1-2 equivalents of copper powder; 1-2 equivalents of potassium carbonate, and a 2-30 equivalents of the corresponding heterocyclic reagent, with 10 equivalents preferred; was heated at 135-160° C. for 4 to 9 hours. The reaction mixture was cooled to room temperature and filtered through filter paper. The filtrate was diluted with methanol and purified either by preparative HPLC or silica gel. In many cases no chromatography is necessary, the product can be obtained by crystallization with methanol.

Alternatively, the installation of amines or N linked heteroaryls could be carried out by heating 1 to 40 equivalents of the appropriate amine and an equivalent of the appropriate diazaindole chloride, bromide or iodide with copper bronze (from 0.1 to 10 equivalents (preferably about 2 equivalents) and from 1 to 10 equivalents of finely pulverized potassium hydroxide (preferably about 2 equivalents). Temperatures of 120° to 200° might be employed with 140-160° generally preferred. For volatile starting materials a sealed reactor may be employed. The reaction would most often be applicable when the halogen being displaced is at the 7-position of a diazaindole but the method could work when the halogen is at a different position (4-7 position possible). As shown above the reaction could be employed on diazaindoles unsubstituted at position 3 or intermediates which contain the dicarbonyl or the intact dicarbonyl piperazine urea or thioureas contained in compounds of formula I.

SCHEME 16

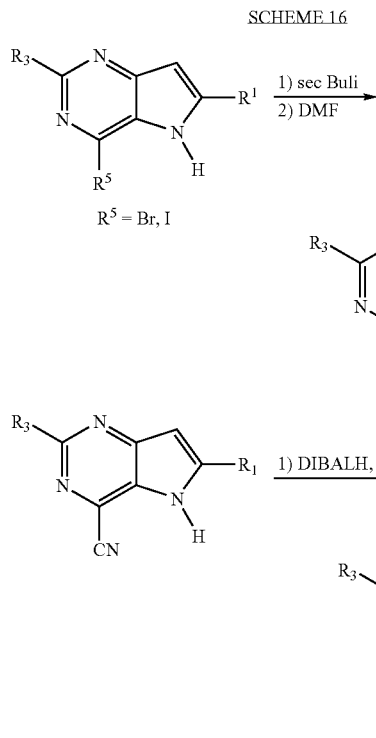

A possible preparation of a key aldehyde intermediate, 43, using a procedure adapted from the method of Gilmore et. Al. *Synlett* 1992, 79-80 is shown in Scheme 16 above. The aldehyde substituent is shown only at one position for the sake of clarity, and should not be considered as a limitation of the methodology. The bromide or iodide intermediate would be converted into an aldehyde intermediate, 43, by metal-halogen exchange and subsequent reaction with dimethylformamide in an appropriate aprotic solvent. Typical bases used could include, but would not be limited to, alkyl lithium bases such as n-butyl lithium, sec butyl lithium or tert butyl lithium or a metal such as lithium metal. A preferred aprotic solvent is THF. Typically the transmetallation would be initiated at −78° C. and allowed to react with dimethylformamide (allowing the reaction to warm may be required to enable complete reaction) to provide an aldehyde which is elaborated to compounds of Formula I. Other methods for introduction of an aldehyde group to form intermediates of formula 43 include transition metal catalyzed carbonylation reactions of suitable bromo, trifluoromethane sulfonyl, or stannyl diazaindoles.

As shown in Scheme 52, the pieces HW-$R^{18}$ can be prepared by a number of different methods. One useful way is by reacting a mono protected piperazine with a heteroaryl chloride, bromide, iodide, or triflate. This reaction is typically carried out at elevated temperature (50 to 250 degrees celsius) in a solvent such as ethylene glycol, DME, dioxane, NMP, or DMF. A tertiary amine base such as triethyl amide or diisopropyl ethyl amine is typically employed and usually 2 to 4 equivalents are employed. At least 2 equivalents are used if a salt of HW $R^{18}$ is utilized. The piperazine is typically monoprotected with a BOC group since this material is commercially available. Removal of the Boc group is typically done using HCl (typically 1 to 6N) in dioxane to provide the HCl salt. TFA may also be used to generate the TFA salt. Alternatively, the conditions for coupling heterocycles using copper catalysis discussed earlier in Scheme 12 may be used to couple W to $R^{18}$ via displacement of X in X—$R^{18}$. Alternatively Palladium catalysis in the presence of a bidentate catalyst via the procedures of Buchwald or the use of a ferrocenyl catalyst via the methods of Hartwig could be used to couple the piperazine to the heteroaryl ($R^{18}$).

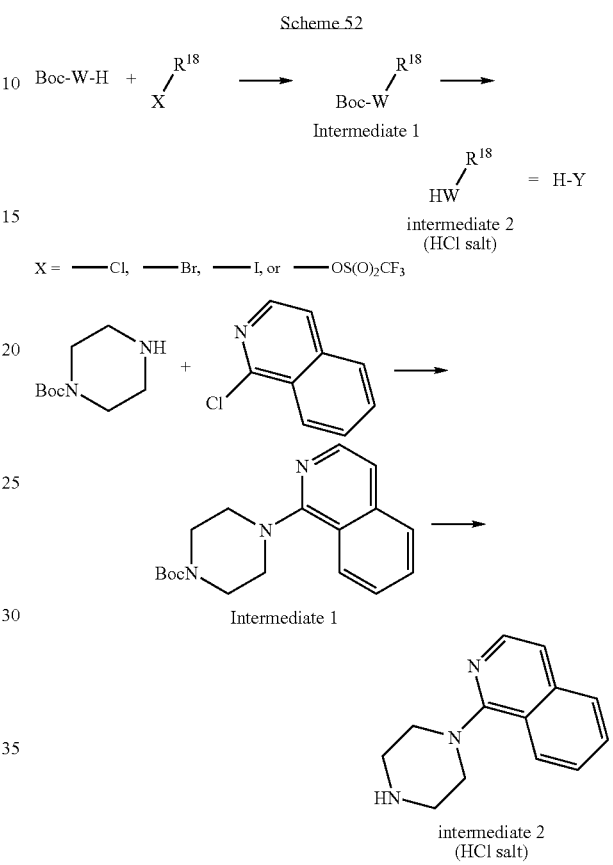

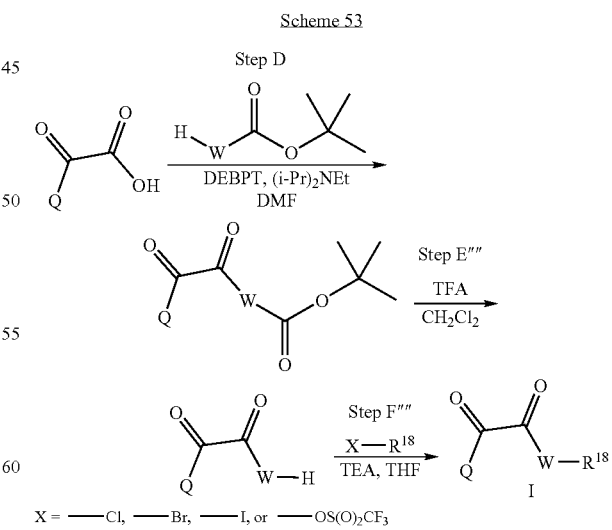

Scheme 53 describes how a protected piperazine can be coupled to Q-COOH via standard methodology. Conditions for removal of the amine protecting group which could be tBoc or other groups is protecting group specific. As shown in Scheme 53 where tBoc is the preferred protecting group used to exemplify the strategy, standard conditions for removal such as TFA in dichloromethane or alternatively aqueous HCl can provide the free amine. The free amine is coupled to heteroaromatic $R^{18}$ using the conditions described in Scheme 52 for step F"".

General Schemes:

Scheme D1 describes a possible method for preparing the compounds described by H—W where Y is as defined in the description and claims of the invention. Typically, this methodology will work best when D is a group which lowers the PKA of the hydrogens on the adjacent methylene moiety. For example cyano, sulfonyl, amido and the like as specified in the claim. A preferably could be aryl or heteroaryl moieties as described in claim 1. A could also be other groups described in claim 1. Alkoxide bases of C1 to C4 alcohols can be utilized but other bases such as lithium, sodium, or potassium dialkyl amides or the corresponding bistrimethylsilyl amides could also be utilized.

Preparation of Intermediates:

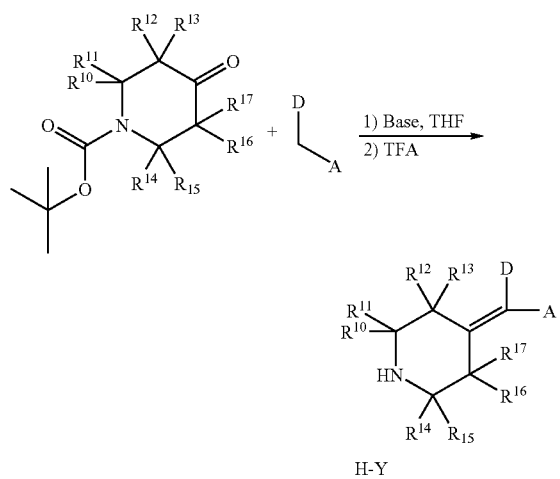

Note as shown in Scheme D1, the piperazine or piperidine moiety of Y may be substituted as defined by the invention. In the interest of clarity, unsubstituted piperidines and piperazines are used in the Schemes to keep them readable. It is understood substituents could be incorporated.

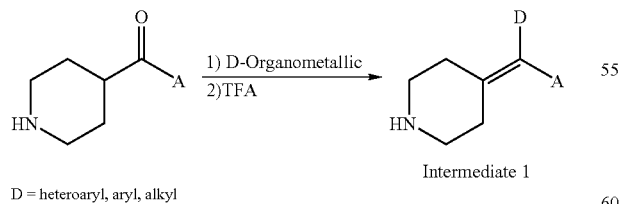

D = heteroaryl, aryl, alkyl
Organometallic = MgBr, Li, CeCl2, ZnBr

As shown in Scheme E1, addition of an organometallic reagent to a ketone can provide an intermediate tertiary alkoxide which undergoes protonation and acid catalyzed elimination to form the desired double bond. A number of organo metallic reagents could suffice as shown but an extra equivalent (at least two total) could be needed to compensate for deprotection of the amine nitrogen in many cases.

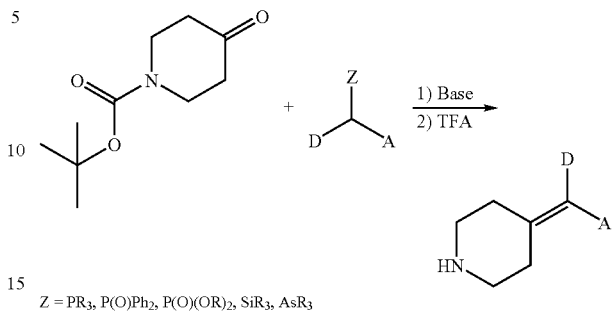

$Z = PR_3, P(O)Ph_2, P(O)(OR)_2, SiR_3, AsR_3$

Standard olefination conditions such as Wittig, Horner Emmons, Petersen or Arsenic based could be used to convert the ketone to the desired products. Some general reviews of this methodology and directions for use are contained in the following references: Wadsworth, W. S, Jr., in "Organic Reactions", Dauben, W. G., Ed., Wiley, New York, 1977, 25, 73. McMurry, J. E. Acct. Chem. Res. 1983, 16, 405. Cushman, M., et al. Bioorg. Med. Chem. 2002, 10, 2807. When Z=triphenyl phosphine, butyl lithium or LDA could be used to generate the phosphorus ylide in THF and then the ylide reacted with the ketone to provide the desired product. The phosphinate or phosphine oxide based reagents could be used with similar bases or with sodium or potassium methoxide or ethoxide in the corresponding alcohol solvents.

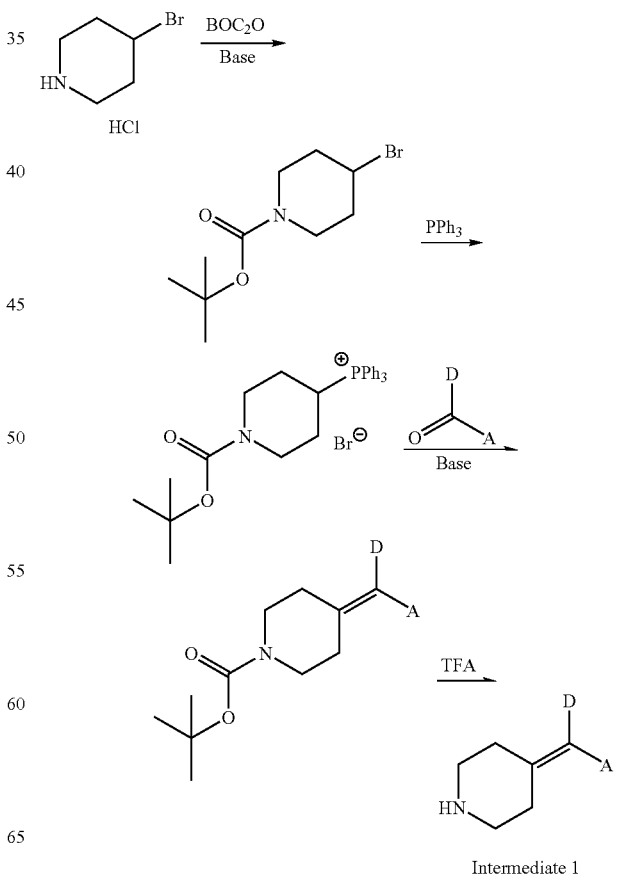

SCHEME H1

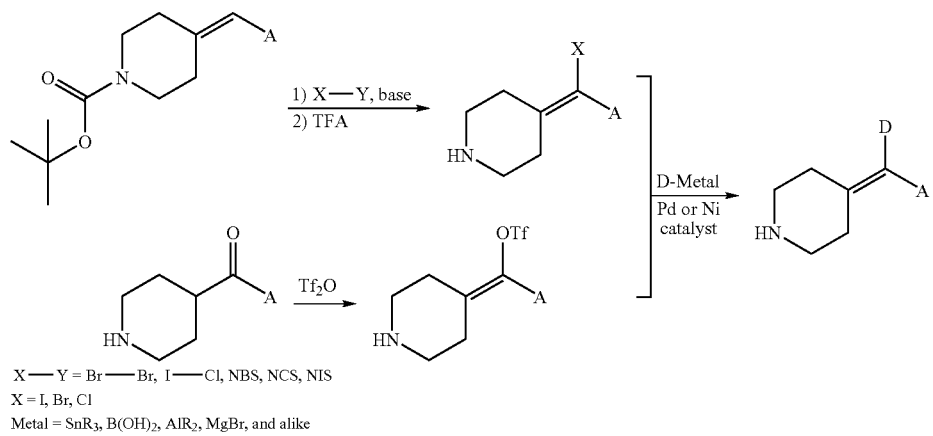

X—Y = Br—Br, I—Cl, NBS, NCS, NIS
X = I, Br, Cl
Metal = SnR₃, B(OH)₂, AlR₂, MgBr, and alike As shown above in Scheme H1, a chloride, bromide, iodide, triflate, or phosphonate undergo coupling reactions with a boronate (Suzuki type reactions). Stannanes and boronates are prepared via standard literature procedures or as described in the experimental section of this application. The vinyl bromides, chlorides, triflates, or phosphonates may undergo metal mediated coupling to provide compounds of formula W-H. Stille or Suzuki couplings are particularly useful. A detailed discussion of the references and best conditions for these kinds of metal mediated coupling is described later in this application where the discussion is combined with a description of how these types of reactions may also be used to functionalize diazaindoles.

When Ar is Benzene, Starting Materials are Commercially Available

SCHEME I1

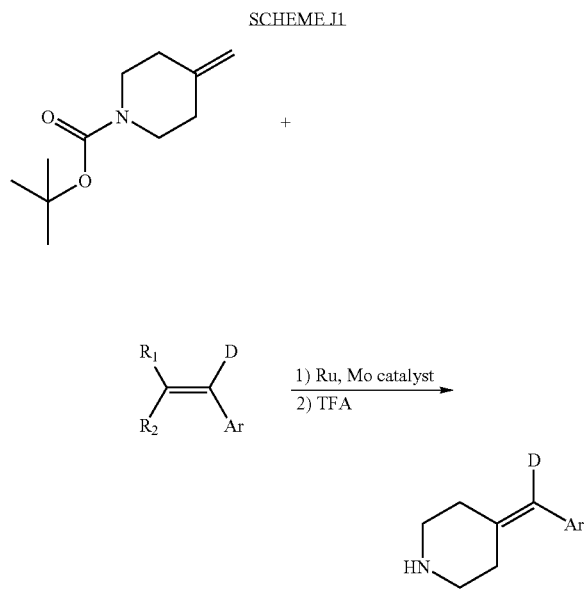

Alternatively, the compounds Y—H could potentially be prepared via olefin metathesis using highly active Rhodium catalysts. The methylene starting material can be prepared via simple Wittig methylenation of the precursor ketone which is prepared via literature methods. The olefin metathesis is preferably carried out using 1% of the imadazoylidene ruthenium benzylidene catalyst described in the following reference. The reaction is carried out starting at low temperatures (–40°) or similar. Starting methylene material is mixed with excess olefin (5 to 100 equivalents) and the reaction is warmed to ~40° C. *Synthesis of Symmetrical Trisubstituted Olefins by Cross Metathesis*. Chatterjee, Arnab K.; Sanders, Daniel P.; Grubbs, Robert H. Organic Letters ACS ASAP.

Additional references are listed below which show additional conditions and substrates which could be used with this catalyst.

*Functional group diversity by ruthenium-catalyzed olefin cross-metathesis*. Toste, F. Dean; Chatterjee, Arnab K.; Grubbs, Robert H. The Arnold and Mabel Beckman Laboratory of Chemical Synthesis, Division of Chemistry and Chemical Engineering, California Institute of Technology, Pasadena, Calif., USA. Pure and Applied Chemistry (2002), 74(1), 7-10. *A Versatile Precursor for the Synthesis of New Ruthenium Olefin Metathesis Catalysts*. Sanford, Melanie S.; Love, Jennifer A.; Grubbs, Robert H. Arnold and Mabel Beckman Laboratories for Chemical Synthesis Division of Chemistry and Chemical Engineering, California Institute of Technology, Pasadena, Calif., USA. Organometallics (2001), 20(25), 5314-5318. *Olefin metathesis with 1,1-difluoroethylene*. Trnka, Tina M.; Day, Michael W.; Grubbs, Robert H. Arnold and Mabef Beckman Lab. of Chemical Synthesis, California Institute of Technology, Pasadena, Calif., USA. Angewandte Chemie, International Edition (2001), 40(18), 3441-3444.

Scheme K1 shows a sequence in which a piperidone is converted to a monofunctionalized olefin via Wittig olefination. Bromination and dehydrobromination provides a versatile vinyl bromide intermediate. This intermediate is coupled to the QC(O)C(O)OH acid with BOPCl to provide a compound of formula I. This intermediate is then functionalized using palladium mediated couplings to either boronates or stannanes. Conditions for these couplings are described in this application.

SCHEME K1
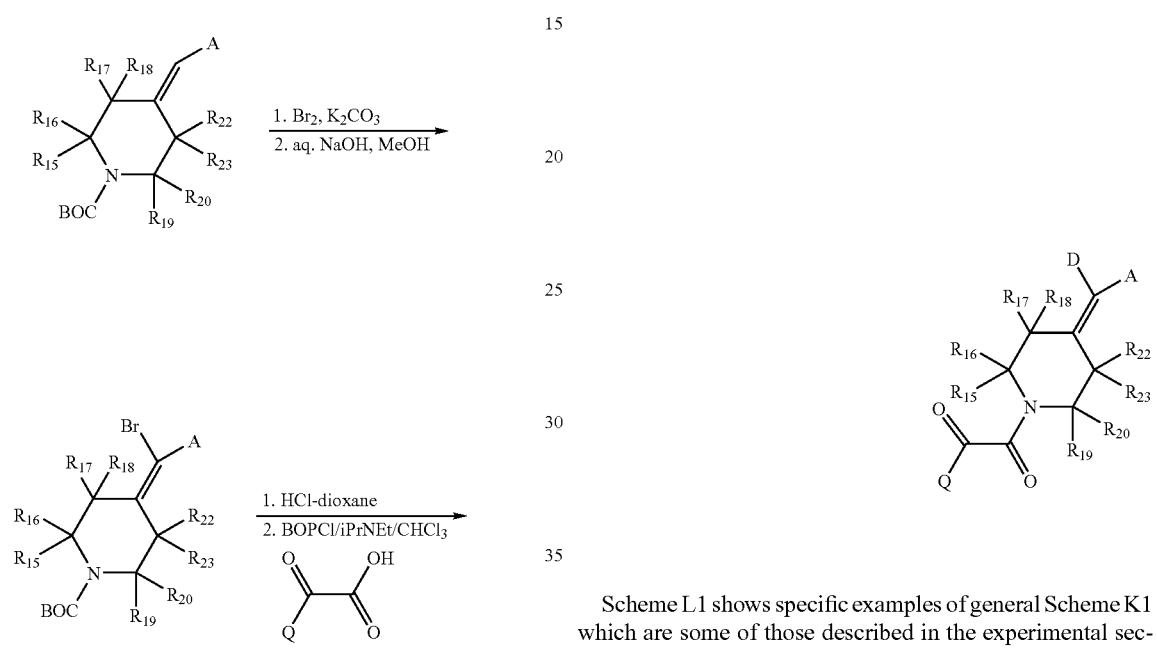
Scheme L1 shows specific examples of general Scheme K1 which are some of those described in the experimental section.
SCHEME L1
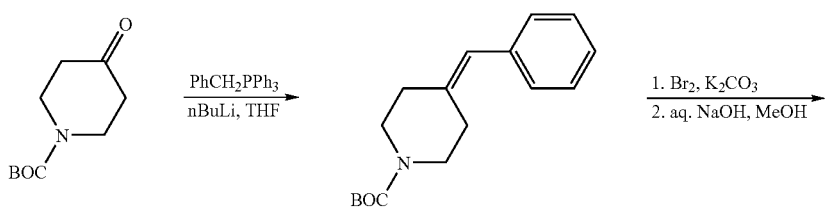
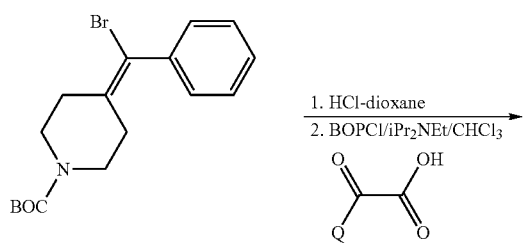

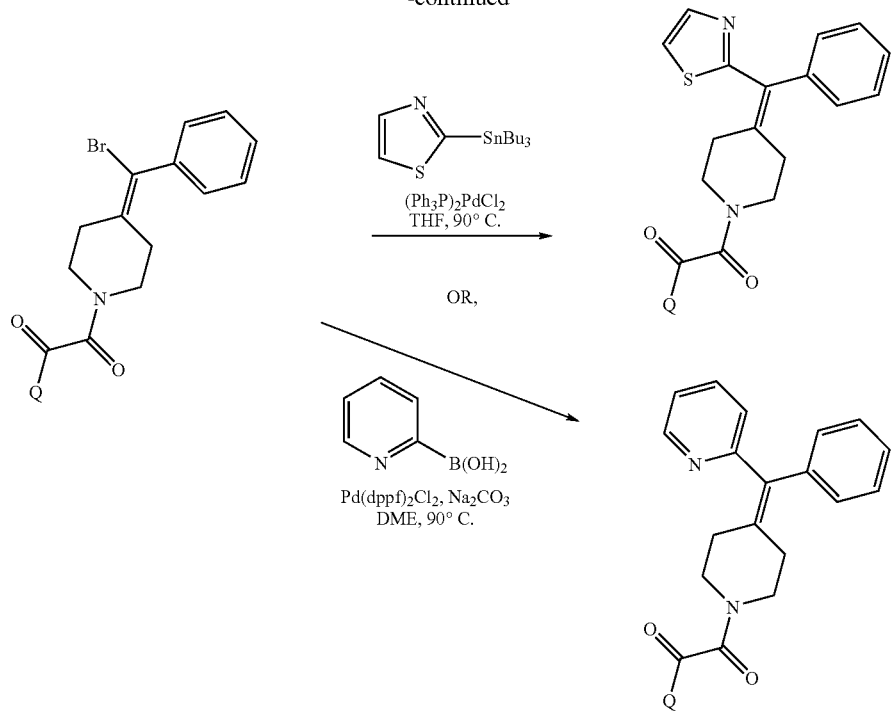

Scheme M1 shows how a protected vinyl bromide can be converted to a carboxylic acid via lithium bromide exchange and reaction with carbon dioxide. As described in this application and the incorporated ones, carboxylic acids are excellent precursors to many heterocyles or amides. The rest of Scheme M1 shows conversion to functionalized oxadiazoles. Other chemistry described in this application depicts other methods for converting acids to groups of other compounds of the invention.

SCHEME M1

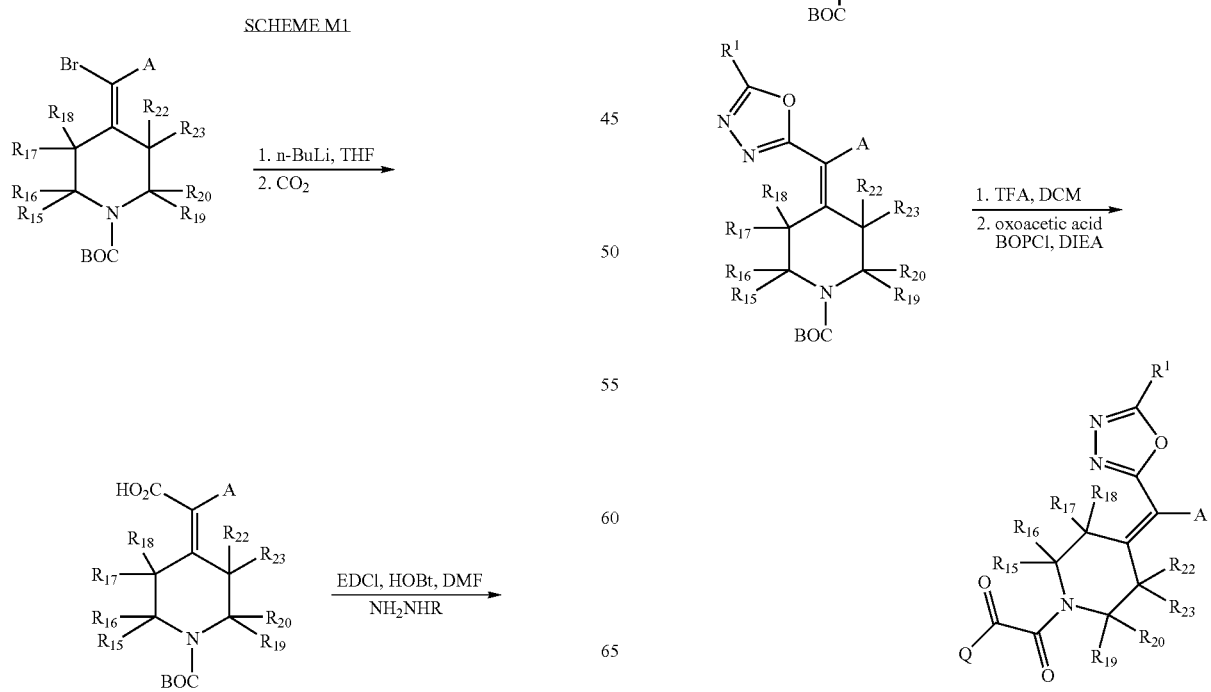

-continued
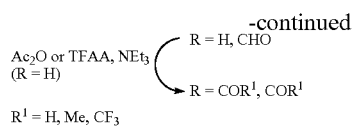
Scheme N1 depicts a more specific example of Scheme M1.
SCHEME N1
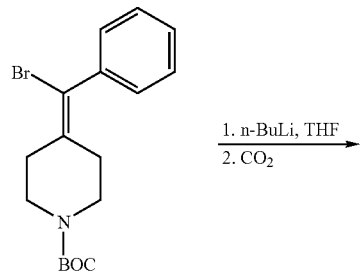
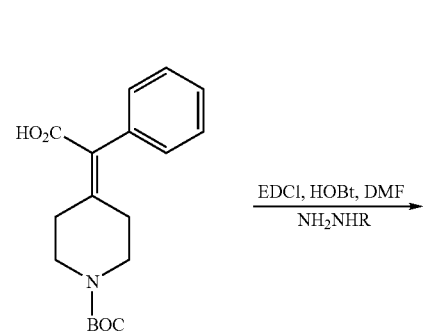
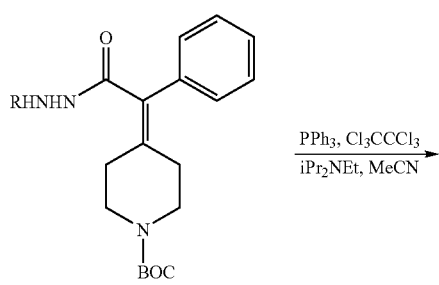
-continued
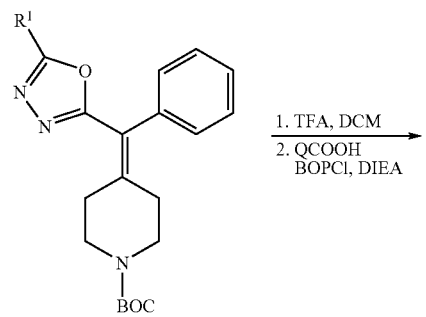
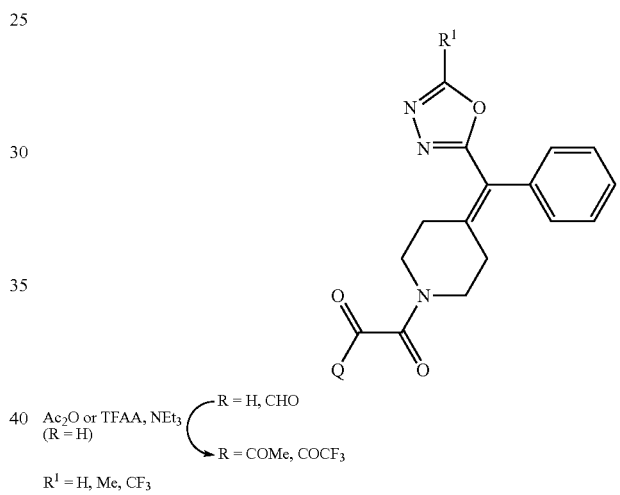
Scheme P depicts methods for functionalizing the vinyl bromide to install groups D (or A). Either a modified Stille coupling or a zinc mediated coupling are depicted. Details of these transformations are discussed later in the section on metal couplings.
SCHEME P
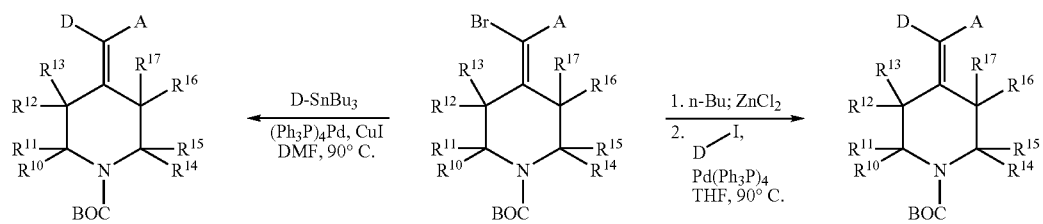

Scheme Q depicts some specific examples of Scheme P.

SCHEME Q

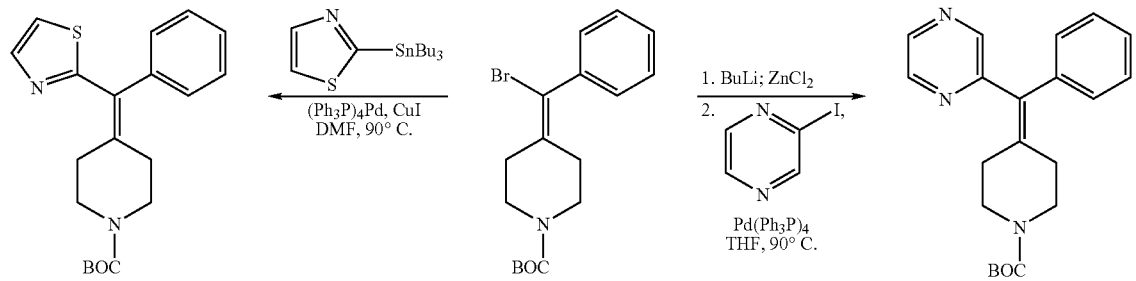

Scheme R depicts methods for functionalizing the vinyl bromide to install groups D (or A). Either a modified Stille coupling, zinc mediated coupling, or a Suzuki boronic acid coupling are depicted. A method for converting the vinyl bromide to vinyl iodide is shown. If the vinyl bromide fails to undergo efficient reaction, the more reactive iodide can be prepared as a better partner. Details of these transformations are discussed later in the section on metal couplings.

SCHEME R

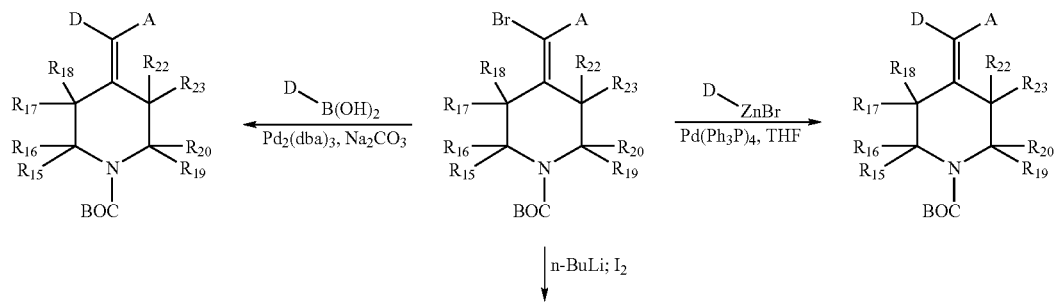

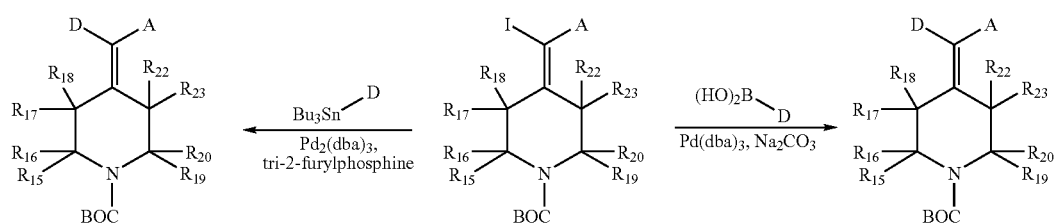

Scheme S provides specific examples of Scheme R.
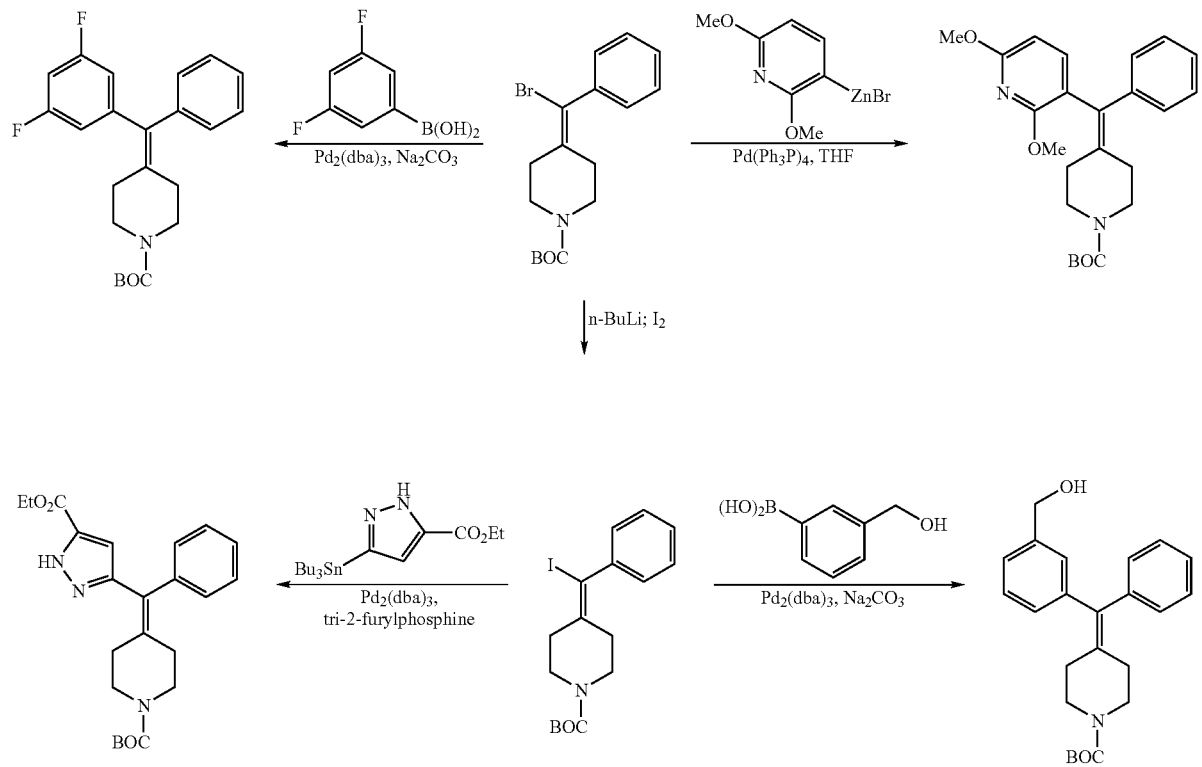
Scheme T shows methods for converting the vinyl bromide into more functionalized groups D (or A). A key aldehyde intermediate is generated from the vinyl bromide and can be used to generate heteroaryls such as the oxazole via reaction with Tosmic.
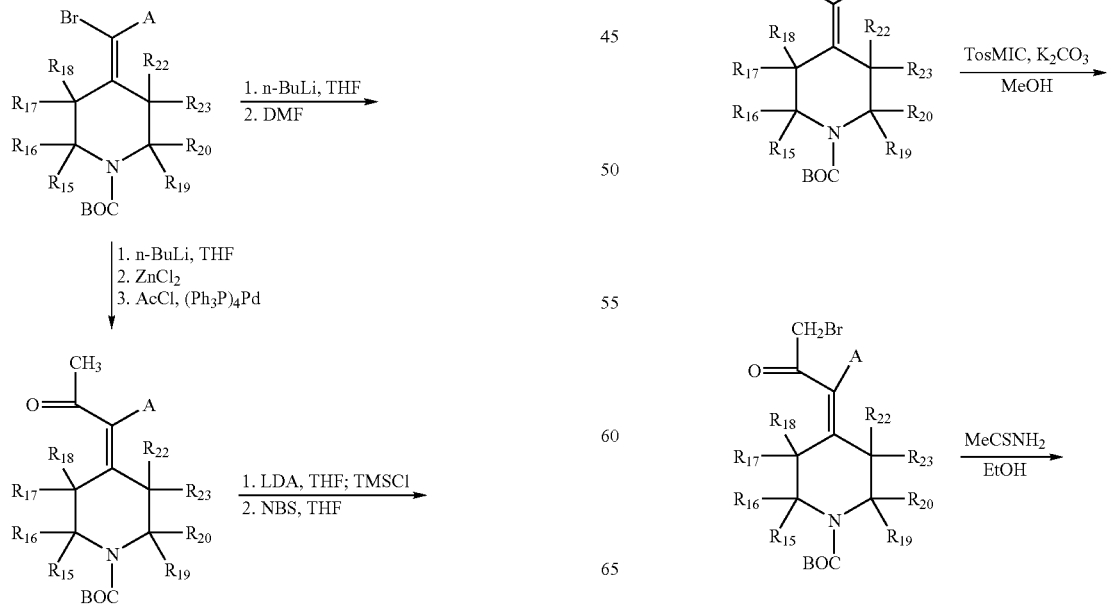

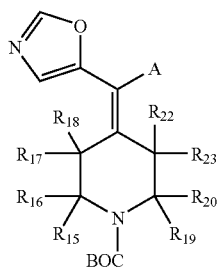
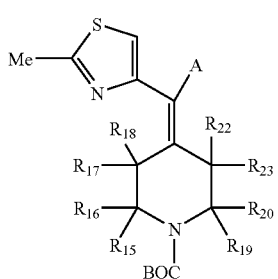
Scheme U shows how a hydrazide (generated from the acid) can be used to prepare oxadiazoles with different substituents.
SCHEME U
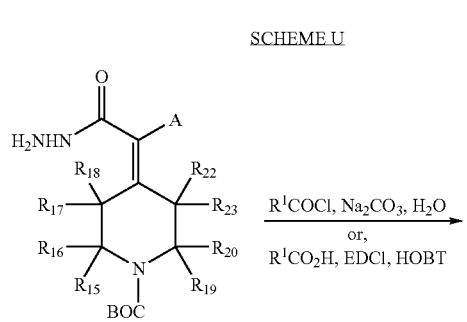
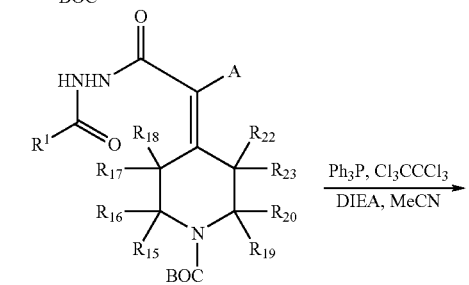
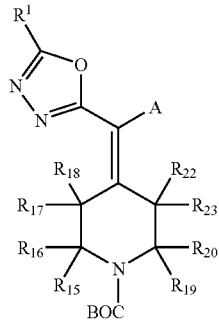
Scheme V provides more specific examples of Scheme U.
SCHEME V
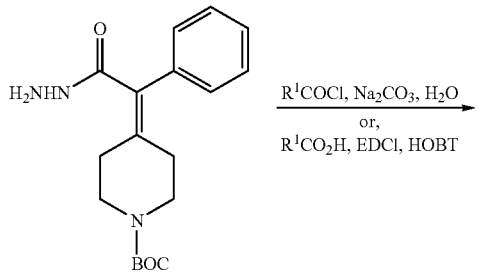
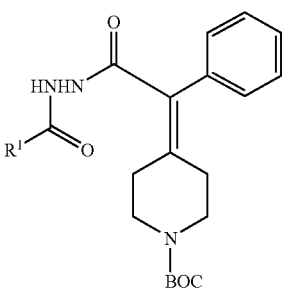
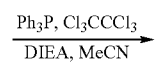
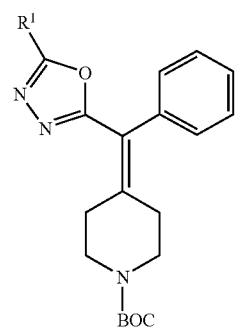

Scheme W shows some other methods for installing D (or A).
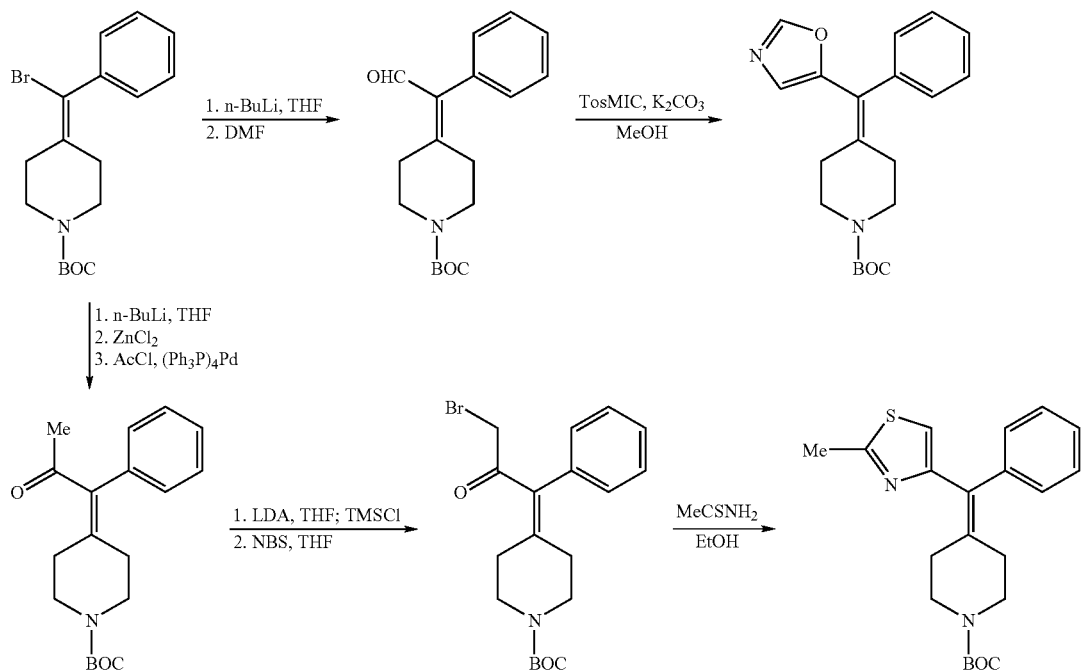
Scheme X shows a particular example where a functionalized heteroaryl or in this case aryl are coupled and then further functionalization can occur (in this case reduction of an ester to an alcohol).
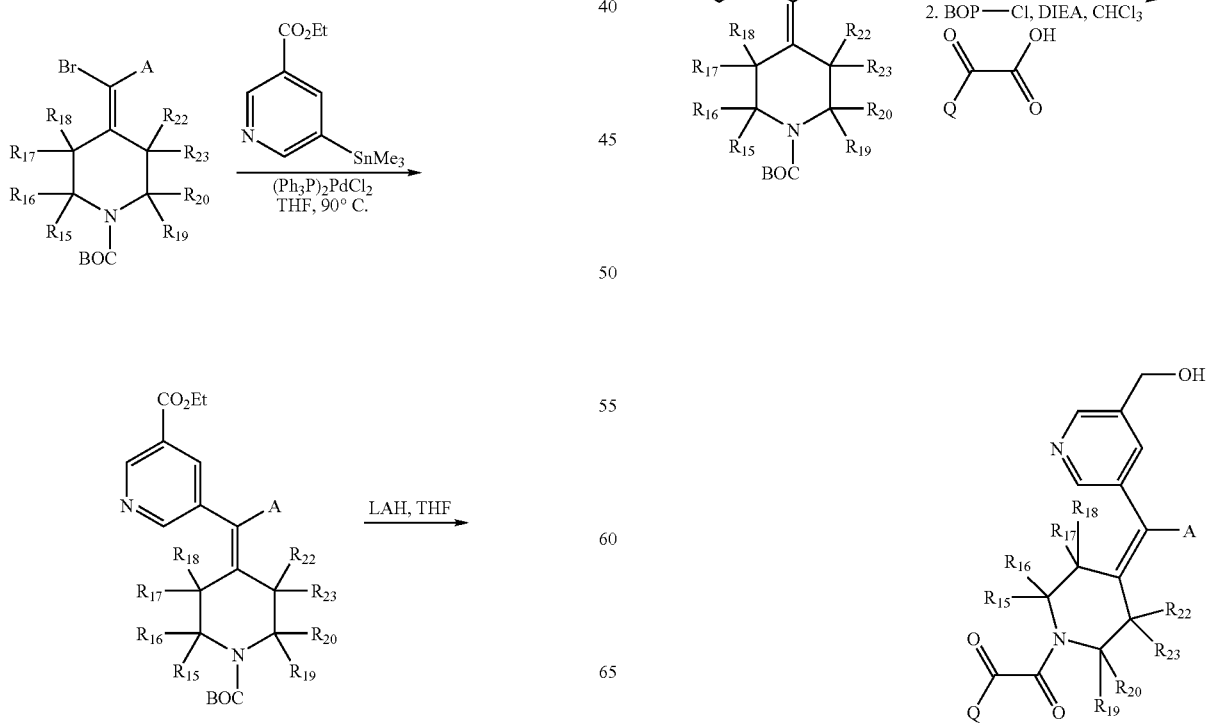

Scheme Y provides more specific examples of Scheme X.

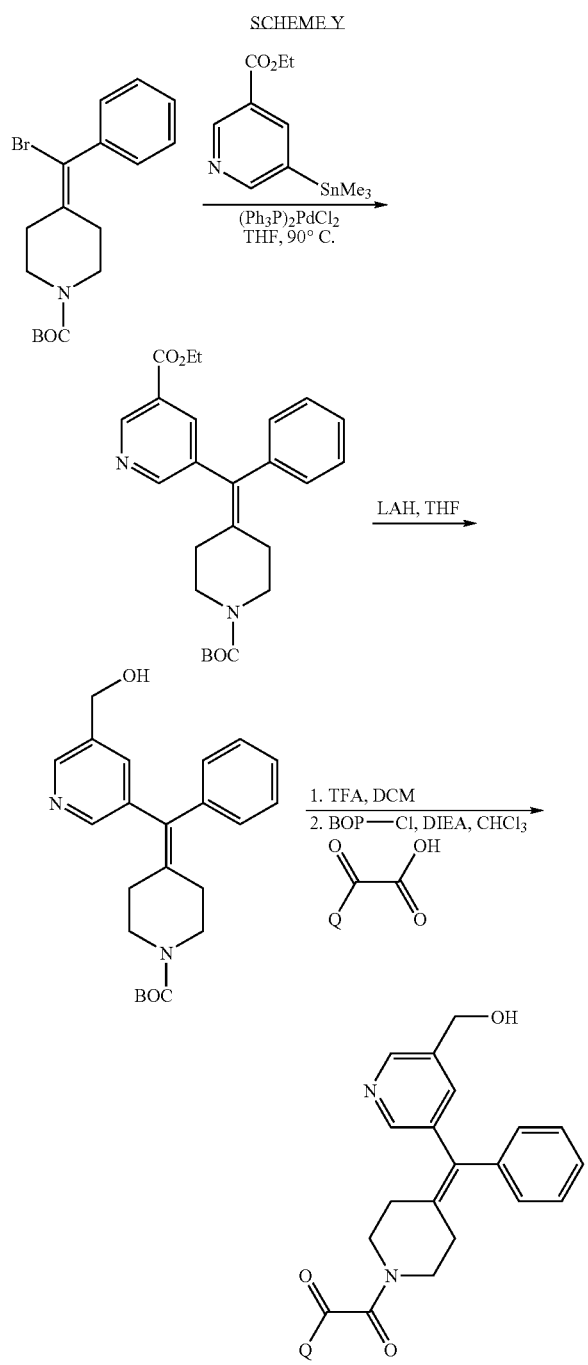

Procedures for coupling piperazine amides to oxoacetyl derivatives are described in the Blair, Wang, Wallace, or Wang references 93-95 and 106 respectively. In addition, these applications describe preparations of heteroaryls and methods for functionalizing heteroaromatic systems in the presence of oxoacetyl amides. The entire disclosures in U.S. Pat. No. 6,469,006 granted Oct. 22, 2002; U.S. Pat. No. 6,476,034 granted Nov. 5, 2002; U.S. patent application Ser. No. 10/027,612 filed Dec. 19, 2001, which is a continuation-in-part of U.S. Ser. No. 09/888,686 filed Jun. 25, 2001 (corresponding to PCT WO 02/04440, published Jan. 17, 2002); and U.S. patent application Ser. No. 10/214,982 filed Aug. 7, 2002, which is a continuation-in-part of U.S. Ser. No. 10/038,306 filed Jan. 2, 2002 (corresponding to PCT WO 02/62423 published Aug. 15, 2002) are incorporated by reference herein. The procedures used to couple diazaindole oxoacetic acids to piperazine amides in these references could potentially be used analogously to form the compounds of this invention except the H—Y are used in place of the piperazine benzamides.

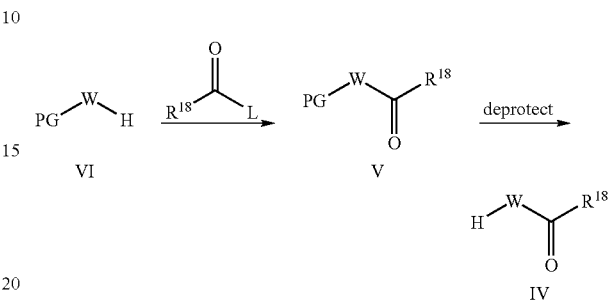

Scheme 54a depict a general method suitable for the synthesis of many of the compounds of formula I. As shown in these schemes, a suitable protected piperazine derivative, PG-YH, of Formula VI, (wherein PG is an appropriate amine protecting group) is acylated with an appropriate acylating agent, $R^{18}C(O)L$, (wherein L is a suitable leaving group) to provide the protected acylated piperazine derivative of Formula V. Compound V is then deprotected using standard methods to provide the acylated piperazine derivative of Formula IV. For example, when PG represents tertiary-butoxycarbonyl the compound of Formula V can be deprotected to provide a compound of Formula IV by treatment with a strong acid, such as neat cold trifluoroacetic acid or aqueous hydrochloric acid, in an appropriate solvent such as dichloromethane. Alternatively, when PG represents benzyl the deprotection may be effected by hydrogenation.

Examples containing substituted piperazines are prepared using the general procedures outlined in Schemes 55-38. Substituted piperazines are either commercially available from Aldrich, Co. or prepared according to literature procedures (Behun et al, Ref. 88(a), Scheme 31, eq. 01). Hydrogenation of alkyl substituted pyrazines under 40 to 50 psi pressure in EtOH afforded substituted piperazines. When the substituent was an ester or amide, the pyrazine systems could be partially reduced to the tetrahydropyrazine (Rossen et al, Ref. 88(b), Scheme 55, eq. $O_2$). The carbonyl substituted piperazines could be obtained under the same conditions described above by using commercially available dibenzyl piperazines (Scheme 55, eq. 03).

SCHEME 55

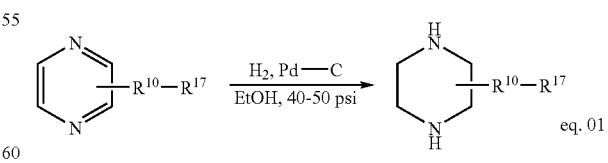

Mono-benzoylation of symmetric substituted piperazines could be achieved by using one of the following procedures (Scheme 57). (a) Treatment of a solution of piperazine in acetic acid with acetyl chloride afforded the desired monbenzoylated piperazine (Desai et al. Ref. 27, Scheme 57, eq. 04). (b) Symmetric piperazines were treated with 2 equivalents of n-butyllithium, followed by the addition of benzoyl chloride at room temperature (Wang et al, Ref. 89, Scheme 57, eq. 05).

SCHEME 57

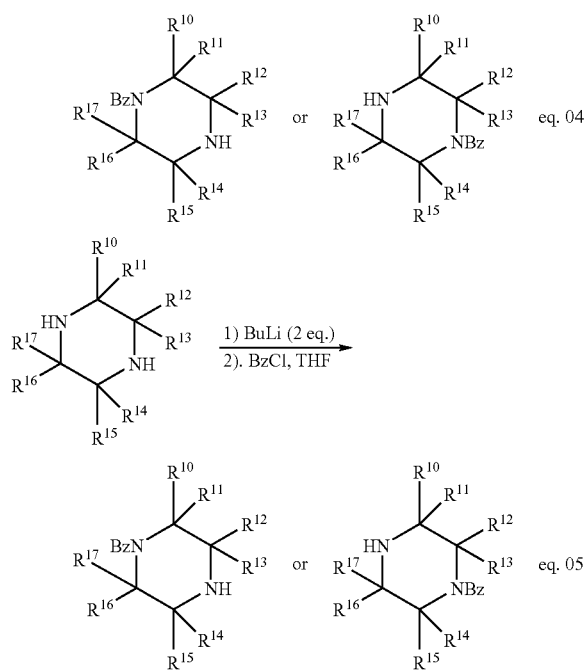

Mono-benzoylation of unsymmetric substituted piperazines could be achieved by using one of the following procedures (Scheme 57), in which all the methods were exemplified by mono-alkyl substituted piperazines. (a) Unsymmetric piperazines were treated with 2 equivalents of n-butyllithium, followed by the addition of benzoyl chloride at room temperature to afford a mixture of two regioisomers, which could be separated by chromatography (Wang et al, Ref. 89 and 90(b), Scheme 58 eq. 06); (b) Benzoic acid was converted to its pentafluorophenyl ester, and then further reaction with 2-alkylpiperazine to provide the mono-benzoylpiperazines with the benzoyl group at the less hindered nitrogen (Adamczyk et al, Ref. 90(a), Scheme 58, eq. 07); (c) A mixture of piperazine and methyl benzoate was treated with dialkylaluminum chloride in methylene chloride for 2-4 days to yield the mono-benzoylpiperazine with the benzoyl group at the less hindered nitrogen (Scheme 58 eq. 08); (d) Unsymmetric piperazines were treated with 2 equivalents of n-butyllithium, followed by subsequent addition of triethylsilyl chloride and benzoyl chloride in THF at room temperature to afford mono-benzoylpiperazines with the benzoyl group at the more hindered nitrogen (Wang et al, Ref. 90(b), Scheme 58, eq. 09).

SCHEME 58

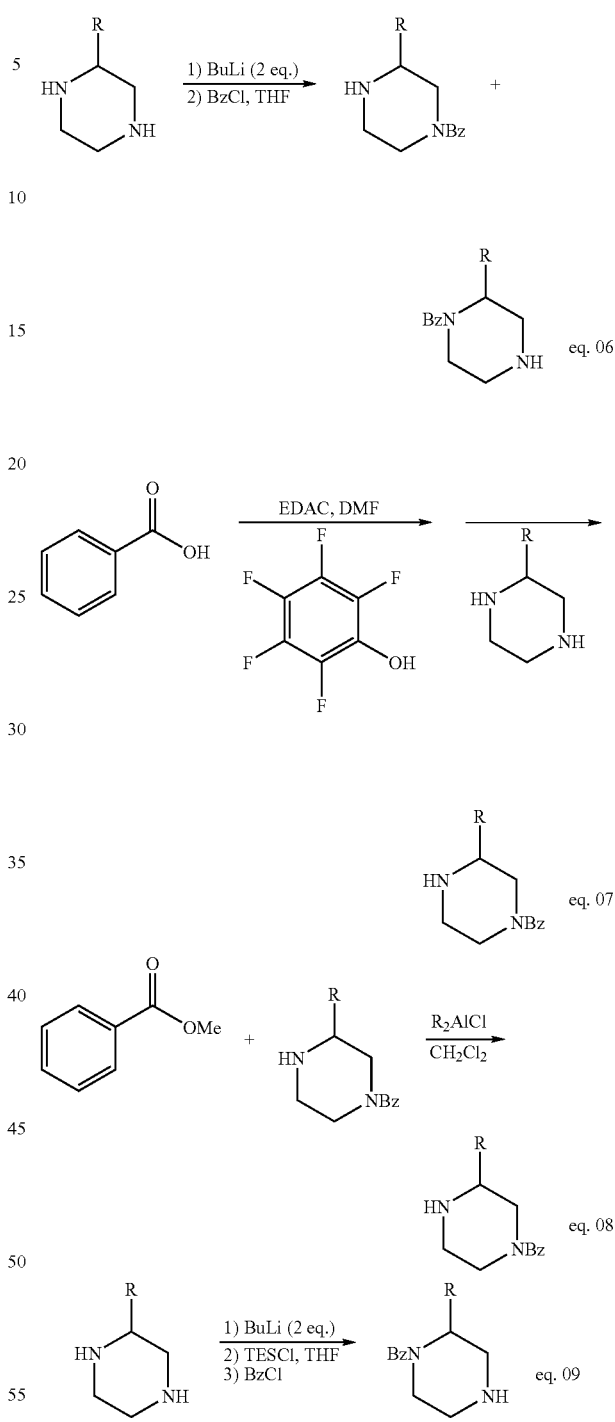

piperazine intermediates could be prepared using standard chemistry as shown in Scheme 64.

SCHEME 64

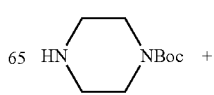

71

-continued

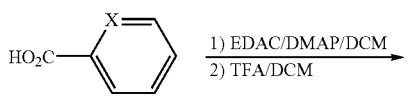

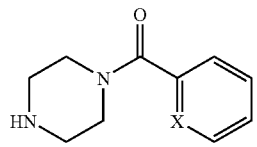

X = CH; N

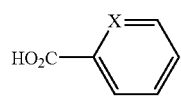

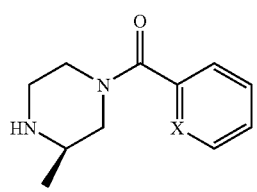

X = CH; N

SCHEME 65

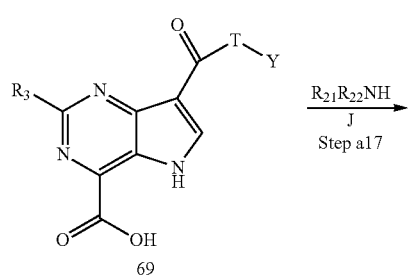

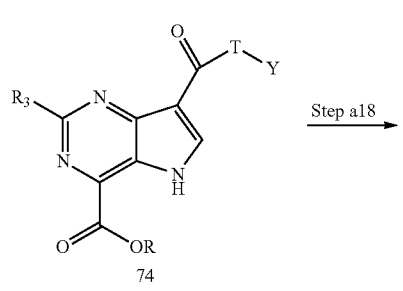

72

-continued

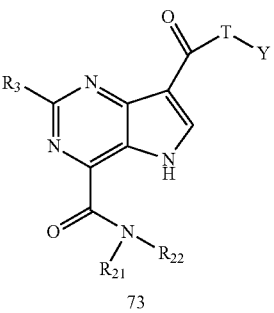

Steps a16, a17, and a18 encompasses reactions and conditions for 1°, 2° and 3° amide bond formation as shown in Schemes 65 which provide compounds such as those of Formula 73. Compounds of formula 73 represent intermediates for the preparation of Compounds I or compounds I depending on the identity of T and Y.

The reaction conditions for the formation of amide bonds encompass any reagents that generate a reactive intermediate for activation of the carboxylic acid to amide formation, for example (but not limited to), acyl halide, from carbodiimide, acyl iminium salt, symmetrical anhydrides, mixed anhydrides (including phosphonic/phosphinic mixed anhydrides), active esters (including silyl ester, methyl ester and thioester), acyl carbonate, acyl azide, acyl sulfonate and acyloxy N-phosphonium salt. The reaction of the diazaindole carboxylic acids with amines to form amides may be mediated by standard amide bond forming conditions described in the art. Some examples for amide bond formation are listed in references 41-53 but this list is not limiting. Some carboxylic acid to amine coupling reagents which are applicable are EDC, Diisopropylcarbodiimide or other carbodiimides, PyBop (benzotriazolyloxytris(dimethylamino) phosphonium hexafluorophosphate), 2-(1H-benzotriazole-1-yl)-1,1,3,3-tetramethyl uronium hexafluorophosphate (HBTU). A particularly useful method for azaindole 7-carboxylic acid to amide reactions is the use of carbonyl imidazole as the coupling reagent as described in reference 53. The temperature of this reaction may be lower than in the cited reference, from 80° C. (or possibly lower) to 150° C. or higher. An example of more specific conditions which are likely to be successful are depicted in Scheme 66.

SCHEME 66

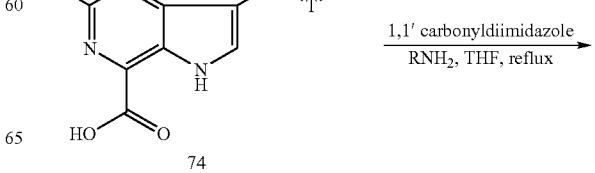

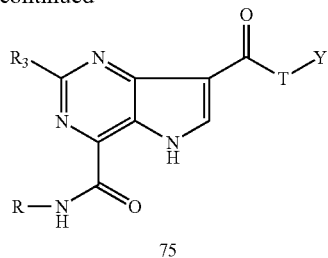

The following four general methods provide a more detailed description of procedures potentially useful for the preparation of diazindoleindolecarboxamides and these methods could potentially be employed for the synthesis of intermediates 73 useful for the preparation of compounds I or for the preparation of compounds of Formula I themselves.

Method 1:
To a mixture of an acid intermediate, such as 74, (1 equiv., 0.48 mmol), an appropriate amine (4 equiv.) and DMAP (58 mg, 0.47 mmol) dissolved $CH_2Cl_2$ (1 mL) should be added EDC (90 mg, 0.47 mmol). The resulting mixture should be shaken at rt for 12 h, and then evaporated in vacuo. The residue could be dissolved in MeOH, and subjected to preparative reverse phase HPLC purification.

Method 2:
To a mixture of an appropriate amine (4 equiv.) and HOBT (16 mg, 0.12 mmol) in THF (0.5 mL) could be added an acid intermediate, such as 74, (25 mg, 0.06 mmol) and NMM (50 µl, 0.45 mmol), followed by EDC (23 mg, 0.12 mmol). The reaction mixture could be shaken at rt for 12 h. The volatiles could be evaporated in vacuo; and the residue dissolved in MeOH and subjected to preparative reverse phase HPLC purification.

Method 3:
To a mixture of an acid intermediate, such as 74, (0.047 mmol), amine (4 equiv.) and DEPBT (prepared according to Li, H.; Jiang, X. Ye, Y.; Fan, C.; Todd, R.; Goodman, M. *Organic Letters* 1999, 1, 91; 21 mg, 0.071 mmol) in DMF (0.5 mL) could be added TEA (0.03 mL, 0.22 mmol). The resulting mixture could be shaken at rt for 12 h; and then diluted with MeOH (2 mL) and purified by preparative reverse phase HPLC.

Method 4:
A mixture of an acid intermediate, such as 74, (0.047 mmol) and 8.5 mg (0.052 mmol) of 1,1-carbonyldiimidazole in anhydrous THF (2 mL) could be heated to reflux under nitrogen. After 2.5 h, 0.052 mmol of amine could be added and heating continued. After an additional period of 3~20 h at reflux, the reaction mixture could be cooled and concentrated in vacuo. The residue could be purified by chromatography on silica gel to provide a compound of Formula I.

In addition, the carboxylic acid could be converted to an acid chloride using reagents such as thionyl chloride (neat or in an inert solvent) or oxalyl chloride in a solvent such as benzene, toluene, THF, or $CH_2Cl_2$. The amides could alternatively, be formed by reaction of the acid chloride with an excess of ammonia, primary, or secondary amine in an inert solvent such as benzene, toluene, THF, or $CH_2Cl_2$ or with stoichiometric amounts of amines in the presence of a tertiary amine such as triethylamine or a base such as pyridine or 2,6-lutidine. Alternatively, the acid chloride could be reacted with an amine under basic conditions (usually sodium or potassium hydroxide) in solvent mixtures containing water and possibly a miscible co solvent such as dioxane or THF. Scheme 25B depicts a typical preparation of an acid chloride and derivatization to an amide of Formula I. Additionally, the carboxylic acid could be converted to an ester preferably a methyl or ethyl ester and then reacted with an amine. The ester could be formed by reaction with diazomethane or alternatively trimethylsilyl diazomethane using standard conditions which are well known in the art. References and procedures for using these or other ester forming reactions can be found in reference 52 or 54.

Additional references for the formation of amides from acids are: Norman, M. H.; Navas, F. III; Thompson, J. B.; Rigdon, G. C.; *J. Med. Chem.* 1996, 39(24), 4692-4703; Hong, F.; Pang, Y.-P.; Cusack, B.; Richelson, E.; *J. Chem. Soc., Perkin Trans* 1 1997, 14, 2083-2088; Langry, K. C.; *Org. Prep. Proc. Int.* 1994, 26(4), 429-438; Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Voorman, R. L.; Reusser, F.; Althaus, I. W.; Downey, K. M.; et al.; *J. Med. Chem.* 1994, 37(7), 999-1014; Bhattacharjee, A.; Mukhopadhyay, R.; Bhattacharjya, A.; *Indian J. Chem., Sect B* 1994, 33(7), 679-682.

SCHEME 67

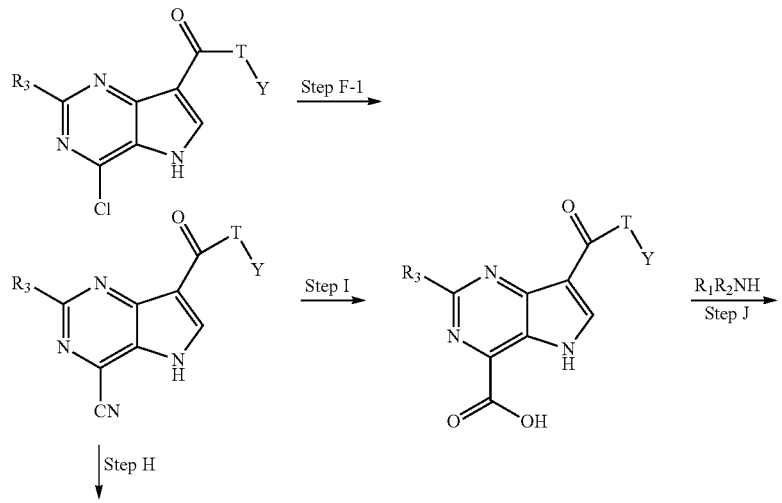

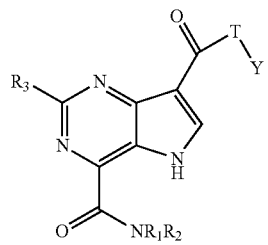

Scheme 67 shows possible synthetic transformations on a chloro diazazaindole. Step F-I of Scheme 31 could be carried out according to the following procedures: Yamaguchi, S.; Yoshida, M.; Miyajima, I.; Araki, T.; Hirai, Y.; *J. Heterocycl. Chem.* 1995, 32(5), 1517-1519 in which they use 1 eq of Chloride, 1.9 eq Cu(I)CN, in dry DMF and reflux for 48 h. The concentration of chloride in DMF is preferably 0.094 mmol per mL of solvent. Reaction times of 1-48 h may be appropriate depending on substrate and reaction temperatures between 80° C. and reflux (156° C.) may be employed. An alternate procedure for carrying out step F-1 as described in the experimental section for Example 12 occurs via reaction of the chloride intermediate with potassium cyanide (0.9 to 5 eqs, preferably 1.5 eqs) in a solvent such as DMF in the presence of catalytic sodium 4-toluene sulfinate at an elevate temperature such as 100° C. for 3 h. Reaction temperature may vary between 50 and 200° C. depending on substrate and reaction time from 30 min to 48 h. Reactions may be conducted in a sealed tube to minimize escape of volatiles if necessary.

Transformation step I, the hydrolysis of the nitrile to the acid may be carried out using acidic conditions such as MeOH and HCl at ambient temp followed by heating the intermediate immediate in the Methanol which provides the intermediate methyl ester which can then be hydrolyzed using potassium carbonate MeOH or LiOH or KOH in Methanol. This method is preferred to produce intact Compounds I. Alternatively, KOH/in ethanol or methanol may be utilized to achieve this transformation in step I. Other methods for this transformations are well known in the literature or in the references incorporated in the experimental section.

Transformation step H can be used to directly produce unsubstituted carboxamides ($R^1=R^2$=hydrogen) via stirring in cold concentrated sulfuric acid or at ambient temperature for 0.5 to 15 days. Alternatively stirring with MeOH and HCl at room temperature followed by a hydrolytic workup (water and theyl acetate or dichloromethane, may produce the same product.

Step J the amide coupling is carried out as described above in the discussions for Scheme 65 and 66.

Chemistry
General:

Additional preparations of starting materials and precursors particularly those for appending heteroaryls or carboxamides and for construction of substituted piperazines and alkenyl piperidines have been disclosed in a number different PCT and issued U.S. patents/applications (Reference 93-95, 106, 108, 109, 110, 111, 112, 113 and 114) and U.S. application Ser. No. 10/871,931 filed Jun. 18, 2004, which are hereby incorporated by reference.

All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

| LC/MS Method (compound identification) | |
|---|---|
| Column A: | YMC ODS-A S7 3.0 × 50 mm column |
| Column B: | PHX-LUNA C18 4.6 × 30 mm column |
| Column C: | XTERRA ms C18 4.6 × 30 mm column |
| Column D: | YMC ODS-A C18 4.6 × 30 mm column |
| Column E: | YMC ODS-A C18 4.6 × 33 mm column |
| Column F: | YMC C18 S5 4.6 × 50 mm column |
| Column G: | XTERRA C18 S7 3.0 × 50 mm column |
| Column H: | YMC C18 S5 4.6 × 33 mm column |
| Column I: | YMC ODS-A C18 S7 3.0 × 50 mm column |
| Column J: | XTERRA C-18 S5 4.6 × 50 mm column |
| Column K: | YMC ODS-A C18 4.6 × 33 mm column |
| Column L: | Xterra MS C18 5 uM 4.6 × 30 mm column |
| Column M: | YMC ODS-A C18 S3 4.6 × 33 mm column |
| Column N: | XTERRA MS C18 7u 3.0 × 50 mm column |
| Column O: | Phenomenex 10u 4.6 × 50 mm column |
| Column P: | Waters Atlantis 4.6 × 50 mm C18 5 um column |
| Column Q: | Phenomenex 5u 4.6 × 50 mm C18 column |
| Column R: | Phenomenex Lina C18 5 um 3.0 × 50 mm column |
| Column S: | Phenomenex C18 10u 3.0 × 50 mm column |

Standard LC Run Conditions A (Used Unless Otherwise Noted):

| | |
|---|---|
| Gradient: | 100% Solvent A/0% Solvent B to 0% Solvent A/100% Solvent B |
| Gradient time: | 2 minutes |
| Hold time: | 1 minute |
| Flow rate: | 5 mL/min |
| Detector Wavelength: | 220 nm |
| Solvent A: | 10% MeOH/90% $H_2O$/0.1% Trifluoroacetic Acid |
| Solvent B: | 10% $H_2O$/90% MeOH/0.1% Trifluoroacetic Acid |

Alternate LC Run Conditions B:

| | |
|---|---|
| Gradient: | 100% Solvent A/0% Solvent B to 0% Solvent A/100% Solvent B |
| Gradient time: | 2 minutes |
| Hold time: | 1 minute |
| Flow rate: | 5 mL/min |
| Detector Wavelength: | 220 nm |
| Solvent A: | 5% $CH_3CN$/95% $H_2O$/10 mM Ammonium Acetate |
| Solvent B: | 95% $CH_3CN$/55% $H_2O$/10 mM Ammonium Acetate |

Compounds purified by preparative HPLC were diluted in MeOH and/or DMSO (1-2 mL) and purified using the following methods on a Shimadzu LC-10A automated preparative HPLC system or on a Shimadzu LC-8A automated preparative HPLC system with detector (SPD-10AV UV-VIS) wavelength and solvent systems (A and B) the same as above.

Preparative HPLC Method (i.e., Compound Purification)

Purification Method Initial gradient (10% B, 90% A) ramp to final gradient (100% B, 0% A) over 20 minutes, hold for 3 minutes (100% B, 0% A)

| | |
|---|---|
| Solvent A: | 10% MeOH/90% H$_2$O/0.1% Trifluoroacetic Acid |
| Solvent B: | 10% H$_2$O/90% MeOH/0.1% Trifluoroacetic Acid |
| Column: | YMC C18 S5 20 × 100 mm column |
| Detector Wavelength: | 220 nm |

Starting materials, can be purchased from commercial sources or prepared using literature procedures.

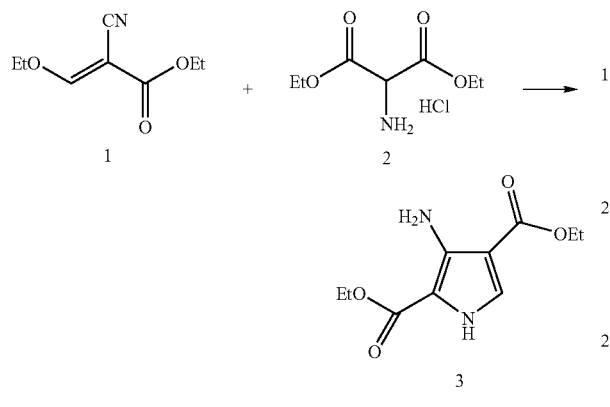

To a mixture of diethyl aminomalonate hydrochloride (8.0 g, 47.3 mmol) and ethyl (ethoxymethylene)cyanoacetate (10.0 g, 47.2 mmol) in ethanol (60 ml) at r.t. was added a 21 wt. % solution of sodium ethoxide in ethanol (62 ml, 165.4 mmol). The reaction mixture was then stirred at reflux for 20 h. After cooling to r.t., the mixture was neutralized with AcOH (6.75 ml, 118 mmol), concentrated, diluted with H$_2$O (250 mL) and extracted with CHCl$_3$ (3×250 mL). The combined organics were dried (MgSO$_4$), filtered, concentrated and purified by flushing through a pad of silical gel (100 g, EtOAc) to yield amino pyrrole 3 (10.2 g, 45.1 mmol, 95%) as a yellow solid. $^1$H NMR: (500 MHz, DMSO-d$_6$) δ 11.55 (br s, 1H), 7.21 (d, J=4.0, 1H,), 5.57 (s, 2H), 4.21 (q, J=7.5 Hz, 2H), 4.18 (q, J=7.8 Hz, 2H), 1.27 (t, J=7.5 Hz, 2H), 1.25 (t, J=7.8 Hz, 2H); LC/MS: (ES+) m/z (M-OEt)$^+$=181; HPLC R$_t$=0.96, column N.

Preparation of
4-hydroxy-5H-pyrrolo[3,2-d]pyrimidine-7-carboxylic
Acid Ethyl Ester 4

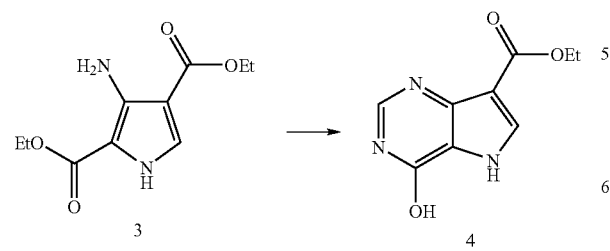

A mixture of amino pyrrole 3 (10.0 g, 44.2 mmol) and formamidine acetate (13.8 g, 133 mmol) in ethanol (100 ml) was heated at 105° C. for 20 h. The reaction mixture was filtered while still hot to collect solids that were rinsed with EtOH. The filtrate was allowed to cool to r.t., filtered to collect solids that were washed with EtOH. The combined solids were slurried with Et$_2$O, filtered and dried under vacuum to yield 4,6-diazaindole 4 (6.60 g 31.9 mmol, 72%) as a pale yellow solid which was used without further purification. $^1$H NMR: (500 MHz, DMSO-d$_6$) δ 7.91 (s, 1H), 7.89 (s, 1H), 4.22 (q, J=7.2 Hz, 2H), 3.17 (s, 2H), 1.27 (t, J=7.2 Hz, 3H); LC/MS: (ES+) m/z (M+H)$^+$=208; HPLC R$_t$=0.55 min., column N.

Preparation of
4-chloro-5H-pyrrolo[3,2-d]pyrimidine-7-carboxylic
Acid Ethyl Ester 5

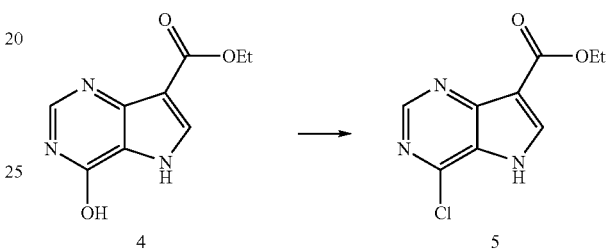

4,6-Diazaindole 4 (2.74 g, 13.2 mmol) was slurried in POCl$_3$ (37 mL, 400 mmol) and heated at 105° C. for 3.5 h. The reaction mixture was cooled, diluted with Et$_2$O (150 mL) and the resulting precipitate was collected by filtration, rinsed with EtOAc and Et$_2$O and dried under vacuum to yield 7-chloro-4,6-diazaindole 5 (2.48 g, 11.0 mmol, 83%) as a yellow powder which was used without further purification.

LC/MS: (ES+) m/z (M+H)$^+$=226; HPLC R$_t$=0.84 min., column N.

Preparation of
4-chloro-5H-pyrrolo[3,2-d]pyrimidine-7-carboxylic
Acid 6

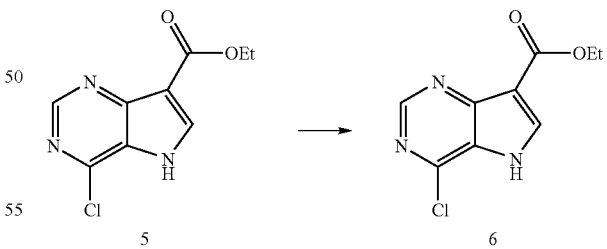

To a solution of 7-chloro-4,6-diazaindole 5 (4.0 g, 18 mmol) in THF (90 mL) was added a solution of LiOH.H$_2$O (2.5 g, 59 mmol) in H$_2$O (60 mL). The reaction mixture was stirred at 100° C. for 1 d, concentrated and recrystallized from H$_2$O (20 mL). The crystals were collected by filtration, washed with H$_2$O and dried under high vacuum. The off-white solid was shown to be the lithium salt of the diazaindole carboxylic acid 6 (quantitative), which was used without further purification. ¹H NMR: (500 MHz, DMSO-d₆) δ 8.28 (s, 1H), 8.14 (s, 1H); LC/MS: (ES+) m/z (M+H)⁺=198; HPLC R$_t$=0.47 min., column G.

Preparation of 4-chloro-5H-pyrrolo[3,2-d]pyrimidine-7-carbonyl Chloride 7

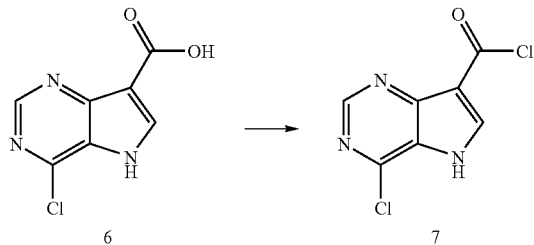

A solution of the lithium salt of the diazaindole carboxylic acid 6 (1.3 g, 6.6 mmol) in thionyl chloride (22 mL, 300 mmol) and benzene (30 mL) was heated at 105° C. for 3 h. The reaction was cooled and concentrated under vacuum. The light yellow solid residue was shown to be acid chloride 7 and was used without further purification. The acid chloride 7 was identified by quenching a small amount with methanol to make the analogous methyl ester or with aniline to make the phenyl amide, each of which could be verified by LCMS. Methyl ester: LC/MS: (ES+) m/z (M+H)⁺=212; HPLC R$_t$=0.90 min., column G. Phenyl amide: LC/MS: (ES+) m/z (M+H)⁺=269; HPLC R$_t$=01.56 min., column G.

Preparation of Example 1

2-(4-Benzoyl-piperazin-1-yl)-3-(4-chloro-5H-pyrrolo[3,2-d]pyrimidin-7-yl)-3-oxo-propionitrile (Compound 9)

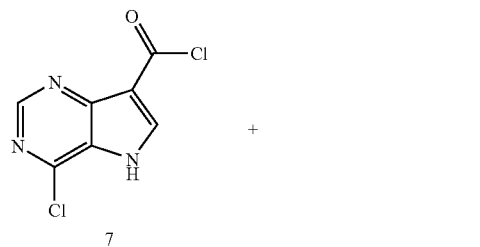

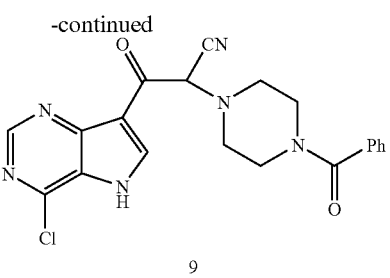

Example 1

To a solution of acid chloride 7 (0.5 mmol) and cyanomethylpiperazine 8 (150 mg, 0.66 mmol) in THF (4 mL) stirring at −35° C. was slowly added a solution of 0.5 M KHMDS in toluene (3.2 mL, 1.6 mmol). The reaction mixture was stirred at −35° C. for 1 h, quenched with sat. aqueous NaHCO₃ (50 mL) and extracted with EtOAc (2×50 mL). The combined organics were concentrated and the residue purified by prep HPLC to yield the ketocyano intermediate 9 (39 mg, 0.96 mmol, 19%) as a yellow solid. ¹H NMR: (500 MHz, DMSO-d₆) δ 8.80 (s, 0.5H), 8.80 (s, 0.5H), 8.65 (s, 0.5H), 8.64 (s, 0.5H), 7.50-7.36 (m, 5H), 4.82-4.77 (m, 1H) 3.80-3.25 (m, 4H) 3.02-2.55 (m, 4H); LC/MS: (ES+) m/z (M+H)⁺= 407; HPLC R$_t$=0.94 min., column G, conditions B.

Preparation of Example 2

1-(4-Benzoyl-piperazin-1-yl)-2-(4-chloro-5H-pyrrolo[3,2-d]pyrimidin-7-yl)-ethane-1,2-dione (Compound 10)

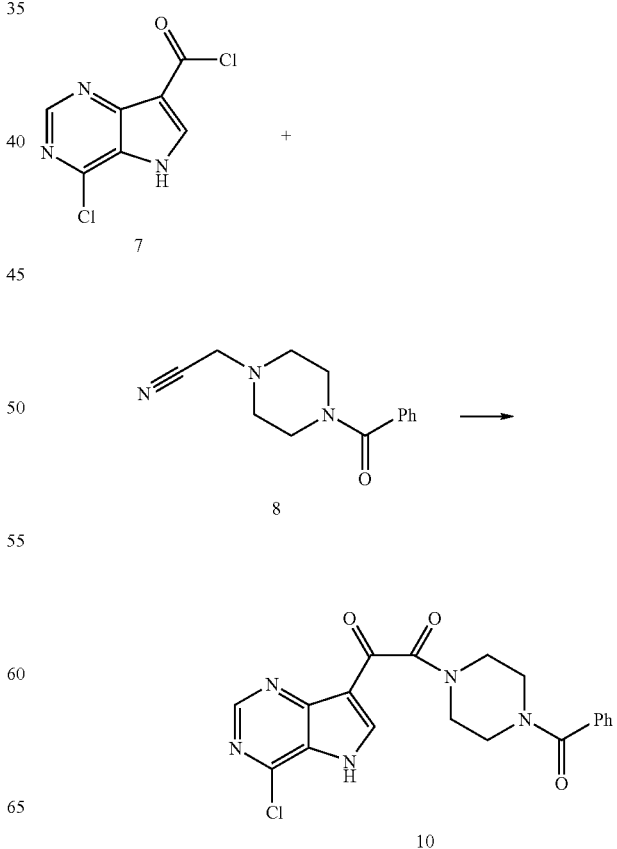

Example 2

To a solution of acid chloride 7 (6.6 mmol) and cyanomethylpiperazine 8 (1.96 g, 8.58 mmol) in THF (45 mL) stirring at −78° C. was slowly added a solution of 0.5 M KHMDS in toluene (42 mL, 21 mmol). The reaction mixture was stirred at −78° C. for 2 h and then a solution of 32 wt. % peracetic acid in dilute AcOH (12 ml, 57 mmol) was added and the reaction was stirred at r.t. for 1 h. The reaction mixture was quenched with sat. aqueous NH$_4$Cl (150 mL) and stirred with EtOAc (200 mL). The resultant precipitate was collected by filtration, rinsed with H$_2$O and EtOAc, dried under vacuum and shown to be dicarbonyl intermediate 10 (813 mg, 2.05 mmol, 24%) as an off-white solid. $^1$H NMR: (500 MHz, DMSO-d$_6$) δ 13.71 (s, 1H), 8.85 (s, 1H), 8.76 (s, 1H), 7.51-7.25 (m, 5H), 3.89-3.20 (m, 8H); LC/MS: (ES+) m/z (M+H)$^+$=398; HPLC R$_t$=0.80 min., column G, conditions B.

Preparation of Example 3

1-(4-Benzoyl-piperazin-1-yl)-2-[4-(3-methyl-pyrazol-1-yl)-5H-pyrrolo[3,2-d]pyrimidin-7-yl]-ethane-1,2-dione (Compound 11)

Example 3

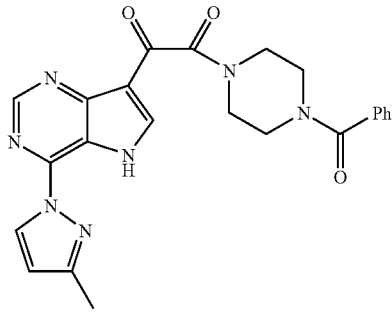

11

In a sealed tube dicarbonyl intermediate 10 (50 mg, 0.13 mmol), 3-methylpyrazole (31 mg, 0.38 mmol) and ethanol (1 mL) were combined and heated to 140° C. with microwaves for 45 min. The reaction was diluted with MeOH (2 mL), filtered and the filtrate was purified by preparative HPLC to yield 11 (36 mg, 0.08 mmol, 65%) as a light yellow solid. $^1$H NMR: (300 MHz, CD$_3$OD) δ 8.83 (s, 1H), 8.83 (d, J=2.8 Hz, 1H), 8.52 (s, 1H), 7.50-7.41 (m, 5H), 6.50 (d, J=2.8 Hz, 1H), 3.95-3.45 (m, 8H), 2.45 (s, 3H); LC/MS: (ES+) m/z (M+H)$^+$=444; HPLC R$_t$=0.97 min., column G, conditions B.

Preparation of Example 4

1-(4-Benzoyl-piperazin-1-yl)-2-[4-(4-methyl-pyrazol-1-yl)-5H-pyrrolo[3,2-d]pyrimidin-7-yl]-ethane-1,2-dione (Compound 12)

Example 4

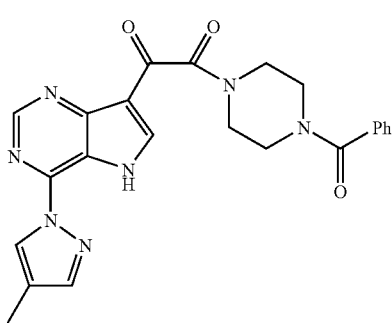

12

In a sealed tube dicarbonyl intermediate 10 (50 mg, 0.13 mmol), 4-methylpyrazole (31 mg, 0.38 mmol) and ethanol (1 mL) were combined and heated to 140° C. with microwaves for 30 min. The reaction was diluted with MeOH (2 mL), filtered and the filtrate was purified by preparative HPLC to yield 12 (34 mg, 0.08 mmol, 61%) as a white solid. $^1$H NMR: (300 MHz, CDCl$_3$) δ 12.13 (br s), 9.17 (s, 1H), 8.74 (s, 1H), 8.40 (s, 1H), 7.85 (s, 1H), 7.46-7.36 (m, 5H), 3.85-3.55 (m, 8H), 2.20 (s, 3H); LC/MS: (ES+) m/z (M+H)$^+$=444; HPLC R$_t$=0.97 min., column G, conditions B.

Preparation of Example 5

1-(4-Benzoyl-piperazin-1-yl)-2-(4-methoxy-5H-pyrrolo[3,2-d]pyrimidin-7-yl)-ethane-1,2-dione (Compound 13)

Example 5

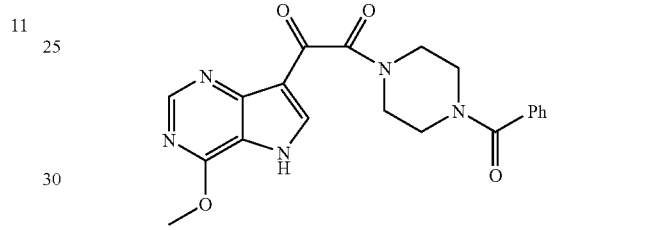

13

To a solution of dicarbonyl intermediate 10 (50 mg, 0.13 mmol) in MeOH (1 mL) was added KOMe (79 mg, 1.1 mmol). The reaction was heated at 90° C. for 0.5 h, cooled, diluted with MeOH (2 mL) and H$_2$O (1 mL) and purified by preparative HPLC to yield 13 (24 mg, 0.06 mmol, 48%) as a white solid. $^1$H NMR: (500 MHz, CD$_3$OD) δ 8.93 (s, 1H), 8.62 (s, 1H), 7.53-7.40 (m, 5H), 4.39 (s, 3H) 3.98-3.46 (m, 8H); LC/MS: (ES+) m/z (M+H)$^+$=394; HPLC R$_t$=0.79 min., column G, conditions B.

Preparation of Example 6

1-(4-Benzoyl-piperazin-1-yl)-2-(4-pyrazol-1-yl-5H-pyrrolo[3,2-d]pyrimidin-7-yl)-ethane-1,2-dione (Compound 14)

Example 6

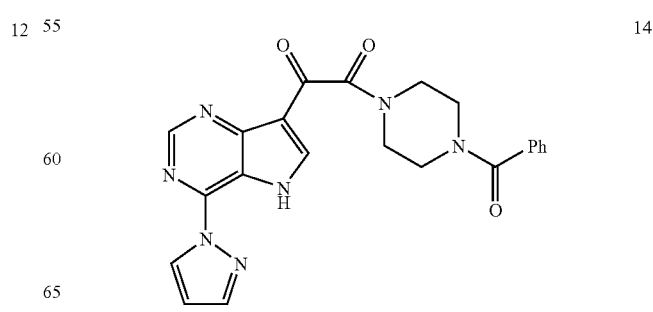

14

In a sealed tube dicarbonyl intermediate 10 (50 mg, 0.13 mmol), pyrazole (26 mg, 0.38 mmol) and ethanol (1 mL) were combined and heated at 140° C. with microwaves for 45 min. The reaction was diluted with MeOH (3 mL), filtered and the filtrate was purified by preparative HPLC to yield 14 (13 mg, 0.03 mmol, 24%) as a white solid. $^1$H NMR: (500 MHz, CD$_3$OD) δ 8.87 (s, 1H), 8.81 (s, 1H), 8.53 (s, 1H), 8.04 (s, 1H), 7.53-7.39 (m, 5H), 6.69 (s, 1H), 3.98-3.46 (m, 8H); LC/MS: (ES+) m/z (M+H)$^+$=430; HPLC R$_t$=0.95 min., column G, conditions B.

Preparation of Example 7

1-(4-Benzoyl-piperazin-1-yl)-2-[4-(3-methyl-[1,2,4] triazol-1-yl)-5H-pyrrolo[3,2-d]pyrimidin-7-yl]-ethane-1,2-dione (Compound 15)

Example 7

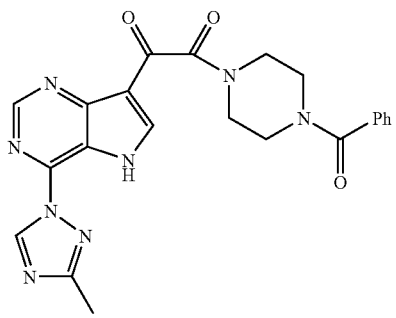

15

In a sealed tube dicarbonyl intermediate 10 (50 mg, 0.13 mmol), 3-methyl-1,2,4-triazole (22 mg, 0.38 mmol) and ethanol (1 mL) were combined and heated at 140° C. with microwaves for 45 min. The reaction was diluted with MeOH/DMF (1:1, 3 mL), filtered and the filtrate was purified by preparative HPLC to yield 15 (9 mg, 0.02 mmol, 17%) as a white solid. $^1$H NMR: (500 MHz, DMSO-d$_6$) δ 12.74 (br s, 1H), 9.54 (s, 1H), 8.94 (s, 1H), 8.54 (s, 1H), 7.55-7.35 (m, 5H), 3.90-3.22 (m, 8H), 2.53 (s, 3H); LC/MS: (ES+) m/z (M+H)$^+$=445; HPLC R$_t$=0.88 min., column G, conditions B.

Preparation of Example 8

1-(4-(2H-1,2,3-Triazol-2-yl)-5H-pyrrolo[3,2-d]pyrimidin-7-yl)-2-(4-benzoylpiperazin-1-yl)ethane-1,2-dione (Compound 16)

Example 8

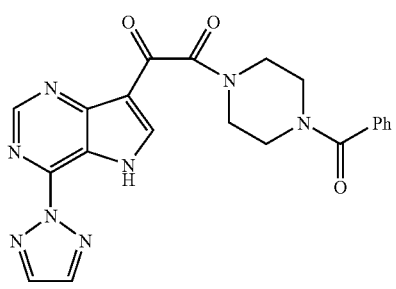

16

In a sealed tube dicarbonyl intermediate 10 (50 mg, 0.13 mmol), 3-methyl-1,2,4-triazole (52 mg, 0.75 mmol) and copper powder (16 mg, 0.25 mmol) were combined and heated at 140° C. with microwaves for 1 h. The reaction was diluted with MeOH (3 mL), filtered through celite and the filtrate was purified by preparative HPLC to yield 16 (3 mg, 0.007 mmol, 5%) as a yellow solid. $^1$H NMR: (500 MHz, CD$_3$OD) δ 8.97 (s, 1H), 8.61 (s, 1H), 8.28 (s, 1H), 8.27 (s, 1H), 7.52-7.40 (m, 5H), 4.02-3.44 (m, 8H); LC/MS: (ES+) m/z (M+H)$^+$=431; HPLC R$_t$=0.82 min., column G, conditions B.

Preparation of Example 9

1-{7-[2-(4-Benzoyl-piperazin-1-yl)-2-oxo-acetyl]-5H-pyrrolo[3,2-d]pyrimidin-4-yl}-1H-pyrazole-3-carboxylic Acid (Compound 17)

Example 9

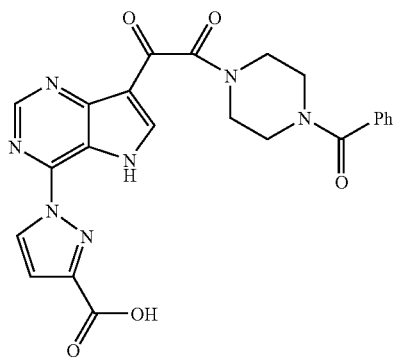

17

In a sealed tube dicarbonyl intermediate 10 (30 mg, 0.076 mmol) and 3-pyrazolecarboxylic acid (26 mg, 0.23 mmol), copper powder (10 mg, 0.16 mmol) and K$_2$CO$_3$ (52 mg, 0.38 mmol) were combined and heated at 150° C. with microwaves for 2 h. The reaction was diluted with MeOH (3 mL), filtered through celite, concentrated, dissolved into DMSO and purified by preparative HPLC to yield 17 (5 mg, 0.01 mmol, 14%) as a white solid. $^1$H NMR: (500 MHz, DMSO-d$_6$) δ 13.32 (br s, 1H), 12.55 (br s, 1H), 8.98-8.96 (m, 2H), 8.71 (s, 1H), 7.51-7.38 (m, 5H), 7.13 (d, J=2.4 Hz, 1H), 3.90-3.20 (m, 8H); LC/MS: (ES+) m/z (M+H)$^+$=474; HPLC R$_t$=0.76 min., column G, conditions B.

Preparation of Example 10

1-(4-Benzoylpiperazin-1-yl)-2-(4-ethoxy-5H-pyrrolo [3,2-d]pyrimidin-7-yl)ethane-1,2-dione (Compound 18)

Example 10

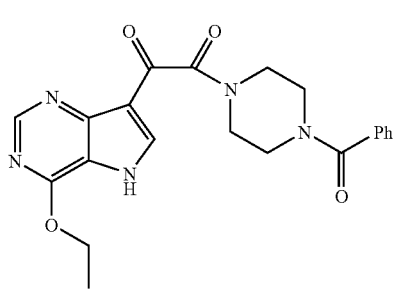

18

In a sealed tube dicarbonyl intermediate 10 (30 mg, 0.076 mmol) and 3-pyrazolecarboxylic acid (26 mg, 0.23 mmol), copper powder (10 mg, 0.16 mmol) and $K_2CO_3$ (52 mg, 0.38 mmol) in EtOH (1.0 mL) were combined and heated at 150° C. with microwaves for 2 h. The reaction was diluted with MeOH (3 mL), filtered through celite, concentrated, dissolved into DMSO and purified by preparative HPLC to yield 18 (1 mg, 0.002 mmol, 3%) as a white solid. $^1$H NMR: (500 MHz, $CD_3OD$) δ 8.73 (s, 1H), 8.45 (s, 1H), 7.57-7.40 (m, 5H), 4.77 (q, J=7.3 Hz, 2H), 4.04-3.42 (m, 8H), 1.53 (t, J=7.3 Hz, 3H); LC/MS: (ES+) m/z $(M+H)^+=408$; HPLC $R_t=0.85$ min., column G, conditions B.

Preparation of Example 11

1-(4-Acetyl-5H-pyrrolo[3,2-d]pyrimidin-7-yl)-2-(4-benzoylpiperazin-1-yl)ethane-1,2-dione (Compound 19)

Example 11

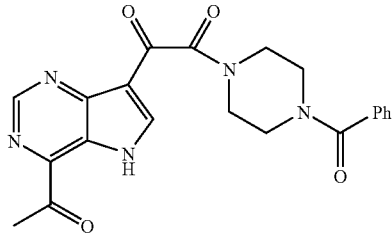

In a sealed tube dicarbonyl intermediate 10 (600 mg, 1.5 mmol), tributyl (1-ethoxyvinyl)stannane (1.5 mL 4.5 mmol), tetrakis(triphenylphosphine)palladium (0) (350 mg, 0.30 mmol) and 1,4-dioxane (15 mL) were combined and heated at 120° C. with microwaves for 2 h. The reaction mixture was divided and 25% v/v was concentrated diluted with MeOH/$CH_2Cl_2$ (2:1, 1.5 mL) and 1N aqueous HCl (0.5 mL). The reaction was stirred overnight, neutralized with 1N aqueous NaOH (0.5 mL) and concentrated. The residue was dissolved into DMSO, filtered and purified by preparative HPLC to yield 19 (79 mg, 0.20 mmol, 53%) as a pink solid. $^1$H NMR: (500 MHz, $CD_3OD$) δ 9.19 (s, 1H), 8.62 (s, 1H), 7.52-7.40 (m, 5H), 3.92-3.41 (m, 8H), 2.80 (s, 3H); LC/MS: (ES+) m/z $(M+H)^+=406$; HPLC $R_t=0.79$ min., column N.

Preparation of Example 12

7-(2-(4-Benzoylpiperazin-1-yl)-2-oxoacetyl)-5H-pyrrolo[3,2-d]pyrimidine-4-carbonitrile (Compound 20)

Example 12

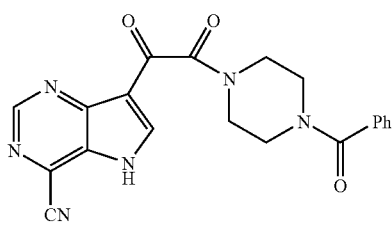

In a sealed tube dicarbonyl intermediate 10 (40 mg, 0.10 mmol), potassium cyanide (10 mg, 0.15 mmol), sodium 4-toluenesulfinate (20 mg, 0.11 mmol) and DMF (0.8 mL) were combined and heated at 100° C. for 3 h. The crude reaction mixture was partitioned between aqueous 5% $Na_2CO_3$ (0.5 mL) and EtOAc (4 mL). The organic layer was washed with aqueous 5% $Na_2CO_3$ (0.7 mL), concentrated, dissolved into MeOH/DMSO (3:1, 2 mL) and purified by preparative HPLC to yield 20 (10 mg, 0.03 mmol, 26%) as a white solid. $^1$H NMR: (500 MHz, DMSO-$d_6$) δ 14.16 (br s, 1H), 9.20 (s, 1H), 8.96 (s, 1H), 7.52-7.36 (m, 5H), 3.90-3.28 (m, 8H); LC/MS: (ES+) m/z $(M+H)^+=389$; HPLC $R_t=0.92$ min., column P, conditions B.

Preparation of Example 13

1-(7-(2-(4-Benzoylpiperazin-1-yl)-2-oxoacetyl)-5H-pyrrolo[3,2-d]pyrimidin-4-yl)-N,N-dimethyl-1H-pyrazole-3-carboxamide (Compound 21)

Example 13

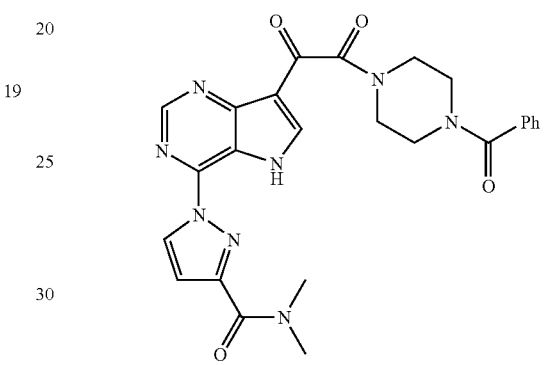

In a sealed tube dicarbonyl intermediate 10 (50 mg, 0.13 mmol), N,N-dimethyl-1H-pyrazole-3-carboxamide (53 mg, 0.38 mmol), copper(0) (10 mg) and 1,4-dioxane (0.8 mL) were combined and heated at 150° C. with microwaves for 2 h. The reaction mixture was concentrated, diluted with MeOH and DMSO, filtered and purified by preparative HPLC to yield 21 (2.3 mg, 0.005 mmol, 4%) as a yellow solid. $^1$H NMR: (500 MHz, $CD_3OD$) δ 8.94-8.87 (m, 2H), 8.59 (s, 1H), 7.56-7.36 (m, 5H), 6.94 (d, J=2.8 Hz, 1H), 4.07-3.43 (m, 8H), 3.29 (s, 3H), 3.19 (s, 3H); LC/MS: (ES+) m/z $(M+H)^+=501$; HPLC $R_t=1.16$ min., column N.

Preparation of Example 14

1-(4-Benzoylpiperazin-1-yl)-2-(4-(3-(1-methylpiperazine-4-carbonyl)-1H-pyrazol-1-yl)-5H-pyrrolo[3,2-d]pyrimidin-7-yl)ethane-1,2-dione (Compound 22)

Example 14

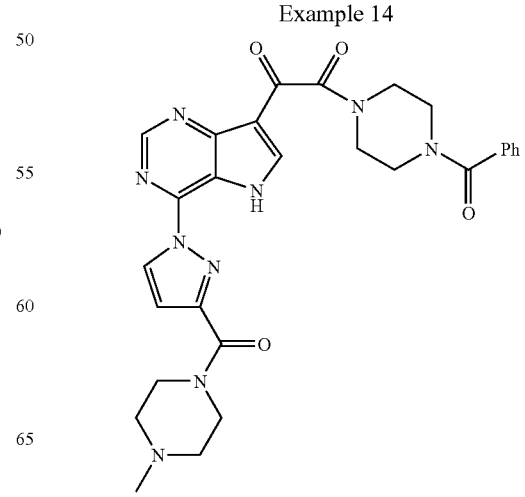

Carboxylic acid 17 (34 mg, 0.73 mmol), N-methylpiperazine (15 mg, 0.15 mmol), N,N-diisopropylethylamine (0.13 mL, 94 mg, 0.73 mmol) and bis(2-oxo-3-oaxzolidinyl)phosphinic chloride (41 mg, 0.16 mmol) were dissolved into $CH_2Cl_2$ (0.5 mL) and stirred for 20 h. The reaction mixture was concentrated, diluted with MeOH (1.7 mL) filtered and purified by preparative HPLC to yield 22 (41 mg, 0.73 mmol, 99%) as a white solid $^1$H NMR: (500 MHz, $CD_3OD$) δ 8.93 (d, J=2.8 Hz, 1H), 8.90 (s, 1H), 8.60 (s, 1H), 7.54-7.37 (m, 5H), 6.98 (d, J=2.8 Hz, 1H), 4.06-3.12 (m, 16H), 2.97 (s, 3H); LC/MS: (ES+) m/z (M+H)$^+$=556; HPLC $R_t$=1.03 min., column P., conditions B.

Preparation of Example 15

1-(4-Benzoylpiperazin-1-yl)-2-(4-(3-phenyl-1H-pyrazol-1-yl)-5H-pyrrolo[3,2-d]pyrimidin-7-yl)ethane-1,2-dione (Compound 23)

Example 15

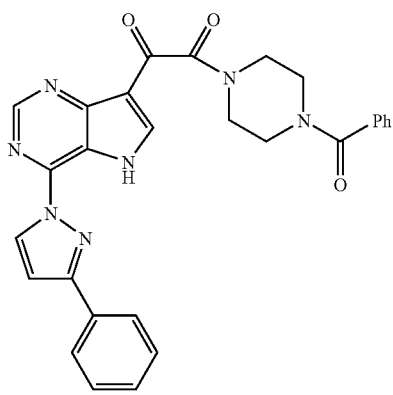

In a sealed tube dicarbonyl intermediate 10 (50 mg, 0.13 mmol), 3-phenyl-1H-pyrazole (80 mg, 0.56 mmol) and 1,4-dioxane (2.5 mL) were combined and heated at 170° C. with microwaves for 20 min. The reaction was concentrated and triturated with MeOH (3 mL). The resulting solids were washed with MeOH and with $Et_2O$ to yield 23 (33 mg, 0.07 mmol, 50%) as a tan solid. $^1$H NMR: (500 MHz, DMSO-$d_6$) δ 12.42 (br s, 1H), 8.95 (d, J=2.8 Hz, 1H), 8.92 (s, 1H), 8.57 (br d, J=3.1 Hz, 1H), 8.27 (d, J=7.3 Hz, 2H), 7.55 (dd, J=7.3, 7.3 Hz, 2H), 7.48 (t, J=7.3 Hz, 1H), 7.51-7.38 (m, 5H), 7.30 (d, J=2.8 Hz, 1H), 3.92-3.21 (m, 8H); LC/MS: (ES+) m/z (M+H)$^+$=505; HPLC $R_t$=1.40 min., column Q, conditions B.

Preparation of Example 16

1-(4-Benzoylpiperazin-1-yl)-2-(4-(3-(4-fluorophenyl)-1H-pyrazol-1-yl)-5H-pyrrolo[3,2-d]pyrimidin-7-yl)ethane-1,2-dione (Compound 24)

Example 16

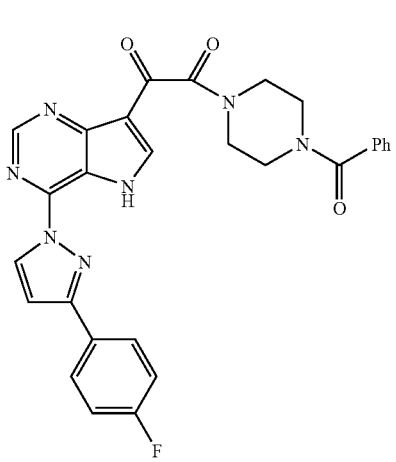

In a sealed tube dicarbonyl intermediate 10 (50 mg, 0.13 mmol), 3-(4-fluorophenyl)-1H-pyrazole (150 mg, 0.93 mmol) and 1,4-dioxane (2 mL) were combined and heated at 160° C. with microwaves for 20 min. The reaction was concentrated, diluted with MeOH (3 mL), neutralized with saturated aqueous $NaHCO_3$ and 24 (15 mg, 0.03 mmol, 22%) was collected by filtration as a tan solid. $^1$H NMR: (500 MHz, DMSO-$d_6$) δ 12.48 (br s, 1H), 8.96 (d, J=2.8 Hz, 1H), 8.91 (s, 1H), 8.58 (br s, 1H), 8.34 (dd, J=8.7, 5.6 Hz, 2H), 7.50-7.39 (m, 5H), 7.88 (t, J=8.7 Hz, 2H), 7.80 (d, J=2.8 Hz, 1H), 3.91-3.23 (m, 8H); LC/MS: (ES+) m/z (M+H)⁺=524; HPLC R$_t$=1.42 min., column Q, conditions B.

Preparation of Example 17

1-(4-Benzoylpiperazin-1-yl)-2-(4-(3-(4-methoxyphenyl)-1H-pyrazol-1-yl)-5H-pyrrolo[3,2-d]pyrimidin-7-yl)ethane-1,2-dione (Compound 25)

Example 17

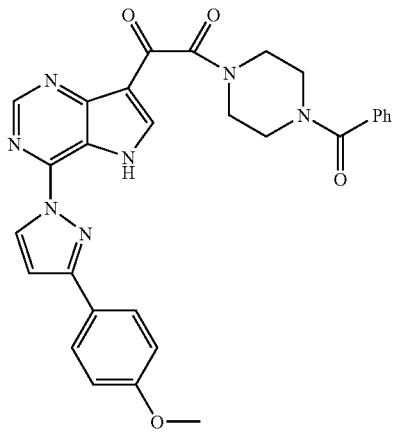

In a sealed tube dicarbonyl intermediate 10 (50 mg, 0.13 mmol), 3-(4-methoxyphenyl)-1H-pyrazole (105 mg, 0.60 mmol) and 1,4-dioxane (2.5 mL) were combined and heated at 170° C. with microwaves for 20 min. The reaction was concentrated and triturated with MeOH (3 mL). The resulting solids were washed with MeOH and with Et$_2$O to yield 25 (43 mg, 0.08 mmol, 61%) as a tan solid. ¹H NMR: (500 MHz, DMSO-d$_6$) δ 12.41 (br s, 1H), 8.91 (d, J=2.8 Hz, 1H), 8.89 (s, 1H), 8.55 (br d, J=3.4 Hz, 1H), 8.20 (d, J=8.7 Hz, 2H), 7.51-7.39 (m, 5H), 7.23 (d, J=2.8 Hz, 1H), 7.08 (d, J=8.7 Hz, 2H), 3.85 (s, 3H), 3.92-3.21 (m, 8H); LC/MS: (ES+) m/z (M+H)⁺=535; HPLC R$_t$=1.40 min., column Q, conditions B.

Preparation of Example 18

1-(4-Benzoylpiperazin-1-yl)-2-(4-(3-(2-methoxyphenyl)-1H-pyrazol-1-yl)-5H-pyrrolo[3,2-d]pyrimidin-7-yl)ethane-1,2-dione (Compound 26)

Example 18

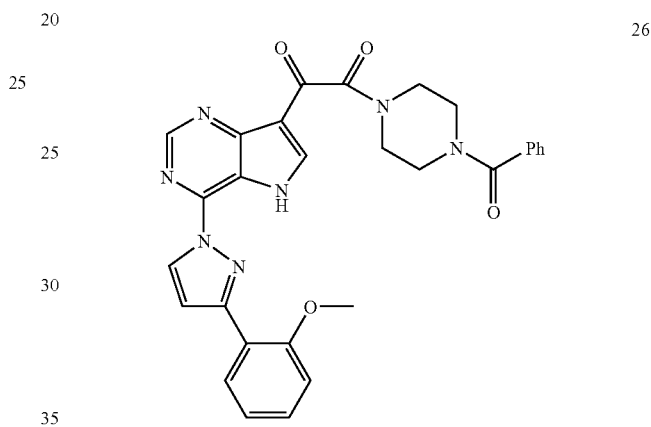

In a sealed tube dicarbonyl intermediate 10 (51 mg, 0.13 mmol), 3-(2-methoxyphenyl)-1H-pyrazole (109 mg, 0.60 mmol) and 1,4-dioxane (2 mL) were combined and heated at 170° C. with microwaves for 20 min. The reaction was concentrated and triturated with MeOH (3 mL). The resulting solids were washed with MeOH and with Et$_2$O to yield 26 (32 mg, 0.06 mmol, 47%) as a tan solid. ¹H NMR: (500 MHz, DMSO-d$_6$) δ 12.34 (br s, 1H), 8.91 (s, 1H), 8.90 (d, J=2.8 Hz, 1H), 8.55 (br d, J=3.4 Hz, 1H), 8.37 (dd, J=7.8, 1.5 Hz, 1H), 7.50-7.39 (m, 5H), 7.47 (ddd, J=8.2, 7.0, 1.5 Hz, 1H), 7.21 (d, J=2.8 Hz, 1H), 7.20 (d, J=8.2 Hz, 1H), 7.14 (dd, J=7.8, 7.0 Hz, 1H), 3.94 (s, 3H), 3.91-3.23 (m, 8H); LC/MS: (ES+) m/z (M+H)$^+$=535; HPLC R$_t$=1.42 min., column Q, conditions B.

Preparation of Example 19

1-(4-Benzoylpiperazin-1-yl)-2-(4-(3-(3-(trifluoromethyl)phenyl)-1H-pyrazol-1-yl)-5H-pyrrolo[3,2-d]pyrimidin-7-yl)ethane-1,2-dione (Compound 27)

Example 19

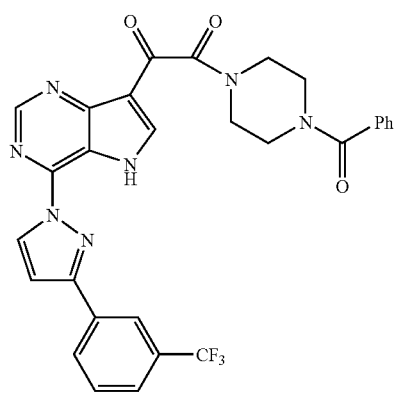

27

In a sealed tube dicarbonyl intermediate 10 (50 mg, 0.13 mmol), 3-(3-(trifluoromethyl)phenyl)-1H-pyrazole (150 mg, 0.70 mmol) and 1,4-dioxane (2 mL) were combined and heated at 160° C. with microwaves for 20 min. The reaction was concentrated, dissolved into MeOH (3 mL) and purified by preparative HPLC to yield 27 (34 mg, 0.06 mmol, 46%) as a white solid. $^1$H NMR: (500 MHz, DMSO-d$_6$) δ 12.63 (br s, 1H), 9.00 (d, J=2.8 Hz, 1H), 8.94 (s, 1H), 8.64 (s, 1H), 8.62 (d, J=7.9 Hz, 1H), 8.54 (s, 1H), 7.83 (d, J=7.6 Hz, 1H), 7.79 (dd, J=7.9, 7.6 Hz, 1H), 7.52-7.36 (m, 5H), 7.47 (d, J=2.8 Hz, 1H), 3.90-3.25 (m, 8H); LC/MS: (ES+) m/z (M+H)$^+$=574; HPLC R$_t$=1.77 min., column Q, conditions B.

Preparation of Example 20

1-(4-(1H-1,2,4-Triazol-1-yl)-5H-pyrrolo[3,2-d]pyrimidin-7-yl)-2-(4-benzoylpiperazin-1-yl)ethane-1,2-dione (Compound 28)

Example 20

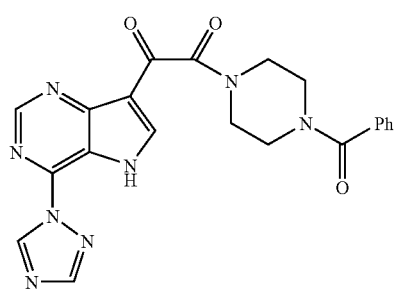

28

In a sealed tube dicarbonyl intermediate 10 (50 mg, 0.13 mmol), 1,2,4-triazole (26 mg, 0.44 mmol), copper(0) (8 mg, 0.13 mmol), K$_2$CO$_3$ (23 mg, 0.17 mmol) and 1,4-dioxane (0.8 mL) were combined and heated at 140° C. with microwaves for 6 h. The reaction mixture was diluted with MeOH/CH$_2$Cl$_2$ (1:1, 2 mL), filtered, concentrated, dissolved into MeOH/DMSO (5:4, 1.8 mL) and purified by preparative HPLC. The resulting yellow solid was triturated with MeOH to yield 28 (15 mg, 0.03 mmol, 28%) as a light yellow solid. $^1$H NMR: (500 MHz, DMSO-d$_6$) δ 12.95 (s, 1H), 9.71 (s, 1H), 8.98 (s, 1H), 8.61 (s, 1H), 8.56 (br s, 1H), 7.52-7.36 (m, 5H), 3.92-3.23 (m, 8H); LC/MS: (ES+) m/z (M+H)$^+$=431; HPLC R$_t$=0.98 min., column C.

Preparation of Example 21

1-(4-(1H-1,2,3-Triazol-1-yl)-5H-pyrrolo[3,2-d]pyrimidin-7-yl)-2-(4-benzoylpiperazin-1-yl)ethane-1,2-dione (Compound 29)

Example 21

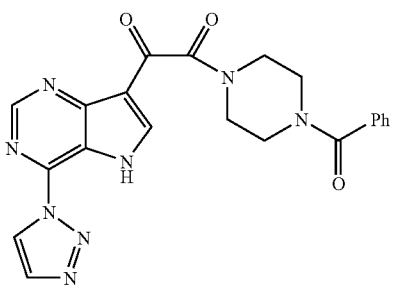

29

In a sealed tube dicarbonyl intermediate 10 (60 mg, 0.15 mmol) and 1,2,3-triazole (95 mg, 1.4 mmol) in 1,4-dioxane (3 mL) were combined and heated at 170° C. with microwaves for 20 min. The reaction was concentrated and the residue was triturated with MeOH to yield 29 (10 mg, 0.023 mmol, 16%) as a yellow solid. $^1$H NMR: (500 MHz, CD$_3$OD) δ 9.08 (s, 1H), 9.04 (s, 1H), 8.66 (s, 1H), 8.07 (s, 1H), 7.57-7.41 (m, 5H), 4.08-3.43 (m, 8H); LC/MS: (ES+) m/z (M+H)=431; HPLC R$_t$=0.95 min., column 0, conditions B.

Preparation of Example 22

1-(4-(1H-Pyrazol-3-yl)-5H-pyrrolo[3,2-d]pyrimidin-7-yl)-2-(4-benzoylpiperazin-1-yl)ethane-1,2-dione (Compound 30)

Example 22

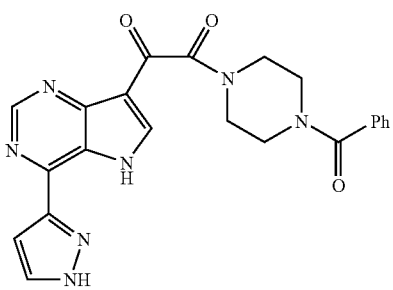

30

In a sealed tube dicarbonyl intermediate 10 (50 mg, 0.13 mmol), 3-(tributylstannyl)pyrazole (188 mg, 0.52 mmol), tetrakis(triphenylphosphine)-palladium(0) (72 mg, 0.06 mmol) and 1,4-dioxane (0.8 mL) were combined and heated at 110° C. with microwaves for 1 h. The reaction mixture was diluted with MeOH/CH$_2$Cl$_2$ (1:1, 2 mL) and filtered to collect solids. The solids were dissolved into DMSO and purified by preparative HPLC to yield 30 (28 mg, 0.07 mmol, 52%) as a white solid. $^1$H NMR: (500 MHz, DMSO-d$_6$) δ 13.63 (br s, 1H), 12.41 (s, 1H), 9.03 (s, 1H), 8.44 (d, J=2.3 Hz, 1H), 8.03 (d, J=2.3 Hz, 1H), 7.50-7.37 (m, 5H), 7.13 (d, J=1.8 Hz, 1H), 3.90-3.23 (m, 8H); LC/MS: (ES+) m/z (M+H)$^+$=430; HPLC R$_t$=0.87 min., column R, conditions B.

Preparation of Example 23

1-(4-Benzoylpiperazin-1-yl)-2-(4-(3-methylisoxazol-5-yl)-5H-pyrrolo[3,2-d]pyrimidin-7-yl)ethane-1,2-dione (Compound 31)

Example 23

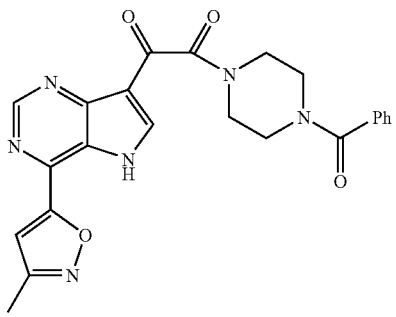

31

In a sealed tube dicarbonyl intermediate 10 (50 mg, 0.13 mmol), 3-methyl-5-(tributylstannyl)isoxazole (141 mg, 0.38 mmol), tetrakis(triphenylphosphine)-palladium (0) (30 mg, 0.03 mmol) and 1,4-dioxane (1 mL) were combined and heated at 110° C. with microwaves for 2 h, and then heated at 120° C. for 2 h. The reaction was repeated as described above and the reaction solution was heated at 110° C. with microwaves for 5 h. The two reactions were combined, diluted with MeOH/DMSO, filtered and purified by preparative HPLC. The resulting yellow solid was triturated with MeOH to yield 31 (4 mg, 0.008 mmol, 3%) as a white solid. $^1$H NMR: (500 MHz, CD$_3$OD) δ 9.11 (s, 1H), 8.66 (s, 1H), 7.56-7.42 (m, 5H), 7.27 (s, 1H), 4.06-3.45 (m, 8H), 2.47 (s, 3H); LC/MS: (ES+) m/z (M+H)$^+$=445; HPLC R$_t$=1.23 min., column L.

Preparation of Example 24

1-(4-Benzoylpiperazin-1-yl)-2-(4-(pyridin-2-yl)-5H-pyrrolo[3,2-d]pyrimidin-7-yl)ethane-1,2-dione (Compound 32)

Example 24

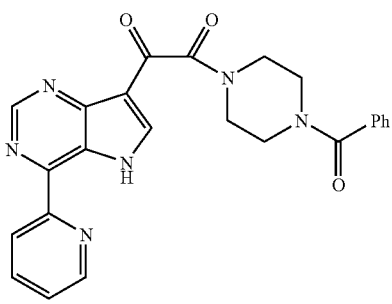

32

In a sealed tube dicarbonyl intermediate 10 (50 mg, 0.13 mmol), 2-(tributylstannyl)pyridine (140 mg, 0.38 mmol), tetrakis(triphenylphosphine)-palladium(0) (30 mg, 0.03 mmol) and 1,4-dioxane (0.8 mL) were combined and heated at 110° C. with microwaves for 1 h. The reaction mixture was concentrated, diluted with MeOH, filtered and purified by preparative HPLC to yield 32 (8 mg, 0.02 mmol, 14%) as a yellow waxy solid. $^1$H NMR: (500 MHz, CD$_3$OD) δ 9.15-9.10 (m, 1H), 8.89 (br s, 1H), 8.70 (d, J=7.9 Hz, 1H), 8.62 (s, 1H), 8.09-8.05 (m, 1H), 7.61-7.55 (m, 1H), 7.54-7.37 (m, 5H), 4.05-3.42 (m, 8H); LC/MS: (ES+) m/z (M+H)$^+$=441; HPLC R$_t$=1.54 min., column P.

Preparation of Example 25

1-(4-Benzoylpiperazin-1-yl)-2-(4-(pyridin-3-yl)-5H-pyrrolo[3,2-d]pyrimidin-7-yl)ethane-1,2-dione (Compound 33)

Example 25

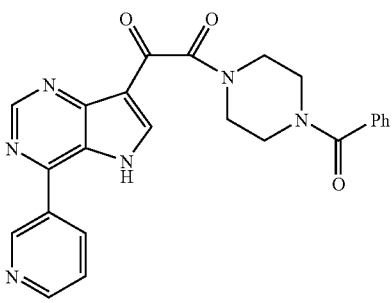

33

In a sealed tube dicarbonyl intermediate 10 (50 mg, 0.13 mmol), 3-(tributylstannyl)pyridine (160 mg, 0.43 mmol), tetrakis(triphenylphosphine)-palladium(0) (40 mg, 0.03 mmol) and 1,4-dioxane (0.8 mL) were combined and heated at 130°

C. for 4 h. The reaction mixture was concentrated to dryness and partitioned between EtOAc (5 mL) and saturated aqueous NaHCO₃ with cesium fluoride. The biphasic suspension was filtered, separated and the aqueous layer was concentrated to dryness. The residue was diluted with MeOH (2 mL) and DMSO (0.5 mL), filtered and purified by preparative HPLC to yield 33 (7 mg, 0.02 mmol, 12%) as a yellow solid. $^1$H NMR: (500 MHz, CD₃OD) δ 9.41 (s, 1H), 9.20 (s, 1H), 8.96 (d, J=5.5 Hz, 1H), 8.91 (d, J=7.6 Hz, 1H), 8.73 (s, 1H), 8.05 (dd, J=7.6, 5.5 Hz, 1H), 7.56-7.42 (m, 5H), 4.10-3.43 (m, 8H); LC/MS: (ES+) m/z (M+H)⁺=441; HPLC $R_t$=0.92 min., column S.

Preparation of Example 26

1-(4-Benzoylpiperazin-1-yl)-2-(4-(pyridin-4-yl)-5H-pyrrolo[3,2-d]pyrimidin-7-yl)ethane-1,2-dione (Compound 34)

Example 26

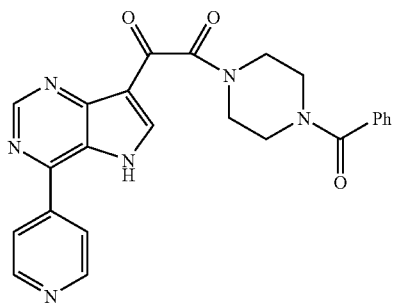

34

In a sealed tube dicarbonyl intermediate 10 (50 mg, 0.13 mmol), 4-(tributylstannyl)pyridine (140 mg, 0.38 mmol), tetrakis(triphenylphosphine)-palladium(0) (30 mg, 0.03 mmol) and 1,4-dioxane (0.8 mL) were combined and heated at 110° C. with microwaves for 2 h, and then at 120° C. for 2 h. The reaction mixture was concentrated, diluted with MeOH/DMSO, filtered and purified by preparative HPLC to yield 34 (22 mg, 0.08 mmol, 38%) as a yellow solid. $^1$H NMR: (500 MHz, CD₃OD) δ 9.24 (s, 1H), 9.04 (d, J=5.8 Hz, 2H), 8.75 (s, 1H), 8.52 (d, J=5.8 Hz, 2H), 7.57-7.40 (m, 5H), 4.12-3.44 (m, 8H); LC/MS: (ES+) m/z (M+H)⁺=441; HPLC $R_t$=0.78 min., column L.

Preparation of Example 27

1-(4-Benzoylpiperazin-1-yl)-2-(4-(pyrazin-2-yl)-5H-pyrrolo[3,2-d]pyrimidin-7-yl)ethane-1,2-dione (Compound 35)

Example 27

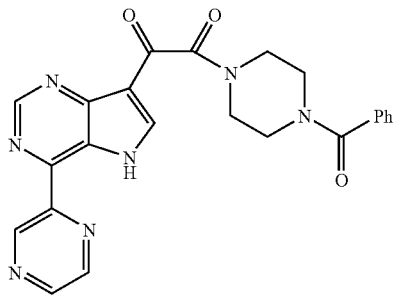

35

In a sealed tube dicarbonyl intermediate 10 (50 mg, 0.13 mmol), 2-(tributylstannyl)pyrazine (160 mg, 0.43 mmol), tetrakis(triphenylphosphine)-palladium(0) (30 mg, 0.03 mmol) and 1,4-dioxane (0.8 mL) were combined and heated at 120° C. with microwaves for 2 h, and then at 130° C. for 2 h. The reaction mixture was concentrated to dryness, diluted with MeOH (2.5 mL) and DMSO (0.5 mL), filtered and purified by preparative HPLC. The resulting yellow solid was triturated with MeOH to yield 35 (8 mg, 0.02 mmol, 15%) as a light yellow solid.

$^1$H NMR: (500 MHz, DMSO-d₆) δ 12.93 (br s, 1H), 9.75 (d, J=1.2 Hz, 1H), 9.21 (s, 1H), 8.93 (dd, J=2.4, 1.2 Hz, 1H), 8.90 (d, J=2.4 Hz, 1H), 8.64 (br s, 1H), 7.53-7.35 (m, 5H), 3.96-3.21 (m, 8H); LC/MS: (ES+) m/z (M+H)$^+$=442; HPLC R$_t$=1.15 min., column S.

Preparation of Example 28

1-(4-Benzoylpiperazin-1-yl)-2-(4-(pyrimidin-5-yl)-5H-pyrrolo[3,2-d]pyrimidin-7-yl)ethane-1,2-dione (Compound 36)

Example 28

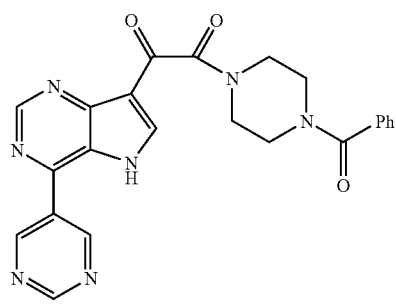

36

In a sealed tube dicarbonyl intermediate 10 (50 mg, 0.13 mmol), 5-(tributylstannyl)pyrimidine (160 mg, 0.43 mmol), tetrakis(triphenylphosphine)-palladium(0) (30 mg, 0.03 mmol) and 1,4-dioxane (0.8 mL) were combined and heated at 130° C. with microwaves for 2 h. The reaction mixture was concentrated, diluted with MeOH/DMSO, filtered and purified by preparative HPLC. The resulting orange solid was triturated with acetone to yield 36 (36.3 mg, 0.08 mmol, 63%) as a yellow solid. $^1$H NMR: (500 MHz, DMSO-d$_6$) δ 13.48 (br s, 1H), 9.42 (s, 1H), 9.41 (s, 2H), 9.18 (s 1H), 7.52-7.39 (m, 5H), 3.91-3.24 (m, 8H); LC/MS: (ES+) m/z (M+H)$^+$=442; HPLC R$_t$=0.90 min., column S.

Preparation of Example 29

1-(4-Benzoylpiperazin-1-yl)-2-(4-(pyridazin-4-yl)-5H-pyrrolo[3,2-d]pyrimidin-7-yl)ethane-1,2-dione (Compound 37)

Example 29

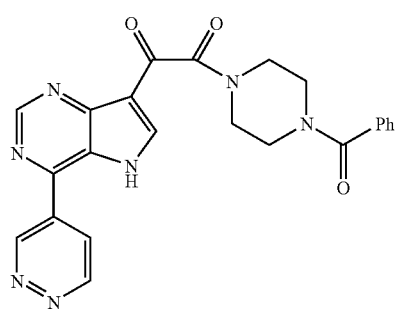

37

In a sealed tube dicarbonyl intermediate 10 (50 mg, 0.13 mmol), 4-(tributylstannyl)pyridazine (160 mg, 0.43 mmol), tetrakis(triphenylphosphine)-palladium(0) (30 mg, 0.03 mmol) and 1,4-dioxane (0.8 mL) were combined and heated at 130° C. with microwaves for 2 h. The reaction mixture was concentrated, diluted with MeOH, filtered and purified by preparative HPLC. The resulting black oil was repurified by preparative HPLC and the resulting yellow solid was triturated with acetone to yield 37 (18.7 mg, 0.04 mmol, 33%) as an off-white solid. $^1$H NMR: (500 MHz, DMSO-d$_6$) δ 13.48 (br s, 1H), 9.82 (br s, 1H), 9.54 (dd, J=5.2, 1.1 Hz, 1H), 9.22 (s 1H), 8.85 (br s, 1H), 8.29 (dd, J=5.2, 2.0 Hz, 1H), 7.54-7.37 (m, 5H), 3.91-3.25 (m, 8H); LC/MS: (ES+) m/z (M+H)$^+$=442; HPLC R$_t$=0.89 min., column S.

Preparation of 2-(4-(isoquinolin-1-yl)piperazin-1-yl)acetonitrile 38

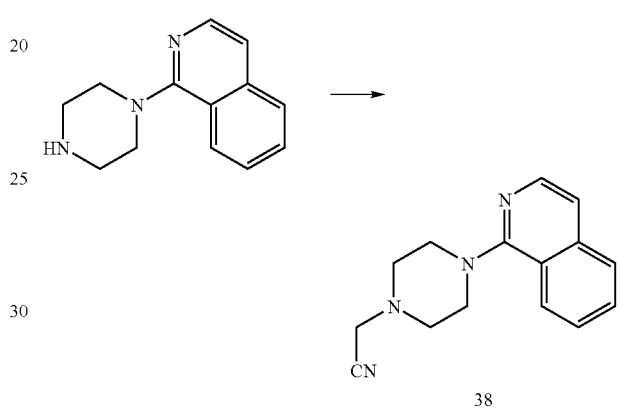

38

To a solution of 1-(piperazin-1-yl)isoquinoline (459 mg, 2.15 mmol) in THF (15 mL) was added NEt$_3$ (3.6 mL, 27 mmol) and chloroacetonitrile (1.8 mL, 28 mmol) and the reaction was stirred 3 h. The reaction mixture was filtered, concentrated and the residue purified by silica gel chromatography (Biotage 25-short, 25% EtOAc/hexanes to 100% EtOAc/hex) to yield 38 (188 mg, 0.75 mmol, 35%) as a white solid. LC/MS: (ES+) m/z (M+H)$^+$=253; HPLC R$_t$=1.23 min., column Q, conditions B.

Preparation of Example 30

1-(4-Chloro-5H-pyrrolo[3,2-d]pyrimidin-7-yl)-2-(4-(isoquinolin-1-yl)piperazin-1-yl)ethane-1,2-dione (Compound 39)

Example 30

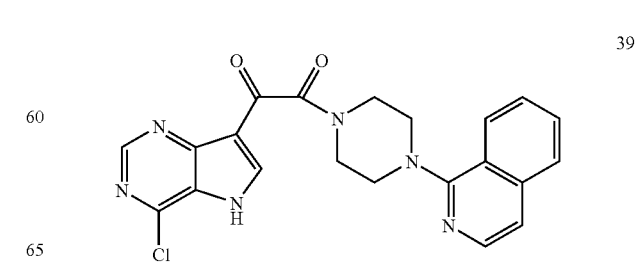

39

To a slurry of acid chloride intermediate 7 (115 mg, 0.53 mmol) and 2-(4-(isoquinolin-1-yl)piperazin-1-yl)acetonitrile 38 (188 mg, 0.75 mmol) in THF (5 mL), at −78° C., was added 0.5 M KHMDS in toluene (3.4 mL, 1.7 mmol). The reaction was stirred 2 h. and the presence of the desired cyanoketone intermediate was verified by LCMS. A solution of 32% peracetic acid in dilute aqueous acetic acid (0.5 mL, 2.4 mmol) was added and the reaction mixture was allowed to warm to ambient temperature overnight. The reaction mixture was diluted with EtOAc (10 mL) and saturated aqueous NH₄Cl (10 mL) and filtered. The layers were separated and the aqueous layer extracted with EtOAc (25 mL). The combined organic layers were concentrated and purified by preparative HPLC to yield 39 (102 mg, 0.24 mmol, 45%) as a bright yellow solid. ¹H NMR: (500 MHz, CD₃OD) δ 8.84 (s, 1H), 8.70 (s, 1H), 8.38 (d, J=7.9 Hz, 1H), 8.06 (d, J=7.2 Hz, 1H), 7.99 (dd, J=7.9, 7.6 Hz, 1H), 7.89 (d, J=6.7 Hz, 1H), 7.83 (dd, J=7.6, 7.2 Hz, 1H), 7.62 (d, J=6.7 Hz, 1H), 4.20-3.79 (m, 8H); LC/MS: (ES+) m/z (M+H)⁺=421; HPLC $R_t$=0.83 min., column S.

Preparation of Example 31

1-(4-(Isoquinolin-1-yl)piperazin-1-yl)-2-(4-(pyrazin - 2-yl)-5H-pyrrolo[3,2-d]pyrimidin-7-yl)ethane-1,2-dione (Compound 40)

Example 31

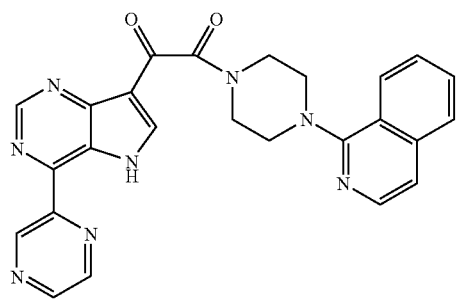

In a sealed tube dicarbonyl intermediate 39 (40 mg, 0.10 mmol), 2-(tributylstannyl)pyrazine (105 mg, 0.28 mmol), tetrakis(triphenylphosphine)-palladium(0) (30 mg, 0.03 mmol) and 1,4-dioxane (0.8 mL) were combined and heated at 130° C. with microwaves for 2 h. The reaction mixture was diluted with MeOH (1 mL) and DMSO (1 mL), filtered through celite and purified by preparative HPLC to yield 40 (12 mg, 0.03 mmol, 27%) as a yellow solid. ¹H NMR: (500 MHz, CD₃OD) δ 9.85 (s, 1H), 9.21 (s, 1H), 8.93 (br s, 1H), 8.83 (d, J=2.4 Hz, 1H), 8.72 (s, 1H), 8.42 (d, J=8.9 Hz, 1H), 8.09 (d, J=7.9 Hz, 1H), 8.05 (dd, J=8.0, 7.0 Hz, 1H), 7.87 (dd, J=8.9, 8.0 Hz, 1H), 7.85 (d, J=7.0 Hz, 1H), 7.66 (d, J=6.7 Hz, 1H), 4.24-4.20 (m, 2H), 4.14-4.04 (m, 2H), 3.99-3.91 (m, 4H); LC/MS: (ES+) m/z (M+H)⁺=465; HPLC $R_t$=0.92 min., column S.

Preparation of Example 32

1-(4-(1H-Pyrazol-1-yl)-5H-pyrrolo[3,2-d]pyrimidin-7-yl)-2-(4-(isoquinolin-1-yl)piperazin-1-yl)ethane-1,2-dione (Compound 41)

Example 32

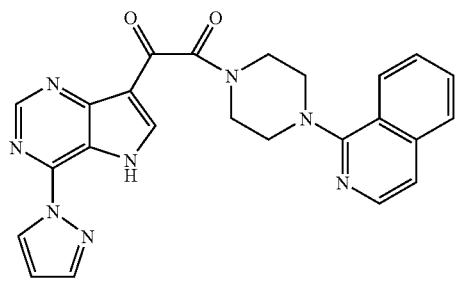

In a sealed tube dicarbonyl intermediate 39 (41 mg, 0.10 mmol), pyrazole (26 mg, 0.38 mmol), copper(0) (10 mg) and 1,4-dioxane (0.8 mL) were combined and heated at 140° C. with microwaves for 50 min. The reaction mixture was diluted with MeOH (1 mL) and DMSO (1 mL), filtered through celite and purified by preparative HPLC to yield 41 (11 mg, 0.02 mmol, 23%) as a light yellow solid. ¹H NMR: (500 MHz, CD₃OD) δ 8.90 (br s, 1H), 8.85 (d, J=2.5 Hz, 1H), 8.61 (s, 1H), 8.42 (d, J=8.5 Hz, 1H), 8.09 (d, J=7.9 Hz, 1H), 8.08 (s, 1H), 8.04 (dd, J=7.6, 7.3 Hz, 1H), 7.89-7.85 (m, 1H), 7.85 (d, J=6.7 Hz, 1H), 7.66 (d, J=7.0 Hz, 1H), 6.72 (dd, J=2.5, 1.6 Hz, 1H), 4.22-4.18 (m, 2H), 4.12-4.07 (m, 2H), 3.97-3.89 (m, 4H); LC/MS: (ES+) m/z (M+H)⁺=453; HPLC $R_t$=0.97 min., column S.

Preparation of 2-(1-(cyanomethyl)piperidin-4-ylidene)-2-phenylacetonitrile 42

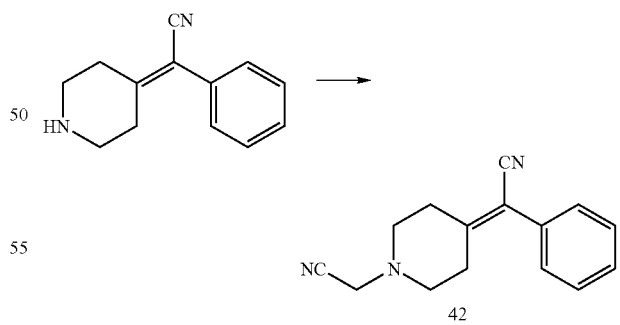

To a solution of 2-phenyl-2-(piperidin-4-ylidene)acetonitrile (6.8 g, 34 mmol) in THF (150 mL) was added NEt₃ (40 mL, 300 mmol) and chloroacetonitrile (20 mL, 315 mmol) and the reaction was stirred 16 h. The precipitates was filtered away and the filtrate concentrated to dryness. The residues was purified by silica gel chromatography (Biotage 40-short, 20% EtOAc/Hex to 50% EtOAc/Hex) to yield 42 (1.7 g, 7.2 mmol, 21%) as a yellow waxy solid. ¹H NMR: (500 MHz, CDCl$_3$) δ 7.44-7.34 (m, 3H), 7.30-7.27 (m, 2H), 3.65 (s, 2H), 2.96 (t, J=5.3 Hz, 2H), 2.90 (t, J=5.3 Hz, 2H), 2.70 (t, J=5.6 Hz, 2H), 2.62 (t, J=5.6 Hz, 2H); LC/MS: (ES+) m/z (M+H)$^+$= 238; HPLC R$_t$=1.33 min., column O, conditions B.

Preparation of Example 33

2-(1-(2-(4-Chloro-5H-pyrrolo[3,2-d]pyrimidin-7-yl)-2-oxoacetyl)piperidin-4-ylidene)-2-phenylacetonitrile (Compound 43)

Example 33

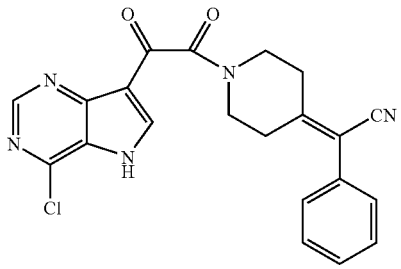

43

To a slurry of acid chloride intermediate 7 (100 mg, 0.46 mmol) and phenylcyanoalkene intermediate 42 (143 mg, 0.60 mmol) in THF (4 mL) at −78° C. was added a solution of 0.5 M KHMDS in toluene (3.0 mL, 1.5 mmol). The reaction was stirred 2 h and the presence of the desired cyanoketone intermediate was verified by LCMS. A solution of 32% peracetic acid in dilute aqueous acetic acid (0.44 mL, 2.1 mmol) was added to the reaction mixture and then allowed to warm to ambient temperature overnight. The reaction mixture was diluted with EtOAc (15 mL) and saturated aqueous NH$_4$Cl (10 mL). The layers were separated and the aqueous layer extracted with EtOAc (2×20 mL). The combined organic layers were concentrated, the residue was purified by preparative HPLC and the resulting yellow solid was triturated with MeOH to yield 43 (18.6 mg, 0.04 mmol, 10%) as a white solid. $^1$H NMR: (500 MHz, DMSO-d$_6$) δ 13.73 (s, 1H), 8.85 (s, 0.5H), 8.84 (s, 0.5H), 8.79 (s, 0.5H), 8.76 (s, 0.5H), 7.54-7.30 (m, 5H), 3.86 (t, J=5.8 Hz, 1H), 3.70 (t, J=5.8 Hz, 1H), 3.56 (t, J=5.8 Hz, 1H), 3.38 (t, J=5.8 Hz, 1H), 2.93 (t, J=5.8 Hz, 1H), 2.65 (t, J=5.8 Hz, 1H), 2.63 (dd, J=5.8 Hz, 1H), 2.36 (t, J=5.8 Hz, 1H); LC/MS: (ES+) m/z (M+H)$^+$=406; HPLC R$_t$=1.28 min., column S.

Preparation of Example 34

2-(1-(2-Oxo-2-(4-(pyrimidin-5-yl)-5H-pyrrolo[3,2-d]pyrimidin-7-yl)acetyl)piperidin-4-ylidene)-2-phenylacetonitrile (Compound 44)

Example 34

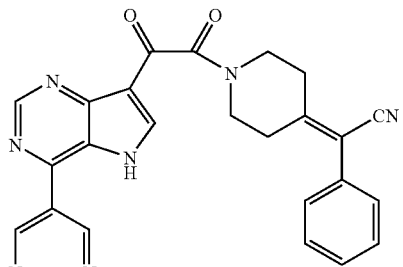

44

In a sealed tube dicarbonyl intermediate 33 (30 mg, 0.074 mmol), 5-(tributylstannyl)pyrimidine (82 mg, 0.22 mmol), tetrakis(triphenylphosphine)-palladium(0) (20 mg, 0.02 mmol) and 1,4-dioxane (0.8 mL) were combined and heated at 130° C. with microwaves for 2 h. The reaction mixture was diluted with MeOH/DMSO, filtered and purified by preparative HPLC to yield 44 (8 mg, 0.02 mmol, 30%) as a yellow solid. $^1$H NMR: (500 MHz, CD$_3$OD) δ 9.47 (s, 1H), 9.45 (s, 1H), 9.40 (s, 0.5H), 9.39 (s, 0.5H), 9.19 (s, 0.5H), 9.18 (s, 0.5H), 8.72 (s, 0.5H), 8.69 (s, 0.5H), 7.53-7.31 (m, 5H), 4.02 (dd, J=6.1, 5.8 Hz, 1H), 3.84 (dd, J=6.1, 5.8 Hz, 1H), 3.75 (dd, J=5.8, 5.8 Hz, 1H), 3.57 (dd, J=6.1, 5.8 Hz, 1H), 3.07 (dd, J=6.1, 5.8 Hz, 1H), 2.86 (dd, J=5.8, 5.8 Hz, 1H), 2.74 (dd, J=6.1, 5.8 Hz, 1H), 2.54 (dd, J=6.1, 5.8 Hz, 1H); LC/MS: (ES+) m/z (M+H)$^+$=450; HPLC R$_t$=1.48 min., column O.

Preparation of 2-(4-((1,3,4-oxadiazol-2-yl)(phenyl)methylene)piperidin-1-yl)acetonitrile 45

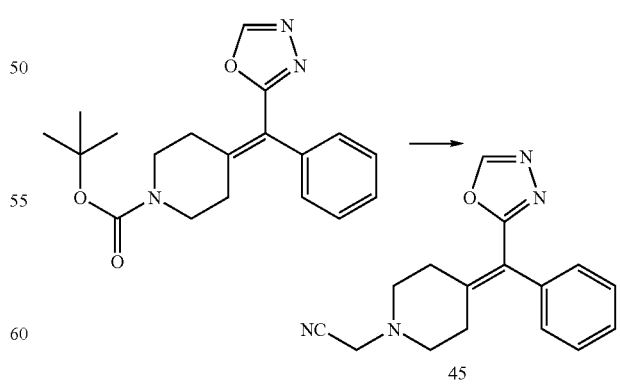

tert-Butyl 4-((1,3,4-oxadiazol-2-yl)(phenyl)methylene)piperidine-1-carboxylate (100 mg, 0.29 mmol) was diluted with 4 M HCl in 1,4-dioxane (1.2 mL, 4.8 mmol) and stirred 1 h. The reaction was concentrated and the residue diluted with THF (1.5 mL), triethylamine (0.5 mL, 3.8 mmol) and chloroacetonitrile (0.25 mL, 3.9 mmol). The reaction was stirred 3 d, concentrated, diluted with MeOH, filtered and purified by preparative HPLC to yield 45 (43 mg, 0.15 mmol, 53%) as a white solid. $^1$H NMR: (500 MHz, CDCl$_3$) δ 8.27 (s, 1H), 7.41-7.31 (m, 3H), 7.20-7.16 (m, 2H), 3.55 (s, 2H), 3.02 (t, J=5.8 Hz, 2H), 2.75 (t, J=5.8 Hz, 2H), 2.61 (t, J=5.8 Hz, 2H), 2.39 (t, J=5.8 Hz, 2H); LC/MS: (ES+) m/z (M+H)=281; HPLC R$_t$=0.97 min., column G, conditions B.

Preparation of Example 35

1-(4-((1,3,4-Oxadiazol-2-yl)(phenyl)methylene)piperidin-1-yl) -2-(4-(1H-1,2,4-triazol-1-yl)-5H-pyrrolo[3,2-d]pyrimidin-7-yl)ethane-1,2-dione (Compound 46)

Example 35

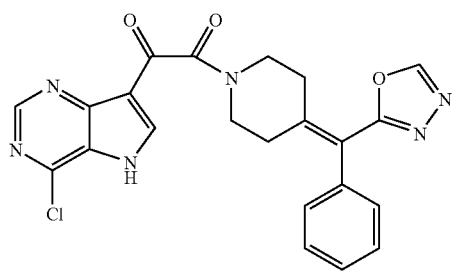

46

To a slurry of acid chloride intermediate 7 (600 mg, 2.8 mmol) and 2-(4-((1,3,4-oxadiazol-2-yl)(phenyl)methylene) piperidin-1-yl)acetonitrile 45 (800 mg, 2.9 mmol) in THF (5 mL), at −78° C. was added a solution of 0.5 M KHMDS in toluene (17.2 mL, 8.6 mmol). The reaction was stirred 2 h. A solution of 32% peracetic acid in dilute aqueous acetic acid (2.8 mL, 13 mmol) was added and the reaction mixture was allowed to warm to ambient temperature over 1 h. The reaction mixture was diluted with EtOAc (30 mL) and brine (25 mL) and filtered. The layers were separated and the organic layer concentrated. The residue was triturated with Et$_2$O to yield 46 (340 mg, 0.76 mmol, 27%) as an orange/yellow solid. $^1$H NMR: (500 MHz, DMSO-d$_6$) δ 13.73 (s, 1H), 9.17 (s, 0.5H), 9.10 (s, 0.5H), 8.83 (s, 0.5H), 8.82 (s, 0.5H), 8.76 (s, 0.5H), 8.74 (s, 0.5H), 7.49-7.15 (m, 5H), 3.80 (t, J=5.8 Hz, 1H), 3.71 (t, J=5.8 Hz, 1H), 3.49 (t, J=5.8 Hz, 1H), 3.40 (t, J=5.8 Hz, 1H), 3.02 (t, J=5.8 Hz, 1H), 2.75 (t, J=5.8 Hz, 1H), 2.52 (t, J=5.8 Hz, 1H), 2.25 (t, J=5.8 Hz, 1H); LC/MS: (ES+) m/z (M+H)$^+$=449; HPLC R$_t$=1.10 min., column P, conditions B.

Preparation of Example 36

1-(4-((1,3,4-Oxadiazol-2-yl)(phenyl)methylene)piperidin-1-yl) -2-(4-(1H-1,2,4-triazol-1-yl)-5H-pyrrolo[3,2-d]pyrimidin-7-yl)ethane-1,2-dione (Compound 47)

Example 36

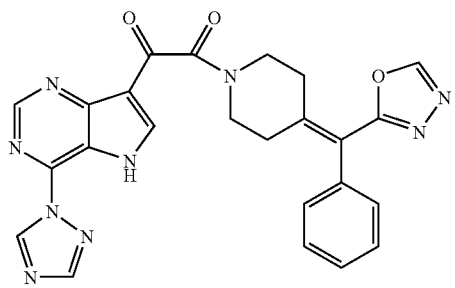

47

In a sealed tube dicarbonyl intermediate 46 (30 mg, 0.07 mmol), 1,2,4-triazole (28 mg, 0.41 mmol), copper(0) (8 mg, 0.13 mmol), K$_2$CO$_3$ (20 mg, 0.14 mmol) and 1,4-dioxane (1 mL) were combined and heated at 140° C. with microwaves for 2 h. The reaction mixture was diluted with MeOH/DMSO (2:3, 1 mL) and purified by preparative HPLC to yield 47 (4 mg, 0.008 mmol, 12%) as a yellow solid. $^1$H NMR: (500 MHz, CD$_3$OD) δ 9.62 (s, 0.5H), 9.62 (s, 0.5H), 8.87 (s, 0.5H), 8.79 (s, 0.5H), 8.60 (s, 0.5H), 8.58 (s, 0.5H), 8.44 (s, 0.5H), 8.43 (s, 0.5H), 7.48-7.14 (m, 6H), 3.95 (dd, J=6.1, 5.8 Hz, 1H), 3.83 (dd, J=6.1, 5.8 Hz, 1H), 3.68 (dd, J=6.1, 5.5 Hz, 1H), 3.58 (dd, J=5.8, 5.8 Hz, 1H), 3.10 (dd, J=6.1, 5.8 Hz, 1H), 2.90 (dd, J=6.1, 5.5 Hz, 1H), 2.61 (dd, J=6.1, 5.8 Hz, 1H), 2.42 (dd, J=6.1, 5.5 Hz, 1H); LC/MS: (ES+) m/z (M+H)$^+$= 482; HPLC R$_t$=1.13 min., column P, conditions B.

Preparation of Example 37

1-(4-((1,3,4-Oxadiazol-2-yl)(phenyl)methylene)piperidin-1-yl) -2-(4-(1H-pyrazol-1-yl)-5H-pyrrolo[3,2-d]pyrimidin-7-yl)ethane-1,2-dione (Compound 48)

Example 37

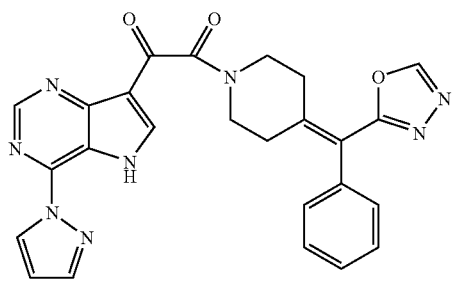

48

In a sealed tube dicarbonyl intermediate 46 (30 mg, 0.07 mmol), pyrazole (34 mg, 0.5 mmol) and 1,4-dioxane (0.7 mL) were combined and heated at 140° C. with microwaves for 50 min. The reaction mixture was diluted with MeOH/DMSO (1:1, 1.2 mL) and purified by preparative HPLC to yield 48 (10 mg, 0.02 mmol, 32%) as a yellow solid. $^1$H NMR: (500 MHz, CD$_3$OD) δ 8.86 (s, 1H), 8.85 (s, 0.5H), 8.82 (d, J=2.8 Hz, 0.5H), 8.81 (d, J=2.8 Hz, 0.5H), 8.79 (s, 0.5H), 8.53 (s, 0.5H), 8.51 (s, 0.5H), 8.04 (d, J=1.5 Hz, 0.5H), 8.03 (d, J=1.5 Hz, 0.5H), 7.46-7.16 (m, 5H), 6.71-6.67 (m, 1H), 3.94 (dd, J=6.1, 5,8 Hz, 1), 3.81 (dd, J=6.1, 5.8 Hz, 1H), 3.69 (dd, J=6.1, 5.8 Hz, 1H), 3.57 (dd, J=5.8, 5.8 Hz, 1H), 3.08 (dd, J=5.8, 5.8 Hz, 1H), 2.91 (dd, J=6.1, 5.8 Hz, 1H), 2.59 (dd, J=6.1, 5.8 Hz, 1H), 2.43 (dd, J=6.1, 5.8 Hz, 1H); LC/MS: (ES+) m/z (M+H)$^+$=481; HPLC R$_f$=1.27 min., column P, conditions B.

Preparation of Ethyl 4-(1H-pyrazol-1-yl)-5H-pyrrolo[3,2-d]pyrimidine-7-carboxylate 49

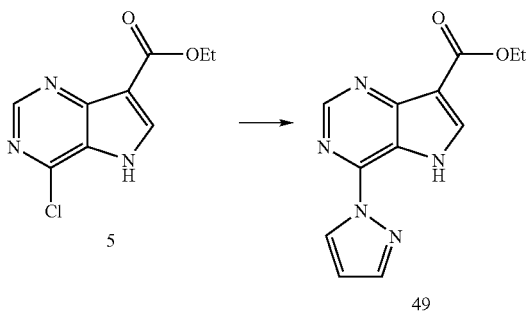

In a sealed tube 4-chloro-5H-pyrrolo[3,2-d]pyrimidine-7-carbonyl chloride 5 (2.0 g, 8.9 mmol), pyrazole (1.8 g, 26.5 mmol) and 1,4 dioxane (10 mL) were heated at 138° C. for 2 h. Upon cooling to ambient temperature a precipitate formed which was collected and washed with saturated aqueous NaHCO$_3$ and diethyl ether to yield 49 (340 mg, 1,3 mmol) as a white solid. The filtrate was treated with saturated aqueous NaHCO$_3$ (20 ml) and the resulting precipitate was washed with saturated aqueous NaHCO$_3$ and diethyl ether to yield additional 49 (2.0 g, 7.8 mmol, 99% total yield). $^1$H NMR: (500 MHz, CD$_3$OD) δ 8.99 (br s, 1H), 8.78 (br s, 1H), 8.29 (s, 1H), 8.06 (br s, 1H), 6.72 (br s, 1H), 4.30 (q, J=7.0 Hz, 2H), 1.33 (t, J=7.0 Hz, 3H); LC/MS: (ES+) m/z (M+H)$^+$=258; HPLC R$_f$=1.20 min., column L.

Preparation of 4-(1H-pyrazol-1-yl)-5H-pyrrolo[3,2-d]pyrimidine-7-carboxylic Acid 50

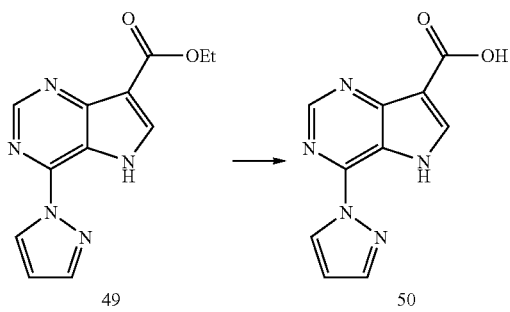

To a solution of 4-(1H-pyrazol-1-yl)-5H-pyrrolo[3,2-d]pyrimidine-7-carboxylate 49 (2.0 g, 7.8 mmol) in THF (45 mL) was added a solution of LiOH.H$_2$O (1.3 g, 31 mmol) in H$_2$O (30 mL) and the reaction was stirred at 100° C. for 16 h. Additional LiOH.H$_2$O (2.0 g, 48 mmol) was added, heating continued for 2 h, MeOH was added (10 mL) and heating continued at 100° C. for 1d. The reaction mixture was cooled, filtered, concentrated to ~20% volume and neutralized with ice and conc HCl. The white precipitate that formed was collected by filtration and washed with brine, H$_2$O, EtOAc, and Et$_2$O to yield 50 (quantitative), which was used without further purification. $^1$H NMR: (500 MHz, DMSO-d$_6$) δ 12.07 (br s, 1H), 8.89 (br s, 1H), 8.75 (s, 1H), 8.14 (s, 1H), 8.09 (br s, 1H), 6.76-6.73 (m, 1H);

LC/MS: (ES+) m/z (M+H)$^+$=230; HPLC R$_f$=0.75 min., column S.

Preparation of 4-(1H-pyrazol-1-yl)-5H-pyrrolo[3,2-d]pyrimidine-7-carbonyl chloride 51

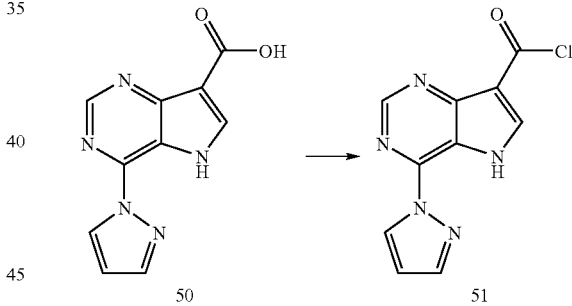

Oxalyl chloride (4.5 mL, 51 mmol) was added to a solution of diazaindole carboxylic acid 50 (1.08 g, 4.7 mmol) in CH$_2$Cl$_2$ (8 mL) and the reaction mixture was stirred 14 h. Catalytic DMF (3 drops) was added to the reaction mixture and after 3 h the reaction was quenched with MeOH. The crude reaction mixture was concentrated to dryness to yield 51 (1.21 g, 49 mmol, 96%) as a tan solid with was used without further purification. $^1$H NMR: (500 MHz, DMSO-d$_6$) δ 12.45 (br s, 1H), 8.87 (s, 1H), 8.87 (d, J=2.6 Hz, 1H), 8.32 (d, J=3.3 Hz, 1H), 8.14 (d, J=1.5 Hz, 1H), 6.77 (dd, J=2.6, 1.5

Hz, 1H); Methyl ester (obtained by stirring 51 in MeOH): LC/MS: (ES+) m/z (M+H)+=244; HPLC R$_t$=0.95 min., column 0, conditions B.

Preparation of 2-(1-(cyanomethyl)piperidin-4-ylidene)-2-(pyridin-2-yl)acetonitrile 52

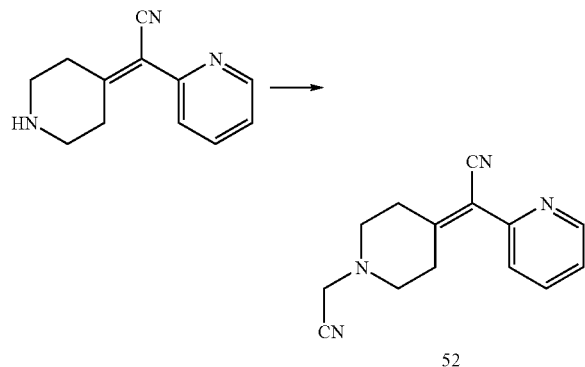

To a solution of 2-(piperidin-4-ylidene)-2-(pyridin-2-yl)acetonitrile (560 mg, 2.8 mmol) in THF (20 mL) was added NEt$_3$ (5 mL, 38 mmol) and chloroacetonitrile (3 mL, 47 mmol) and the reaction was stirred 16 h. The resulting precipitates were filtered away and the filtrate concentrated to dryness. The residues was purified by silica gel chromatography (Biotage 40-short, 50% EtOAc/hexanes to 100% EtOAc/hexanes) to yield 52 (470 mg, 2.0 mmol, 71%) as a yellow solid. $^1$H NMR: (500 MHz, CDCl$_3$) δ 8.64 (br d, J=4.9 Hz, 1H), 7.77 (ddd, J=7.9, 7.6, 1.9 Hz, 1H), 7.50 (d, J=7.9 Hz, 1H), 7.27 (dd, J=7.6, 4.9 Hz, 1H), 3.58 (s, 2H), 2.94 (t, J=5.8 Hz, 2H), 2.91 (t, J=5.8 Hz, 2H), 2.83 (t, J=5.8 Hz, 2H), 2.67 (t, J=5.8 Hz, 2H); LC/MS: (ES+) m/z (M+H)+=239; HPLC R$_t$=0.99 min., column 0, conditions B.

Preparation of Example 38

2-(1-(2-(4-(1H-pyrazol-1-yl)-5H-pyrrolo[3,2-d]pyrimidin-7-yl)-2-oxoacetyl)piperidin-4-ylidene)-2-(pyridin-2-yl)acetonitrile (Compound 53)

Example 38

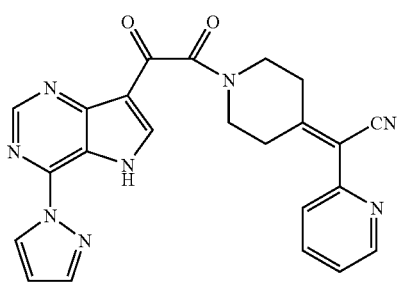

To a slurry of acid chloride pyrazole intermediate 51 (100 mg, 0.40 mmol) and 3-pyridinylcyanoalkene intermediate 52 (100 mg, 0.42 mmol) in THF (4 mL) at −78° C. was added a solution of 0.5 M KHMDS in toluene (3.0 mL, 1.5 mmol). The reaction mixture was stirred at −78° C. for 3 h and the presence of the desired cyanoketone intermediate was verified by LCMS. A solution of 32% peracetic acid in dilute aqueous acetic acid (0.44 mL, 2.1 mmol) was added to the reaction mixture and then allowed to warm to ambient temperature overnight. The reaction mixture was diluted with H$_2$O (5 mL) and saturated aqueous NH$_4$Cl (5 mL) and extracted with EtOAc (3×20 mL). The layers were separated and the aqueous layer extracted with EtOAc (2×20 mL). The combined organic layers were concentrated, the residue was purified by preparative HPLC to yield 53 (7.3 mg, 0.02 mmol, 4%) as a yellow solid. $^1$H NMR: (500 MHz, CD$_3$OD) δ 8.95 (s, 0.5H), 8.93 (s, 0.5H), 8.88 (d, J=2.8 Hz, 0.5H), 8.86 (d, J=3.1 Hz, 0.5H), 8.71 (br d, J=4.9 Hz, 0.5H), 8.64-8.61 (m, 1H), 8.60 (s, 0.5H), 8.11 (br s, 0.5H), 8.10 (br s, 0.5H), 8.03 (ddd, J=7.9, 7.6, 1.5 Hz, 0.5H), 7.97 (ddd, J=7.9, 7.6, 1.5 Hz, 0.5H), 7.65 (d, J=7.9 Hz, 0.5H), 7.60 (d, J=7.9 Hz, 0.5H), 7.52 (dd, J=7.9, 4.9 Hz, 0.5H), 7.46 (dd, J=7.9, 4.9 Hz, 0.5H), 6.76-6.72 (m, 1H), 4.03 (dd, J=6.1, 6.1 Hz, 1H), 3.86 (dd, J=6.1, 5.8 Hz, 1H), 3.81 (dd, J=6.1, 5.5 Hz, 1H), 3.64 (dd, J=5.8, 5.8 Hz, 1H), 3.10 (dd, J=6.1, 5.8 Hz, 1H), 2.94 (dd, J=6.1, 5.5 Hz, 1H), 2.90 (dd, J=6.1, 5.8 Hz, 1H), 2.75 (dd, J=5.8, 5.8 Hz, 1H); LC/MS: (ES+) m/z (M+H)+=439; HPLC R$_t$=1.37 min., column O.

Preparation of Example 39

1-(4-Benzoylpiperazin-1-yl)-2-(4-(3-(pyridin-2-yl)-1H-pyrazol-1-yl)-5H-pyrrolo[3,2-d]pyrimidin-7-yl)ethane-1,2-dione (Compound 54)

Example 39

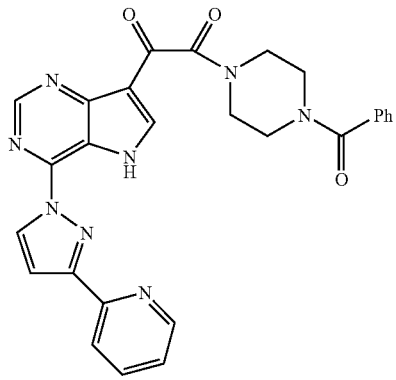

In a sealed tube dicarbonyl intermediate 10 (52 mg, 0.13 mmol), 2-(1H-pyrazol-3-yl)pyridine (104 mg, 0.71 mmol) and 1,4-dioxane (2.0 mL) were combined and heated at 150° C. with microwaves for 1 h. The reaction mixture was concentrated, diluted with MeOH, filtered and purified by preparative HPLC to yield 54 (31 mg, 0.06 mmol, 47%) as an off-white solid. $^1$H NMR: (500 MHz, DMSO-d$_6$) δ 12.60 (br s, 1H), 8.97 (d, J=1.8 Hz, 1H), 8.94 (s, 1H), 8.73-8.66 (m, 2H), 8.61 (br s, 1H), 8.02 (t, J=7.0 Hz, 1H), 7.54-7.38 (m, 6H), 7.31 (d, J=1.8 Hz, 1H), 3.92-3.13 (m, 8H); LC/MS: (ES+) m/z (M+H)⁺=507; HPLC R$_t$=1.19 min., column N.

Preparation of
2-(4-(quinazolin-4-yl)piperazin-1-yl)acetonitrile 55

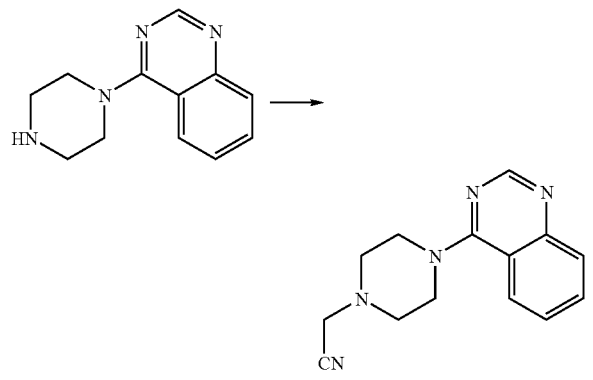

To a solution of 4-(piperazin-1-yl)quinazoline (1.8 g, 8.3 mmol) in THF (50 mL) was added NEt$_3$ (20 mL, 150 mmol) and chloroacetonitrile (12 mL, 190 mmol) and the reaction was stirred 16 h. The reaction mixture was quenched with 50% saturated aqueous NaHCO$_3$ and extracted with EtOAc (3×200 mL). The combined organics were purified by silica gel chromatography (50% EtOAc/hexanes to 80% EtOAc/hexanes) to yield 55 (1.6 g, 6.1 mmol, 73%) as an viscous yellow oil. ¹H NMR: (500 MHz, CDCl$_3$) δ 8.74 (s, 1H), 8.06 (d, J=8.6 Hz, 1H), 7.90 (d, J=8.5 Hz, 1H), 7.82-7.55 (m, 1H), 7.54-7.50 (m, 1H), 3.94-3.88 (m, 4H), 3.63 (s, 2H), 2.86-2.81 (m, 4H); LC/MS: (ES+) m/z (M+H)⁺=254; HPLC R$_t$=0.71 min., column O.

Preparation of Example 40

1-(4-(1H-Pyrazol-1-yl)-5H-pyrrolo[3,2-d]pyrimidin-7-yl)-2-(4-(quinazolin-4-yl)piperazin-1-yl)ethane-1,2-dione (Compound 56)

Example 40

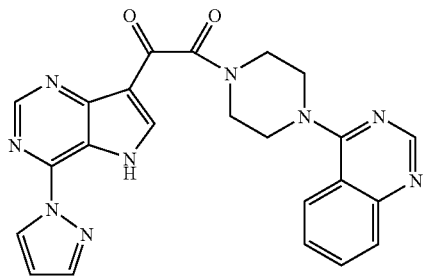

To a slurry of acid chloride pyrazole intermediate 51 (100 mg, 0.40 mmol) and 2-(4-(quinazolin-4-yl)piperazin-1-yl) acetonitrile 55 (98 mg, 0.39 mmol) in THF (4 mL), at −78° C. was added a solution of 0.5 M KHMDS in toluene (3.0 mL, 1.5 mmol). The reaction mixture was stirred 3 h and the presence of the desired cyanoketone intermediate was verified by LCMS. The reaction was treated with a solution of 32% peracetic acid in dilute aqueous acetic acid (0.40 mL, 1.9 mmol) and then allowed to warm to ambient temperature overnight. The reaction mixture was diluted with saturated aqueous NH$_4$Cl (5 mL) and extracted with EtOAc (3×20 mL). The combined organic layers were concentrated, the residue was purified by preparative HPLC to yield 56 (33 mg, 0.07 mmol, 18%) as a yellow solid. ¹H NMR: (500 MHz, CD$_3$OD) δ 8.86 (s, 1H), 8.5 (d, J=2.7 Hz, 1H), 8.75 (s, 1H), 8.61 (s, 1H), 8.30 (d, J=8.2 Hz, 1H), 8.09-8.05 (m, 2H), 7.84 (d, J=8.5 Hz, 1H), 7.79 (dd, J=8.2, 7.6 Hz, 1H), 6.72 (br s, 1H), 4.62-4.56 (m, 2H), 4.43-4.38 (m, 2H), 4.12-4.07 (m, 2H), 3.91-3.86 (m, 2H); LC/MS: (ES+) m/z (M+H)⁺=439; HPLC R$_t$=1.06 min., column O.

Preparation of Example 41

1-(4-(4-(1H-Pyrazole-3-carbonyl)piperazin-1-yl)-5H-pyrrolo[3,2-d]pyrimidin-7-yl)-2-(4-benzoylpiperazin-1-yl)ethane-1,2-dione (Compound 57)

Example 41

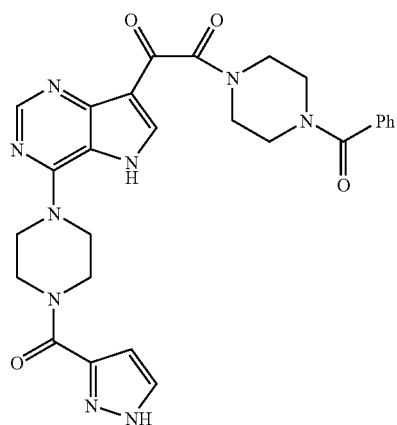

In a sealed tube dicarbonyl intermediate 10 (50 mg, 0.13 mmol), (4-methylpiperazin-1-yl)(1H-pyrazol-3-yl)methanone (75 mg, 0.39 mmol) and copper powder (10 mg, 0.16 mmol) were combined and heated at 150° C. with microwaves for 2 h. The reaction was purified by preparative HPLC to yield 57 (65 mg, 0.12 mmol, 92%) as a white solid. ¹H NMR: (500 MHz, CD$_3$COCD$_3$) δ 10.31 (br s, 2H), 8.82 (s, 1H), 8.85 (s, 1H), 7.80 (s, 1H), 7.50-7.40 (m, 5H), 6.74 (s, 1H), 4.50-4.37 (m, 6H), 4.09-3.96 (m, 2H), 3.86-3.60 (m, 8H); LC/MS: (ES+) m/z (M+H)$^+$=542; HPLC R$_t$=0.85 min., column G, conditions B.

Preparation of Example 42

2-(1-(2-(4-(1H-Pyrazol-1-yl)-5H-pyrrolo[3,2-d]pyrimidin-7-yl)-2-oxoacetyl)piperidin-4-ylidene)-2-phenylacetonitrile (Compound 58)

Example 42

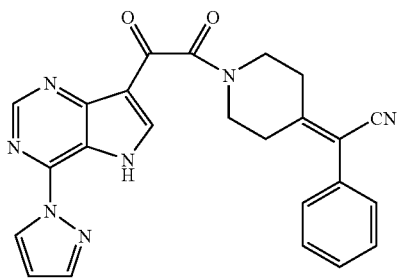

58

In a sealed tube dicarbonyl intermediate 33 (31 mg, 0.077 mmol), pyrazole (20 mg, 0.29 mmol) and 1,4-dioxane (0.8 mL) were combined and heated at 140° C. with microwaves for 50 min. The reaction mixture was diluted with MeOH/DMSO (2:1, 1.5 mL), filtered and purified by preparative HPLC to yield 58 (10 mg, 0.024 mmol, 31%) as an orange solid. $^1$H NMR: (500 MHz, CD$_3$OD) δ 8.90 (s, 0.5H), 8.88 (s, 0.5H), 8.86 (d, J=2.8 Hz, 0.5H), 8.84 (d, J=2.8 Hz, 0.5H), 8.57 (s, 0.5H), 8.54 (s, 0.5H), 8.08 (br s, 0.5H), 8.06 (br s, 0.5H), 7.53-7.31 (m, 5H), 6.74-6.70 (m, 1H), 4.00 (t, J=5.8 Hz, 1H), 3.82 (t, J=5.8 Hz, 1H), 3.75 (t, J=5.8 Hz, 1H), 3.56 (t, J=5.8 Hz, 1H), 3.05 (t, J=5.8 Hz, 1H), 2.87 (t, J=5.8 Hz, 1H), 2.72 (t, J=5.8 Hz, 1H), 2.55 (t, J=5.8 Hz, 1H); LC/MS: (ES+) m/z (M+H)$^+$=438; HPLC R$_t$=1.73 min., column O.

Preparation of Example 43

2-(1-(2-(4-(1H-pyrazol-3-yl)-5H-pyrrolo[3,2-d]pyrimidin-7-yl)-2-oxoacetyl)piperidin-4-ylidene)-2-phenylacetonitrile (Compound 59)

Example 43

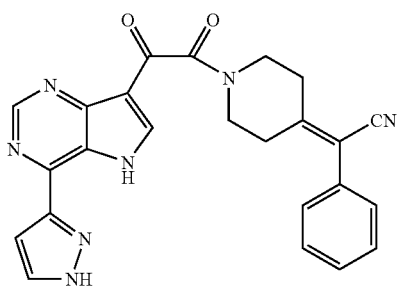

59

In a sealed tube dicarbonyl intermediate 33 (33 mg, 0.081 mmol), 3-(tributylstannyl)-1H-pyrazole (73 mg, 0.20 mmol), tetrakis(triphenylphosphine)-palladium(0) (20 mg, 0.02 mmol) and 1,4-dioxane (0.8 mL) were combined and heated at 130° C. with microwaves for 2 h. The reaction mixture was diluted with MeOH/DMSO (2:1, 1.5 mL), filtered and purified by preparative HPLC to yield 59 (3.4 mg, 0.008 mmol, 10%) as a yellow solid. $^1$H NMR: (500 MHz, CD$_3$COCD$_3$) δ 11.84 (br s, 1H), 9.06 (s, 0.5H), 9.05 (s, 0.5H), 8.58 (s, 0.5H), 8.55 (s, 0.5H), 8.01 (d, J=2.7 Hz, 0.5H), 8.01 (d, J=2.7 Hz, 0.5H), 7.55-7.32 (m, 5H), 7.24 (d, J=2.7 Hz, 0.5H), 7.23 (d, J=2.7 Hz, 0.5H), 4.01 (t, J=5.8 Hz, 1H), 3.84 (t, J=5.8 Hz, 1H), 3.74 (t, J=5.8 Hz, 1H), 3.56 (t, J=5.8 Hz, 1H), 3.07 (t, J=5.8 Hz, 1H), 2.84 (t, J=5.8 Hz, 1H), 2.78 (t, J=5.8 Hz, 1H), 2.54 (t, J=5.8 Hz, 1H); LC/MS: (ES+) m/z (M+H)$^+$=438; HPLC R$_t$=1.29 min., column L.

Biology

"μM" means micromolar;
"mL" means milliliter;
"μl" means microliter;
"mg" means milligram;

The materials and experimental procedures used to obtain the results reported in Tables 1-3 are described below.

Cells:
Virus production—Human embryonic Kidney cell line, 293, propagated in Dulbecco's Modified Eagle Medium (Life Technologies, Gaithersburg, Md.) containing 10% fetal Bovine serum (FBS, Sigma, St. Louis, Mo.).

Virus infection—Human epithelial cell line, HeLa, expressing the HIV-1 receptors CD4 and CCR5 was propagated in Dulbecco's Modified Eagle Medium (Life Technologies, Gaithersburg, Md.) containing 10% fetal Bovine serum (FBS, Sigma, St. Louis, Mo.) and supplemented with 0.2 mg/mL Geneticin (Life Technologies, Gaithersburg, Md.) and 0.4 mg/mL Zeocin (Invitrogen, Carlsbad, Calif.).

Virus-Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref 41). Transfections were performed using lipofectAMINE PLUS reagent as described by the manufacturer (Life Technologies, Gaithersburg, Md.).

Experiment

1. Compound was added to HeLa CD4 CCR5 cells plated in 96 well plates at a cell density of 1×10$^4$ cells per well in 100 μl Dulbecco's Modified Eagle Medium containing 10% fetal Bovine serum at a concentration of <20 μM.
2. 100 μl of single-round infectious reporter virus in Dulbecco's Modified Eagle Medium was then added to the plated cells and compound at an approximate multiplicity of infection (MOI) of 0.01, resulting in a final volume of 200 μl per well and a final compound concentration of <10 μM.
3. Samples were harvested 72 h after infection.
4. Viral infection was monitored by measuring luciferase expression from viral DNA in the infected cells using a luciferase reporter gene assay kit (Roche Molecular Biochemicals, Indianapolis, Ind.). Infected cell supernatants were removed and 50 μl of Dulbecco's Modified Eagle Medium (without phenol red) and 50 μl of luciferase assay reagent reconstituted as described by the manufacturer (Roche Molecular Biochemicals, Indianapolis, Ind.) was added per well. Luciferase activity was then quantified by measuring luminescence using a Wallac microbeta scintillation counter.
5. The percent inhibition for each compound was calculated by quantifying the level of luciferase expression in cells infected in the presence of each compound as a percentage of that observed for cells infected in the absence of compound and subtracting such a determined value from 100.

6. An $EC_{50}$ provides a method for comparing the antiviral potency of the compounds of this invention. The effective concentration for fifty percent inhibition ($EC_{50}$) was calculated with the Microsoft Excel Xlfit curve fitting software. For each compound, curves were generated from percent inhibition calculated at 10 different concentrations by using a four paramenter logistic model (model 205). The $EC_{50}$ data for the compounds is shown in Tables 2-4. Table 1 is the key for the data in Tables 2-4.

Cytoxicity assays were conducted with the same HeLa using methodology well known in the art. This method has been described in the literature (S Weislow, R Kiser, D L Fine, J Bader, R H Shoemaker and M R Boyd: New soluble-formazan assay for HIV-1 cytopathic effects: application to high-flux screening of synthetic and natural products for AIDS-antiviral activity. Journal of the National Cancer Institute. 81(8):577-586, 1989.

Cells were incubated in the presence of drug for six days, after which cell viability was measured using a dye reduction assay (MTT) and determined as a CC50. This assay measures the intracellular reducing activity present in actively respiring cells.

Results

TABLE 1

Biological Data Key for $EC_{50}$s

| Compounds* with $EC_{50}$s > 5 μM | Compounds with $EC_{50}$s > 1 μM but <5 μM | Compounds with EC50 > 50 nM but not yet tested at higher concentrations | Compounds with EC50 < 1 μM |
|---|---|---|---|
| Group C | Group B | Group A' | Group A |

*Some of these compounds may have been tested at a concentration lower than their $EC_{50}$ but showed some ability to cause inhibition and thus should be evaluated at a higher concentration to determine the exact $EC_{50}$.

TABLE 2

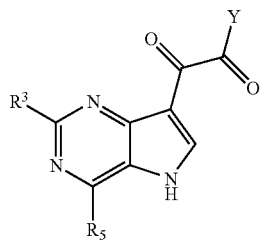

Examples

| Example Number | Compound Number | R3 | R5 | Y | EC50 Group from Table 1 |
|---|---|---|---|---|---|
| Example 2 | 10 | H | Cl | 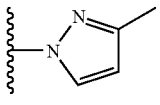 | A |
| Example 3 | 11 | H | 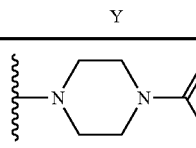 | 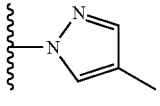 | A |
| Example 4 | 12 | H | 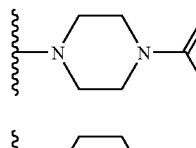 | 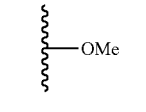 | A |
| Example 5 | 13 | H | —OMe | 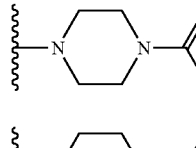 | A |
| Example 6 | 14 | H | 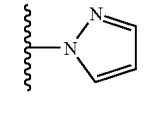 | 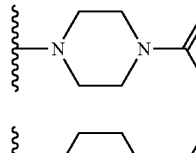 | A |
| Example 7 | 15 | H | 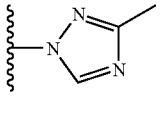 | 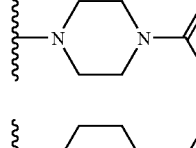 | A |

TABLE 2-continued

[Structure: pyrrolopyrimidine core with R3, R5 substituents and a -C(O)-C(O)-Y group at position 7]

Examples

| Example Number | Compound Number | R3 | R5 | Y | EC₅₀ Group from Table 1 |
|---|---|---|---|---|---|
| Example 8 | 16 | H | 1-(1,2,3-triazol-1-yl) | 4-benzoylpiperazin-1-yl | A |
| Example 9 | 17 | H | 1-(3-carboxypyrazol-1-yl) | 4-benzoylpiperazin-1-yl | A |

TABLE 3

[Structure: pyrrolopyrimidine core with R3, R5 substituents and a -C(O)-CH(CN)-Y group at position 7]

Examples

| Example No. | Cmpd. No. | R3 | R5 | Y | EC₅₀ Group from Table 1 |
|---|---|---|---|---|---|
| Example 1 | 9 | H | Cl | 4-benzoylpiperazin-1-yl | A |
| Example 10 | 18 | H | —OEt | 4-benzoylpiperazin-1-yl | A |
| Example 11 | 19 | H | —C(=O)CH₃ | 4-benzoylpiperazin-1-yl | A |
| Example 12 | 20 | H | —CN | 4-benzoylpiperazin-1-yl | A |

TABLE 3-continued

Examples

| Example No. | Cmpd. No. | R3 | R5 | Y | EC50 Group from Table 1 |
|---|---|---|---|---|---|
| Example 13 | 21 | H | pyrazole-C(O)N(CH3)2 | piperazine-C(O)Ph | A |
| Example 14 | 22 | H | pyrazole-C(O)-N-methylpiperazine | piperazine-C(O)Ph | A |
| Example 15 | 23 | H | pyrazole-phenyl | piperazine-C(O)Ph | A |
| Example 16 | 24 | H | pyrazole-(4-F-phenyl) | piperazine-C(O)Ph | A |
| Example 17 | 25 | H | pyrazole-(4-OMe-phenyl) | piperazine-C(O)Ph | A |
| Example 18 | 26 | H | pyrazole-(2-OMe-phenyl) | piperazine-C(O)Ph | A |
| Example 19 | 27 | H | pyrazole-(3-CF3-phenyl) | piperazine-C(O)Ph | A |

TABLE 3-continued
Examples
| Example No. | Cmpd. No. | R3 | R5 | Y | EC50 Group from Table 1 |
|---|---|---|---|---|---|
| Example 20 | 28 | H | 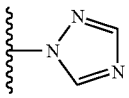 | 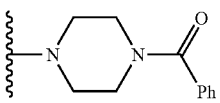 | A |
| Example 21 | 29 | H | 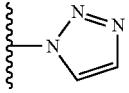 | 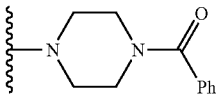 | A |
| Example 22 | 30 | H | 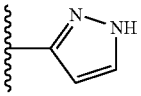 | 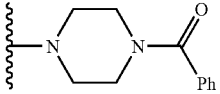 | A |
| Example 22 | 30 | H | 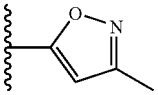 | 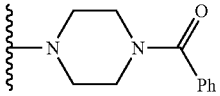 | A |
| Example 24 | 32 | H | 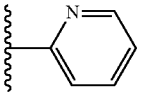 | 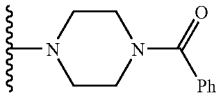 | A |
| Example 25 | 33 | H | 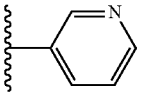 | 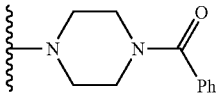 | A |
| Example 26 | 34 | H | 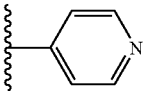 | 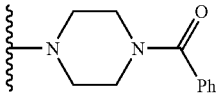 | A |
| Example 27 | 35 | H | 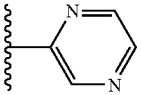 | 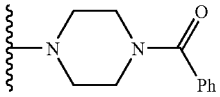 | A |
| Example 28 | 36 | H | 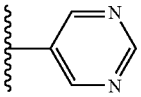 | 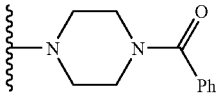 | A |
| Example 29 | 37 | H | 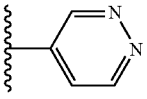 | 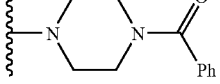 | A |

TABLE 3-continued
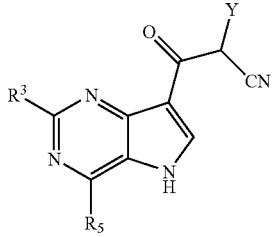
Examples
| Example No. | Cmpd. No. | R3 | R5 | Y | EC50 Group from Table 1 |
|---|---|---|---|---|---|
| Example 30 | 39 | H | Cl | 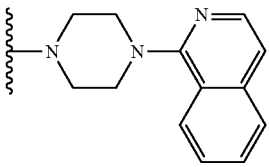 | A |
| Example 31 | 40 | H | 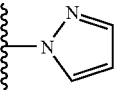 | 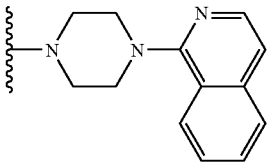 | A |
| Example 32 | 41 | H | 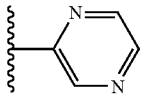 | 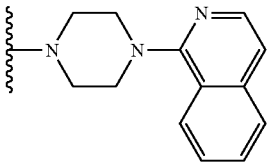 | A |
| Example 33 | 43 | H | Cl | 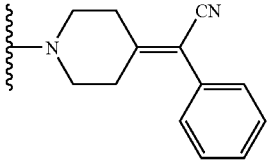 | A |
| Example 34 | 44 | H | 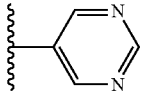 | 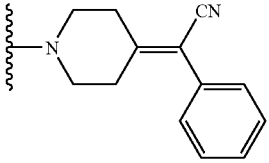 | A |
| Example 35 | 46 | H | Cl | 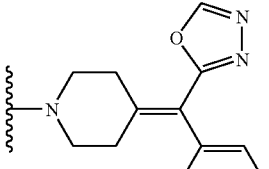 | A |

TABLE 3-continued

Examples

| Example No. | Cmpd. No. | R3 | R5 | Y | EC₅₀ Group from Table 1 |
|---|---|---|---|---|---|
| Example 36 | 47 | H | 1-pyrazolyl | piperidin-4-ylidene(phenyl)(1,3,4-oxadiazol-2-yl)methyl | A |
| Example 37 | 48 | H | 1-(1,2,4-triazolyl) | piperidin-4-ylidene(phenyl)(1,3,4-oxadiazol-2-yl)methyl | A |
| Example 38 | 53 | H | 1-pyrazolyl | piperidin-4-ylidene(cyano)(pyridin-2-yl)methyl | A |
| Example 39 | 54 | H | 3-(pyridin-2-yl)-1-pyrazolyl | 4-benzoylpiperazin-1-yl | A |
| Example 40 | 56 | H | 1-pyrazolyl | 4-(quinazolin-4-yl)piperazin-1-yl | A |
| Example 41 | 57 | H | 4-(1H-pyrazol-5-ylcarbonyl)piperazin-1-yl | 4-benzoylpiperazin-1-yl | A |

TABLE 3-continued

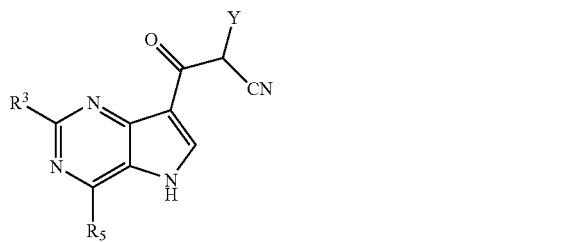

Examples

| Example No. | Cmpd. No. | R3 | R5 | Y | $EC_{50}$ Group from Table 1 |
|---|---|---|---|---|---|
| Example 42 | 58 | H | 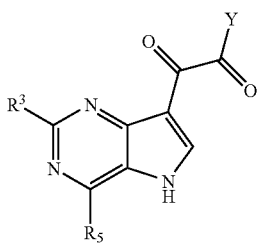 | (piperidine-C(CN)=phenyl) | A |
| Example 43 | 59 | H | (3-pyrazolyl NH) | (piperidine-C(CN)=phenyl) | A |

Table 4 shows other compounds of the invention which could be prepared by the methodology described herein and which are expected to have antiviral activity.

TABLE 4

| Example No. | Cmpd. No. | R3 | R5 | Y | $EC_{50}$ Group from Table 1 |
|---|---|---|---|---|---|
| Example # | # | H | (C(O)NH-4-pyridyl) | (piperazine-C(O)-Ph) | |
| | | H | (C(O)NH-pyridazinyl) | (piperazine-C(O)-Ph) | |

TABLE 4-continued
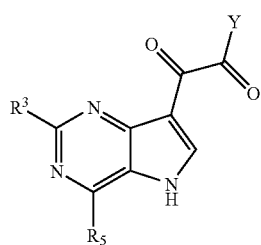
| Example No. | Cmpd. No. | R3 | R5 | Y | EC$_{50}$ Group from Table 1 |
|---|---|---|---|---|---|
| | | H | [pyrimidin-5-yl amide] | [piperazinyl-C(O)Ph] | |
| | | H | [pyridin-3-yl amide] | [piperazinyl-C(O)Ph] | |
| | | H | [thiazol-2-yl amide] | [piperazinyl-C(O)Ph] | |
| | | H | [NH$_2$ amide] | [piperazinyl-C(O)Ph] | |
| | | H | [NHCH$_3$ amide] | [piperazinyl-C(O)Ph] | |
| | | H | [1H-pyrazol-3-yl amide] | [piperazinyl-C(O)Ph] | |
| | | | [1-methyl-pyrazol-3-yl amide] | [piperazinyl-C(O)Ph] | |

TABLE 4-continued
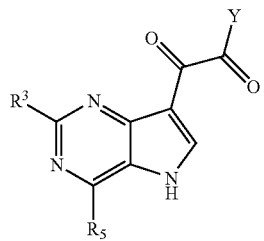
| Example No. | Cmpd. No. | R3 | R5 | Y | EC$_{50}$ Group from Table 1 |
|---|---|---|---|---|---|
| | | H | 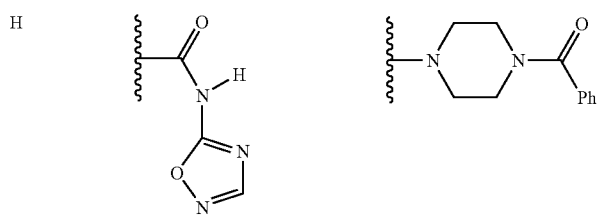 | | |
| | | H | 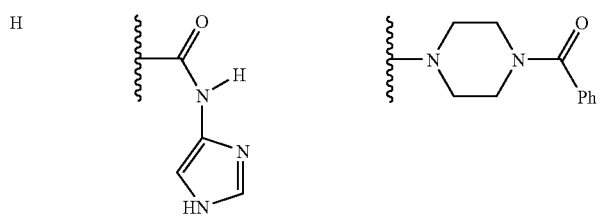 | | |
| | | H | 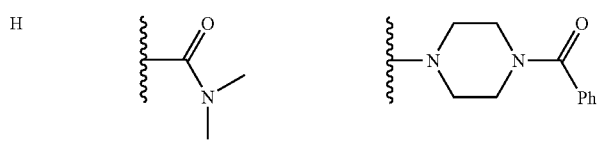 | | |
| | | H | 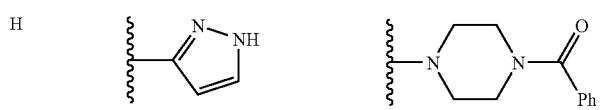 | | |
| | | H |  | | |
| | | H |  | | |
| | | H |  | | |

TABLE 4-continued

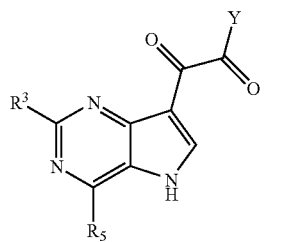

| Example No. | Cmpd. No. | R3 | R5 | Y | EC50 Group from Table 1 |
|---|---|---|---|---|---|
| | | H | N-OH oxime CH | piperazine-C(O)Ph | |
| | | H | pyrazole-NH2 | piperazine-C(O)Ph | |
| | | H | triazole-C(O)-N-methylpiperazine | piperazine-C(O)Ph | |
| | | H | pyrazole-C(O)N(CH3)2 | piperazine-C(O)Ph | |
| | | H | pyrazole-C(O)OH | piperazine-C(O)Ph | |
| | | H | pyrazole-C(O)-morpholine | piperazine-C(O)Ph | |
| | | H | pyrazole-F | piperazine-C(O)Ph | |
| | | H | triazole-CH3 | piperazine-C(O)Ph | |
| | | H | oxadiazolone | piperazine-C(O)Ph | |

TABLE 4-continued

| Example No. | Cmpd. No. | R3 | R5 | Y | EC₅₀ Group from Table 1 |
|---|---|---|---|---|---|
| | | H | —C≡C—CH₂CH₂—NMe₂ | piperazine-N-C(O)Ph | |
| | | H | —CH=CH—CH₂—NMe₂ | piperazine-N-C(O)Ph | |
| | | H | —CN | piperazine-N-C(O)Ph | |
| | | | | piperazine-N-C(O)Ph | |
| | | H | —C(O)NH-(4-pyridyl) | 4-(oxadiazol-2-yl(Ph)methylene)piperidine | |
| | | H | —C(O)NH-(pyridazin-4-yl) | 4-(oxadiazol-2-yl(Ph)methylene)piperidine | |
| | | H | —C(O)NH-(pyrimidin-5-yl) | 4-(oxadiazol-2-yl(Ph)methylene)piperidine | |
| | | H | —C(O)NH-(3-pyridyl) | 4-(oxadiazol-2-yl(Ph)methylene)piperidine | |
| | | H | —C(O)NH-(thiazol-2-yl) | 4-(oxadiazol-2-yl(Ph)methylene)piperidine | |

TABLE 4-continued

TABLE 4-continued

| Example No. | Cmpd. No. | R3 | R5 | Y | EC₅₀ Group from Table 1 |
|---|---|---|---|---|---|
| | | H | C(O)N(Me)₂ | piperidine-CH(Ph)-oxadiazole | |
| | | H | 1H-pyrazol-3-yl | piperidine-CH(Ph)-oxadiazole | |
| | | H | 1H-pyrazol-3-yl | piperidine-CH(Ph)-oxadiazole | |
| | | H | 1H-imidazol-2-yl | piperidine-CH(Ph)-oxadiazole | |
| | | H | isoxazol-3-yl | piperidine-CH(Ph)-oxadiazole | |
| | | H | CH=NOH | piperidine-CH(Ph)-oxadiazole | |
| | | H | 3-amino-pyrazol-1-yl | piperidine-CH(Ph)-oxadiazole | |

TABLE 4-continued

| Example No. | Cmpd. No. | R3 | R5 | Y | EC₅₀ Group from Table 1 |
|---|---|---|---|---|---|

TABLE 4-continued

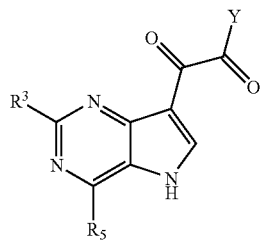

| Example No. | Cmpd. No. | R3 | R5 | Y | EC$_{50}$ Group from Table 1 |
|---|---|---|---|---|---|
| | | H | ⤳—≡—CH$_2$CH$_2$—NMe$_2$ | piperidine=CH(Ph)-(1,3,4-oxadiazol-2-yl) | |
| | | H | ⤳—CH=CH—CH$_2$CH$_2$—NMe$_2$ | piperidine=CH(Ph)-(1,3,4-oxadiazol-2-yl) | |
| | | | ⤳—CN | piperidine=CH(Ph)-(1,3,4-oxadiazol-2-yl) | |
| | | H | ⤳—C(O)NH-(pyridin-4-yl) | piperazine-N-(quinazolin-4-yl) | |
| | | H | ⤳—C(O)NH-(pyridazin-4-yl) | piperazine-N-(quinazolin-4-yl) | |
| | | H | ⤳—C(O)NH-(pyrimidin-5-yl) | piperazine-N-(quinazolin-4-yl) | |
| | | H | ⤳—C(O)NH-(pyridin-3-yl) | piperazine-N-(quinazolin-4-yl) | |

TABLE 4-continued

| Example No. | Cmpd. No. | R3 | R5 | Y | EC₅₀ Group from Table 1 |
|---|---|---|---|---|---|
| | | H | -C(O)NH-thiazol-2-yl | piperazinyl-quinazolin-4-yl | |
| | | H | -C(O)NH₂ | piperazinyl-quinazolin-4-yl | |
| | | H | -C(O)NHCH₃ | piperazinyl-quinazolin-4-yl | |
| | | H | -C(O)NH-(1H-pyrazol-3-yl) | piperazinyl-quinazolin-4-yl | |
| | | H | -C(O)NH-(1-methyl-1H-pyrazol-3-yl) | piperazinyl-quinazolin-4-yl | |
| | | H | -C(O)NH-(1,2,4-oxadiazol-5-yl) | piperazinyl-quinazolin-4-yl | |

TABLE 4-continued
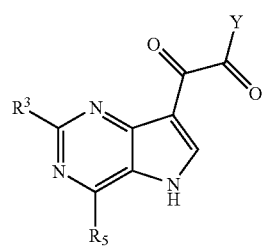
| Example No. | Cmpd. No. | R3 | R5 | Y | EC$_{50}$ Group from Table 1 |
|---|---|---|---|---|---|
| | | H | 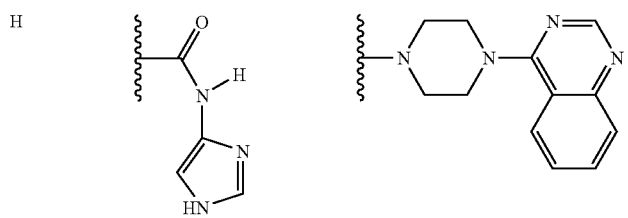 | | |
| | | H | 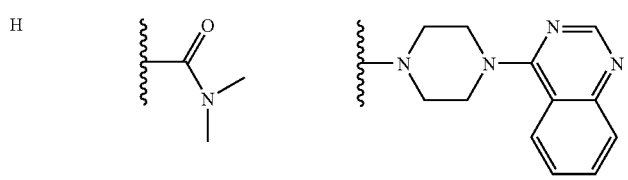 | | |
| | | H | 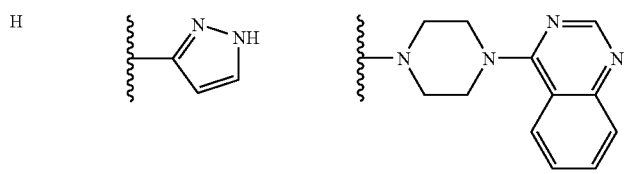 | | |
| | | H | 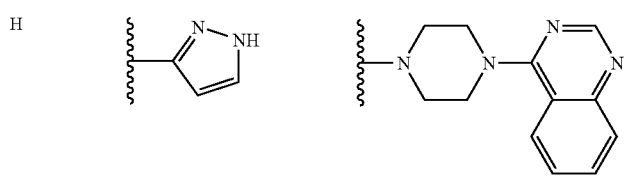 | | |
| | | H | 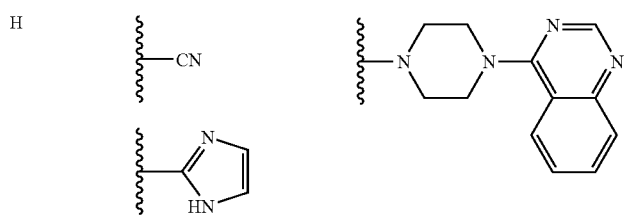 | | |
| | | H | 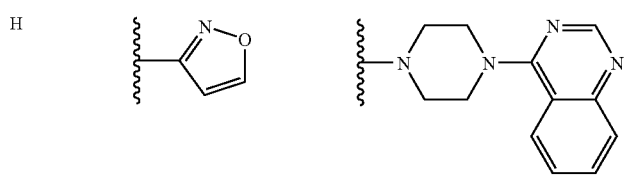 | | |

TABLE 4-continued

| Example No. | Cmpd. No. | R3 | R5 | Y | EC₅₀ Group from Table 1 |
|---|---|---|---|---|---|
| | | H | CH=NOH | piperazine-quinazoline | |
| | | H | 3-aminopyrazole | piperazine-quinazoline | |
| | | H | 1,2,4-triazole-3-carbonyl-4-methylpiperazine | piperazine-quinazoline | |
| | | H | pyrazole-3-carboxylic acid N,N-dimethylamide | piperazine-quinazoline | |
| | | H | pyrazole-3-carboxylic acid | piperazine-quinazoline | |
| | | H | pyrazole-3-carbonyl-morpholine | piperazine-quinazoline | |
| | | H | 3-fluoropyrazole | piperazine-quinazoline | |

TABLE 4-continued

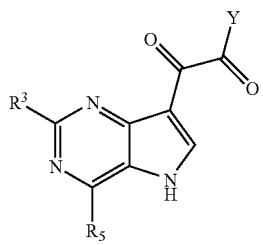

| Example No. | Cmpd. No. | R3 | R5 | Y | EC50 Group from Table 1 |
|---|---|---|---|---|---|
| | | H | 3-methyl-1H-1,2,4-triazol-5-yl | piperazinyl-quinazoline | |
| | | H | 2-oxo-2,3-dihydro-1,2,4-oxadiazol-5-yl | piperazinyl-quinazoline | |
| | | H | -C≡C-CH2-NMe2 | piperazinyl-quinazoline | |
| | | H | -CH=CH-CH2-NMe2 | piperazinyl-quinazoline | |
| | | H | -CN | piperazinyl-quinazoline | |

The compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically-effective amount of a compound of the present invention.

The pharmaceutical composition may be in the form of orally-administrable suspensions or tablets; nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

What is claimed is:

1. A compound or a pharmaceutically acceptable salt thereof of Formula I,

wherein:

Q is

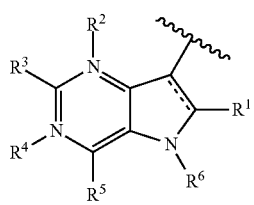

wherein $R^3$ is hydrogen, $C_1$-$C_3$ alkoxy, —$NR^{26}R^9$ or halogen;

T is —C(O)—;

$R^1$ is hydrogen;

$R^5$ is independently selected from the group consisting of C(O)$NH_2$, C(O)$NHCH_3$ and C(O)NHheteroaryl; wherein said C(O)NHheteroaryl is optionally substituted with one to three same or different halogens or from one to three same or different substituents selected from F;

$R^2$ and $R^4$ do not exist;

$R^6$ is $(CH_2)_nH$, wherein n is 0;

-- represents a carbon-carbon bond;

—Y— is selected from the group consisting of

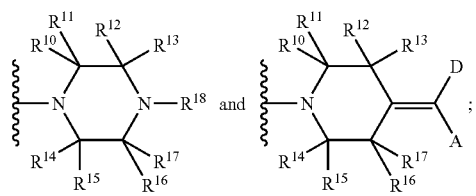

$R^{10}$, $R^{11}$, $R^{12}$, $R^{13}$, $R^{14}$, $R^{15}$, $R^{16}$ and $R^{17}$ are each independently H or methyl, with the proviso that a maximum of two of $R^{10}$-$R^{17}$ is a methyl;

$R^{18}$ is a member selected from the group consisting of C(O)-phenyl, C(O)-heteroaryl, pyridinyl, pyrimidinyl, quinolyl, isoquinolyl, quinazolyl, quinoxalinyl, napthyridinyl, pthalazinyl, azabenzofuryl and azaindolyl; wherein said member is optionally substituted with from one to two substituents selected from the group consisting of methyl, —amino, —NHMe, —$NMe_2$, methoxy, hydroxymethyl and halogen;

D is selected from the group consisting of hydrogen, cyano, $S(O)_2R^{24}$, halogen, $COOR^{20}$, $C(O)NR^{21}R^{22}$, phenyl and heteroaryl; wherein said phenyl or heteroaryl is independently optionally substituted with one to three same or different halogens or from one to three same or different substituents selected from the group consisting of ($C_{1-6}$)alkyl, ($C_{1-6}$)alkenyl, hydroxy, ($C_{1-6}$)alkoxy, halogen, —$NR^{24}R^{25}$, —$S(O)_2NR^{24}R^{25}$, $COOR^{26}$ and —$CONR^{24}R^{25}$; wherein said ($C_{1-6}$)alkyl is optionally substituted with one to three same or different halogen or a hydroxyl;

A is selected from the group consisting of phenyl, pyridinyl, furanyl, thienyl, isoxazole and oxazole; wherein said phenyl, pyridinyl, furanyl, thienyl, isoxazole or oxazole is independently optionally substituted with one to three same or different halogens or from one to three same or different substituents selected from the group consisting of ($C_{1-4}$)alkyl, ($C_{1-4}$)alkenyl, ($C_{1-3}$)alkoxy, halogen and —$NR_2$; wherein said ($C_{1-4}$)alkyl is optionally substituted with one to three same or different halogens;

heteroaryl is selected from the group consisting of pyridinyl, pyrazinyl, pyridazinyl, pyrimidinyl, furanyl, thienyl, benzothienyl, thiazolyl, oxazolyl, isoxazolyl, imidazolyl, oxadiazolyl, thiadiazolyl, pyrazolyl, tetrazolyl and triazolyl;

F is selected from the group consisting of ($C_{1-6}$)alkyl, ($C_{1-6}$)alkenyl, phenyl, pyridinyl, hydroxy, ($C_{1-6}$)alkoxy, halogen, benzyl, —$NR^{23}C(O)$—($C_{1-6}$)alkyl, —$NR^{24}R^{25}$, —$S(O)_2NR^{24}R^{25}$, $COOR^{26}$, —$COR^{27}$, and —$CONR^{24}R^{25}$; wherein said ($C_{1-6}$)alkyl or phenyl are each optionally substituted with hydroxy, ($C_{1-6}$)alkoxy, ($C_{1-6}$)alkyl, $CF_3$, dimethylamino or from one to three same or different halogen;

$R^9$ and $R^{26}$ are each independently selected from the group consisting of hydrogen and ($C_{1-6}$)alkyl;

$R^{20}$, $R^{23}$, $R^{24}$ and $R^{25}$ are independently selected from the group consisting of hydrogen, ($C_{1-6}$)alkyl, phenyl and heteroaryl; wherein said phenyl and heteroaryl are each independently optionally substituted with one to three same or different halogen or methyl;

$R^{21}$ and $R^{22}$ are each hydrogen; and $R^{27}$ is piperazinyl, N-methyl piperazinyl, or 3-pyrazolyl.

2. A compound of claim 1, wherein:
R$^{18}$ is —C(O)phenyl or —C(O) heteroaryl; wherein said heteroaryl is pyridinyl, furanyl or thienyl; wherein heteroaryl is independently optionally substituted with a member selected from the group consisting of halogen, methyl, -amino, —NHMe, NMe$_2$ and hydroxymethyl.

3. A compound of claim 1 wherein:
—W— is

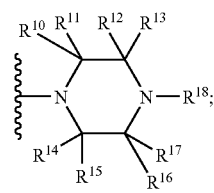

R$^{10}$, R$^{11}$, R$^{12}$, R$^{13}$, R$^{14}$, R$^{15}$, R$^{16}$ and R$^{17}$ are each independently H or methyl, with the proviso that not more than one is methyl; and R$^{18}$ is selected from the group consisting of pyridinyl, pyrimidinyl, quinolyl, isoquinolyl, quinazolyl, quinoxalinyl, napthyridinyl, pthalazinyl, azabenzofuryl and azaindolyl, each of which may be optionally substituted with from one to two substituents selected from the group consisting of methyl, -amino, —NHMe, —NMe$_2$, methoxy, hydroxymethyl and halogen.

4. A compound of claim 1 wherein:
—W— is

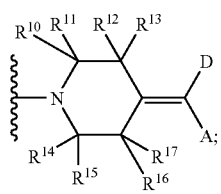

and R$^{10}$, R$^{11}$, R$^{12}$, R$^{13}$, R$^{14}$, R$^{15}$, R$^{16}$ and R$^{17}$ are each independently H or methyl, with the proviso that one is methyl.

5. A compound or a pharmaceutically acceptable salt thereof,

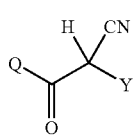

wherein:
Q is

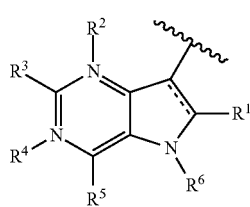

R$^1$ is hydrogen or methyl;

R$^3$ and R$^5$ are independently selected from the group consisting of hydrogen, halogen, cyano, nitro, COOR$^8$, XR$^9$ and B;

R$^2$ and R$^4$ are independently O or do not exist, with the proviso that only one of R$^2$ and R$^4$ are O;

R$^6$ is (CH$_2$)$_n$H, wherein n is 0-1;

-- represents a carbon-carbon bond or does not exist;

—Y— is selected from the group consisting of

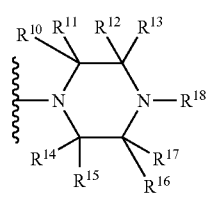 and 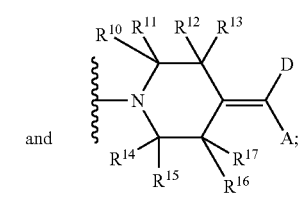

R$^{10}$, R$^{11}$, R$^{12}$, R$^{13}$, R$^{14}$, R$^{15}$, R$^{16}$ and R$^{17}$ are each independently H or (C$_{1-6}$)alkyl; wherein said (C$_{1-6}$)alkyl may optionally be substituted with one to three same or different halogen, OH or CN;

R$^{18}$ is a member selected from the group consisting of C(O)-phenyl, C(O)-heteroaryl, pyridinyl, pyrimidinyl, quinolyl, isoquinolyl, quinazolyl, quinoxalinyl, napthyridinyl, pthalazinyl, azabenzofuryl and azaindolyl;

wherein said member is optionally substituted with from one to two substituents selected from the group consisting of methyl, -amino, —NHMe, —NMe$_2$, methoxy, hydroxymethyl and halogen;

D is selected from the group consisting of hydrogen, cyano, S(O)$_2$R$^{24}$, halogen, COOR$^{20}$C(O) NR$^{21}$R$^{22}$, phenyl and heteroaryl; wherein said phenyl or heteroaryl is independently optionally substituted with one to three same or different halogens or from one to three same or different substituents selected from F;

A is selected from the group consisting of phenyl, pyridinyl, furanyl, thienyl, isoxazole and oxazole; wherein said phenyl, pyridinyl, furanyl, thienyl, isoxazole or oxazole is independently optionally substituted with one to three same or different halogens or from one to three same or different substituents selected from F;

B is selected from the group consisting of (C$_{1-6}$)alkyl, C(O)NR$^{21}$R$^{22}$, phenyl and heteroaryl; wherein said (C$_{1-6}$)alkyl, phenyl and heteroaryl are independently optionally substituted with one to three same or different halogens or from one to three same or different substituents selected from F;

heteroaryl is selected from the group consisting of pyridinyl, pyrazinyl, pyridazinyl, pyrimidinyl, furanyl, thienyl, thiazolyl, oxazolyl, isoxazolyl, imidazolyl, oxadiazolyl, thiadiazolyl, pyrazolyl, tetrazolyl and triazolyl;

F is selected from the group consisting of (C$_{1-6}$)alkyl, (C$_{1-6}$)alkenyl, phenyl, pyridinyl, hydroxy, (C$_{1-6}$)alkoxy, halogen, benzyl, —NR$^{23}$C(O)—(C$_{1-6}$)alkyl, —NR$^{24}$R$^{25}$,

155

—S(O)$_2$NR$^{24}$R$^{25}$, COOR$^{26}$, —COR$^{27}$, and —CONR$^{24}$R$^{25}$; wherein said (C$_{1-6}$)alkyl or phenyl are each optionally substituted with hydroxy, (C$_{1-6}$)alkoxy, dimethylamino or from one to three same or different halogen;

R$^8$, R$^9$ and R$^{26}$ are each independently selected from the group consisting of hydrogen and (C$_{1-6}$)alkyl;

X is selected from the group consisting of NR$^{26}$, O and S;

R$^{20}$, R$^{21}$, R$^{22}$, R$^{23}$, R$^{24}$ and R$^{25}$ are independently selected from the group consisting of hydrogen, (C$_{1-6}$)alkyl, phenyl and heteroaryl; wherein said phenyl and heteroaryl are each independently optionally substituted with one to three same or different halogen or methyl; and R$^{27}$ is piperazinyl, N-methylpiperazinyl or 3-pyrazolyl.

6. A compound or a pharmaceutically acceptable salt thereof of Formula I,

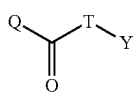
(I)

wherein Q is

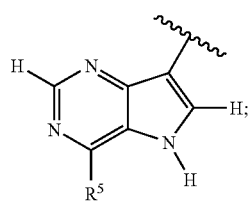

T is —C(O)—;

R$^5$ is selected from the group consisting of hydrogen, halogen, cyano, XR$^9$, heteroaryl, —(CH$_2$CH$_2$)$_2$NC(O)pyrazolyl, and —C(O)CH$_3$, wherein said heteroaryl is optionally substituted with one substituent selected from F;

heteroaryl is selected from the group consisting of pyridinyl, pyrazinyl, pyridazinyl, pyrimidinyl, isoxazolyl, isoxazolyl, pyrazolyl, and triazolyl;

—Y— is selected from the group consisting of

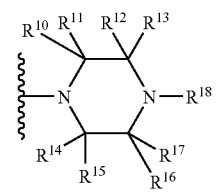 and 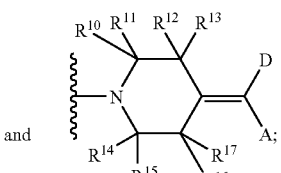

R$^{10}$, R$^{11}$, R$^{12}$, R$^{13}$, R$^{14}$, R$^{15}$, R$^{16}$ and R$^{17}$ are each hydrogen;

A is phenyl or pyridinyl;

R$^{18}$ is C(O)-phenyl, isoquinolyl or quinazolyl;

D is cyano or oxadiazolyl;

F is selected from the group consisting of (C$_{1-6}$)alkyl, phenyl, pyridinyl, (C$_{1-2}$)alkoxy, —COOR$^{26}$ —COR$^{27}$ and —CONR$^{24}$R$^{25}$; wherein said phenyl is

156 optionally substituted with one group selected from methyl, methoxy, fluoro, or trifluoromethyl;

X is selected from the group consisting of O;

R$^9$ is (C$_{1-2}$)alkyl;

R$^{26}$ is hydrogen, methyl, or ethyl;

R$^{24}$ and R$^{25}$ are independently selected from the group consisting of hydrogen and methyl; and R$^{27}$ is piperazinyl, N-methyl piperazinyl, or 3-pyrazolyl.

7. A compound of claim 6 wherein:

R$^5$ is heteroaryl optionally substituted with one substituent selected from F;

—Y— is

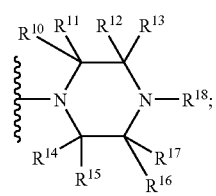

R$^{18}$ is C(O)-phenyl, isoquinolyl or quinazolyl; and

F is (C$_{1-6}$)alkyl.

8. A compound of claim 7 wherein R$^{18}$ is C(O)-phenyl.

9. A compound of claim 7 wherein R$^{18}$ is isoquinolyl or quinazolyl.

10. A compound of claim 6 wherein:

R$^5$ is heteroaryl optionally substituted with one substituent selected from F;

heteroaryl is selected from the group consisting of pyridinyl, pyrazinyl, pyridazinyl, pyrimidinyl, isoxazolyl, isoxazolyl, pyrazolyl and triazolyl; and —Y— is

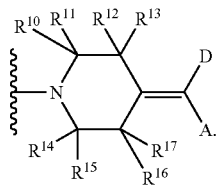

11. A compound of claim 6 wherein:

Q is

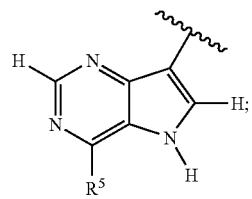

R$^5$ is heteroaryl optionally substituted with one substituent selected from F; and heteroaryl is selected from the group consisting of pyrazolyl and triazolyl.

12. A compound of claim 11 wherein:

F is selected from the group consisting of methyl and —CONR$^{24}$R$^{25}$; and

R$^{24}$ and R$^{25}$ are independently selected from the group consisting of hydrogen and methyl.

13. A compound of claim 12 wherein:
F is methyl.

14. A pharmaceutical composition which comprises an antiviral effective amount of a compound or a pharmaceutically acceptable salt thereof of Formula I, as claimed in claim 1, and one or more pharmaceutically acceptable carriers, excipients or diluents.

15. A method of ameliorating HIV comprising administering to a mammal an antiviral effective amount of a compound of Formula I, including pharmaceutically accceptable salts thereof, as claimed in claim 1, and one or more pharmaceutically acceptable carriers, excipients or diluents.

16. The method of claim 15 comprising administering to said mammal an antiviral effective amount of a compound of Formula I, including pharmaceutically accceptable salts thereof, in combination with an antiviral effective amount of an AIDS treatment agent selected from the group consisting of an AIDS antiviral agent; an anti-infective agent; an immunomodulator; and an HIV entry inhibitor.

* * * * *